(12) United States Patent
Endo et al.

(10) Patent No.: US 8,022,047 B2
(45) Date of Patent: Sep. 20, 2011

(54) COMBINATION ANTICANCER AGENTS

(75) Inventors: Mika Endo, Kanagawa (JP); Masako Ura, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 495 days.

(21) Appl. No.: 12/064,352

(22) PCT Filed: Aug. 22, 2006

(86) PCT No.: PCT/JP2006/316353
§ 371 (c)(1),
(2), (4) Date: Jul. 10, 2008

(87) PCT Pub. No.: WO2007/023778
PCT Pub. Date: Mar. 1, 2007

(65) Prior Publication Data
US 2009/0149478 A1 Jun. 11, 2009

(30) Foreign Application Priority Data
Aug. 22, 2005 (JP) .................. 2005-240424

(51) Int. Cl.
*C07D 471/04* (2006.01)
*C07D 471/22* (2006.01)
*A01N 43/04* (2006.01)
*A61K 31/70* (2006.01)

(52) U.S. Cl. ........................... 514/49; 514/257

(58) Field of Classification Search .................. None
See application file for complete search history.

(56) References Cited

U.S. PATENT DOCUMENTS

| | | | |
|---|---|---|---|
| 4,943,579 A | 7/1990 | Vishnuvajjala et al. |
| 4,975,278 A | 12/1990 | Senter et al. |
| 6,130,039 A | 10/2000 | Bandman et al. |
| 6,245,750 B1 | 6/2001 | Shepard |
| 6,265,540 B1 | 7/2001 | Isaacs et al. |
| 6,294,344 B1 | 9/2001 | O'Brien |
| 6,825,194 B2 | 11/2004 | Murata et al. |
| 7,109,195 B2 | 9/2006 | Murata et al. |
| 7,595,400 B2 | 9/2009 | Fukuda et al. |
| 2001/0016329 A1 | 8/2001 | Shepard |
| 2002/0012663 A1 | 1/2002 | Waksal |
| 2002/0086815 A1 | 7/2002 | McMorris et al. |
| 2003/0138864 A1 | 7/2003 | Ishitsuka et al. |
| 2008/0015157 A1 | 1/2008 | Umeda et al. |
| 2009/0118271 A1 | 5/2009 | Endo et al. |
| 2009/0312554 A1 | 12/2009 | Fukuda et al. |
| 2009/0326225 A1 | 12/2009 | Fukuda et al. |

FOREIGN PATENT DOCUMENTS

| | | |
|---|---|---|
| AU | 199853264 B2 | 7/1998 |
| CN | 1241192 A | 1/2000 |
| CN | 1361700 A | 7/2002 |
| CN | 1424912 A | 6/2003 |
| EP | 0 074 256 B1 | 3/1983 |
| EP | 0 220 601 B1 | 5/1987 |
| EP | 0 296 597 B1 | 12/1988 |
| EP | 0 471 358 B1 | 2/1992 |
| EP | 0 495 432 B1 | 7/1992 |
| EP | 0 506 478 A1 | 9/1992 |
| EP | 0 667 165 A1 | 8/1995 |
| EP | 0 807 115 A | 11/1997 |
| EP | 0 897 924 B1 | 2/1999 |
| EP | 0 923 566 B1 | 10/2003 |
| EP | 1 757 609 A1 | 2/2007 |
| EP | 1 854 792 A1 | 11/2007 |
| GB | 2 334 256 A | 8/1999 |
| JP | 02-071836 A | 3/1990 |
| JP | 06-087746 A | 3/1994 |
| JP | 09-241298 A | 9/1997 |
| JP | 10-513187 A | 12/1998 |
| JP | 11-158080 A | 6/1999 |
| JP | 2000-517304 A | 12/2000 |
| JP | 2002-505672 A | 2/2002 |
| JP | 2002-114710 A | 4/2002 |
| JP | 2003-520195 A | 7/2003 |
| JP | 2003-523980 A | 8/2003 |
| JP | 2004-535363 A | 11/2004 |
| JP | 2005-047934 A | 2/2005 |
| JP | 2005-511643 A | 4/2005 |
| JP | 2005-514359 A | 5/2005 |
| JP | 2005-255643 A | 9/2005 |
| WO | WO 90/03169 A1 | 4/1990 |
| WO | WO 95/22549 A1 | 8/1995 |
| WO | WO 96/23794 A1 | 8/1996 |

(Continued)

OTHER PUBLICATIONS

Stella et al. Prodrugs: Challenges and Rewards, Part 1, 2007.*

(Continued)

*Primary Examiner* — Brandon Fetterolf
*Assistant Examiner* — Anna Pagonakis
(74) *Attorney, Agent, or Firm* — Foley & Lardner LLP

(57) ABSTRACT

A cancer therapeutic agent comprising a combination of compound A described below, or a pharmaceutically acceptable salt thereof, and compound B described below, or a pharmaceutically acceptable salt thereof:

Compound A represented by the formula of claim 1 and

Compound B represented by:

at least one type of compound selected from the group consisting of a platinum-type anticancer compound, selected from the group consisting of cisplatin carboplatin, oxaliplatin and nedaplatin; a gemcitabine-type compound, selected from the group consisting of gemcitabine and Ara-C; a 5-FU-type compound, selected from the group consisting of 5-FU, doxifluridine, UFT, carmofur, S-1, and capecitabine; a texane-type compound, selected from the group consisting of Taxol, Taxotere, IDN 5109, BMS 188797 BMS 184476 paclitaxel and docetaxel; a vinca alkaloid-type compound, selected from the group consisting of vinorelbine, vincristine, vinblastine, and videsine; an anticancer tyrosine kinase inhibitor compound, and an anticancer monoclonal antibody.

4 Claims, 11 Drawing Sheets

FOREIGN PATENT DOCUMENTS

| | | |
|---|---|---|
| WO | WO 96/38146 A1 | 12/1996 |
| WO | WO 98/07713 A1 | 2/1998 |
| WO | WO 98/13059 A1 | 4/1998 |
| WO | WO 98/28304 A1 | 7/1998 |
| WO | WO 98/35940 A1 | 8/1998 |
| WO | WO 98/51787 A2 | 11/1998 |
| WO | WO 98/56807 A1 | 12/1998 |
| WO | WO 98/57662 A2 | 12/1998 |
| WO | WO 99/05103 A2 | 2/1999 |
| WO | WO 00/51991 A1 | 9/2000 |
| WO | WO 00/63418 A1 | 10/2000 |
| WO | WO 01/20331 A1 | 3/2001 |
| WO | WO 01/49291 A1 | 7/2001 |
| WO | WO 01/62235 A2 | 8/2001 |
| WO | WO 02/00168 A2 | 1/2002 |
| WO | WO 02/10741 A2 | 2/2002 |
| WO | WO 02/056885 A1 | 7/2002 |
| WO | WO 02/070658 A2 | 9/2002 |
| WO | WO 02/100172 A1 | 12/2002 |
| WO | WO 03/043631 A2 | 5/2003 |
| WO | WO 03/045952 A2 | 6/2003 |
| WO | WO 2004/012662 A2 | 2/2004 |
| WO | WO 2004/014386 A1 | 2/2004 |
| WO | WO 2004/073601 A2 | 9/2004 |
| WO | WO 2005/097803 A1 | 10/2005 |
| WO | WO 2006/028904 A1 | 3/2006 |
| WO | WO 2006/090743 A1 | 8/2006 |

OTHER PUBLICATIONS

Fujimoto-Ouchi et al. Antitumor activity of combinations of anti-HER-2 antibody trastuzumab and oral fluropyrimidines capecitabine/5'-dFUrd in human breast cancer models. Cancer Chemother. Pharmacol. 2002, 49: 211-216.*

Chemical Encyclopedic Dictionary, K.L. Knuniants Editor, 1983, 130-131, with English translation, 4 pages.

The Global Bioresource Center, Product Description, Cell Biology, ATCC No. CCL-247, 4 pages (no date, accessed online Jan. 21, 2010).

Albin et al., "Main Drug-metabolizing Enzyme Systems in Human Breast Tumors and Peritumoral Tissues," Cancer Research, vol. 53, Aug. 1, 1993, pp. 3541-3546.

Alevizos et al., "Oral cancer in vivo gene expression profiling assisted by laser capture microdissection and microarray analysis," Oncogene, vol. 20, Sep. 2001, pp. 6196-6204.

Batetta et al., "G6PD activity and gene expression in leukemic cells from G6PD-deficient subjects," Cancer Letters, vol. 140, Jun. 1999, pp. 53-58.

Beall et al., "Mechanisms of action of quinone-containing alkylating agents I: NQ01-directed drug development," Frontiers in Bioscience, vol. 5, Jul. 1, 2000, pp. 639-648.

Bielawska et al., "Cytotoxicity activity of L-proline analogues of anthraquinone-2-carboxylic acid in breast cancer MCF-7 cells," Folia Histochemica et Cytobiologica, vol. 39, suppl. 2, May 2001, pp. 207-208.

Bielawska et al., "Prodilase as a prodrug converting enzyme III. Synthesis of praline analogues of melphalan and their susceptibility to the action of prolidase," Rocz. Akad. Med. Bialymst., vol. 44, 1999, pp. 190-199.

Bielawska et al., "Prolidase as a prodrug converting enzyme II. Synthesis of praline analogue of anthraquinone-2-carboxylic acid and its susceptibility to the action of prolidase," Rocz. Akad. Med. Bialymst., vol. 43, 1998, pp. 201-209.

Bielawska et al., "Prolidase-activated prodrug for cancer chemotherapy Cytotoxic activity of proline analogue of chlorambucil in breast cancer MCF-7 cells," Il Farmaco, vol. 55, Nov.-Dec. 2000, pp. 736-741.

Buckhaults et al., "Secreted and Cell Surface Genes Expressed in Benign and Malignant Colorectal Tumors," Cancer Research, Oct. 1, 2001, 61:6996-7001.

Ciaccio et al., "Modulation of Detoxification Gene Expression in Human Colon HT29 Cells by Glutathione-S-Transferase Inhibitors," Mol. Pharamcol., vol. 48, No. 4, Oct. 1995, pp. 639-647.

Connors et al., "Prodrugs in Cancer Chemotherapy," Stem Cells, Sep. 1995, 13(5):501-511.

Defeo-Jones et al., "A Peptide-Doxorubicin 'Prodrug' Activated by Prostate-Specific Antigen Selectively Kills Prostate Tumor Cells Positive for Prostate-Specific Antigen in Vivo," Nature medicine, Nov. 2000, vol. 6, No. 11:1248-1252.

El-Rifai et al., "Expression Profiling of Gastric Adenocarcinoma Using cDNA Array," Int. J. Cancer, Apr. 2, 2001, 93:832-838.

Englebretsen et al., "An N-Terminal Method for Peptide Solubilisation," Tetrahedron, May 21, 1999, 55(21):6623-6634.

Gasa et al., "Elevated Activities and Properties of Arylsulfatases A and B and B-Variant in Human Lung Tumors," Cancer Research, vol. 40, No. 10, Oct. 1980, pp. 3804-3809.

Greengard et al., "The Undifferentiated Enzymic Composition of Human Fetal Lung and Pulmonary Tumors," Cancer Research, vol. 37, No. 3, Mar. 1977, pp. 884-891.

Herzfeld et al., "Enzyme Activities in Human Fetal and Neoplastic Tissues," Cancer, vol. 46, No. 9, Nov. 1980, pp. 2047-2054.

Herzfeld et al., "Human Colon Tumors," Cancer, vol. 42, No. 3, Sep. 1978, pp. 1280-1283.

Hooper et al., "Renal Dipeptidase is One of the membrane Proteins Released by Phosphatidylinositol-Specific Phospholipase C," Biochemistry Journal, 1987, 244:465-469.

Hsu et al., "Overexpression of dihydrodiol Dehydrogenase as a Prognostic Marker of Non-Small Cell Lung Cancer," Cancer Research, vol. 61, No. 6, Mar. 15, 2001, pp. 2727-2731.

Kapitonov et al., "Cloning, Characterization, and Expression of Human Ceramide Galactosyltransferase cDNA," Biochemical and Biophysical Research Communications, vol. 232, Mar. 1997, pp. 449-453.

Karna et al., "Collagen metabolism disturbances are accompanied by an increase in prolidase activity in lung carcinoma planoepitheliale," Int. J. Exp. Path., vol. 81, No. 5, Oct. 2000, pp. 341-347.

Kashima et al., "Expression of Oligodendrocyte-associated Genes in Cell Lines Derived from Human Gliomas and Neuroblastomas," Cancer Research, vol. 53, Jan. 1, 1993, pp. 170-175.

Kirschmann et al., "Differentially expressed genes associated with the metastatic phenotype in breast cancer," Breast Cancer Research and Treatment, vol. 55, No. 2, May 1999, pp. 127-136.

Krovat et al., "Fingerprinting of cytochrome P450 and Microsomal Epoxide Hydrolase Gene Expression in Human Blood Cells," Toxicological Sciences, vol. 55, No. 2, Jun. 2000, pp. 352-360.

Kuivaniemi et al., "Deficient production of lysyl oxidase in cultures of malignantly transformed human cells," FEBS Lett, vol. 195, No. 1-2, Jan. 1986, pp. 261-264.

Kuo et al., "Human glucose-6-phosphate dehydrogenase (G6PD) gene transforms NIH 3T3 cells and induces tumors in nude mice," Int. J. Cancer, vol. 85, No. 6, Mar. 2000, pp. 857-864.

Lam et al., The Journal of Biological Chemistry, 2000, vol. 275, No. 26:19676-19684.

Leenders et al., "Synthesis and evaluation of novel duanomycin-phosphate-sulfate-β-glucuronide and -β-glucoside prodrugs for application in adept," Bioorganic & Medical Chemistry Letters, vol. 5, No. 24, Dec. 21, 1995, pp. 2975-2980.

Li et al., "Partial characterization of a cDNA for human stearoyl-CoA desaturase and changes in its mRNA expression in some normal and malignant tissues," Int. J. Cancer, vol. 57, No. 3, May 1, 1994, pp. 348-352.

Lin et al., "Role of Pharmacokinetics and Metabolism in Drug Discovery and Development," Pharmacological Reviews, vol. 49, No. 4, Dec. 1997, pp. 403-449.

Liu et al., "Identification of Differentially Expressed Prostate Genes: Increased Expression of Transcription Factor ETS-2 in Prostate Cancer," Prostate, vol. 30, No. 3, Feb. 15, 1997, pp. 145-153.

Lopaczynska et al., "Upregulation of pyrroline-5-carboxylate reductase in benzo(a)pyrene resistant human tumor cells (MCF-7): a redox-dependent mechanism for resistance to benzo(a)pyrene," Proc. of the Annual Meeting of the American Assoc. for Cancer Research, vol. 36, No. 122, Mar. 1995, #724.

Lopez De Cerain et al., "Carbonyl Reductase and NADPH Cytochrome P450 Reductase Activities in Human Tumoral Versus Normal Tissues," Eur. J. Cancer, vol. 35, No. 2, Feb. 1999, pp. 320-324.

Lou et al., "Genomic Organization and Chromosomal Localization of a Novel Human Hepatic Dihydrodiol Dehydrogenase with High Affinity Bile Acid Binding," J. Biol. Chem.., vol. 269, No. 11, Mar. 18, 1994, pp. 8416-8422.

Lu et al., "Gene Expression Changes Associated with Chemically Induced Rat Mammary Carcinogenesis," Molecular Carcinogenesis, vol. 20, No. 2, Oct. 1997, pp. 204-215.

Maeda et al., "Automated determination of 5-fluorouracil and its metabolite in urine by high-performance liquid chromatorgraphy with column switching," J. Chromatogr. B, vol. 731, No. 2, Aug. 1999, pp. 267-273.

Miwa et al., Eur. J. Cancer, 1998, 34:1274-1281.

Myllyla et al., "Regulation of collagen post-translational modification in transformed human and chick-embryo cells," Biochem. J., vol. 196, No. 3, Jun. 15, 1981, pp. 683-692.

Naguib et al., "Enzymes of Uracil Catabolism in Normal and Neoplastic Human Tissues," Cancer Research, vol. 45, No. 11.1, Nov. 1, 1985, pp. 5405-5412.

Okabe et al., "Genome-Wide Analysis of Gene Expression in Human Hepatocellular Carcinomas Using cDNA Microarray: Identification of Genes Involved in Viral Carcinogenesis and Tumor Progression," Cancer Research, Mar. 1, 2001, 61:2129-2137.

Page et al., "Proteomic definition of normal human luminal and myoepithelial breast cells purified from reduction mammoplasties," Proc. Natl. Acad. Sci. USA, vol. 96, No. 22, Oct. 26, 1999, pp. 12589-12594.

Paterson et al., "Regulation of Glutamine: Fructose-6-Phosphate Amidotransferase Gene Trascription by Epidermal Growth Factor and Glucose," Endocrinology, vol. 136, No. 7, Jul. 1995, pp. 2809-2816.

Pihlajaniemi et al., "Effects of Strptozotocin Diabetes, Glucose, and Insulin on the Metabolism of Type IV Collagen and Proteoglycan in Murine Basement Membrane-forming EHS Tumor Tissue," J. Biol. Chem., vol. 257, No. 24, Dec. 25, 1982, vol. 14914-14920.

Polak et al., "Localization of Bombesin-like Peptides in Tumors," Ann. N. Y. Acad. Sci., vol. 547, 1988, pp. 322-335.

Rihn et al., "Differential gene expression in mesothelioma," FEBS Lett., vol. 480, No. 2-3, Sep. 1, 2000, pp. 95-100.

Ross et al., Nature Genetics, Mar. 2000, 24:227-235.

Santos et al., "Cyclization-activated prodrugs. Synthesis, reactivity and toxicity of dipeptide esters of paracetamol," Bioorganic & Medicinal Chemistry Letters, Mar. 15, 2005, 15(6):1595-1598.

Schena et al., Science, 1995, 270:467-470.

Shin et al., "Spatial and temporal expression of UDP-galactose: ceramide galactosyl transferase mRNA during rat brain development," Anat. Embryol., vol. 200, No. 2, Aug. 1999, pp. 193-201.

Skala et al., "Molecular cloning and expression of rat aldolase C messenger RNA during development and hepatocarcinogenesis," Eur. J. Biochem., vol. 163, No. 3, Mar. 16, 1987, pp. 513-518.

Van Der Slot et al., "Elevated formation of pyridinoline cross-links by profibrotic cytokines is associated with enhanced lysyl hydroxylase 2b levels," Biochim. Biophys. Acta., vol. 1741, No. 1-2, Jun. 30, 2005, pp. 95-102.

Wang et al., "Monitoring gene expression profile changes in ovarian carcinomas using cDNA microarray," vol. 229, No. 1-2, Mar. 18, 1999, pp. 101-108.

Welsh et al., "Analysis of Gene Expression Identifies Candidate Markers and Pharmacological Targets in Prostate Cancer," Cancer Research, Aug. 15, 2001, 61:5974-5978.

Yamamoto et al., "Screening and Production of Arylsulfatases for Target Therapy with Etoposide 4'-sulfate, an Antitumor Prodrug," Biosci. Biotech. Biochem., vol. 59, No. 6, Jun. 1995, pp. 1057-1061.

Yu et al., "The correlation of membranous glycoprotein-GP-170, cytoplasmic glutathione and glucose-6-phosphate dehydrogenase levels with multidrug resistance in transitional cell carcinoma cell lines of the urinary tract," J. Urol., vol. 157, No. 2, Feb. 1997, pp. 727-731.

Zhang et al., "Mechanism of Enolase: The Crystal Structure of Assymmetric Dimer Enolase-2-Phospho-D-glycerate/Enolase—Phosophoenolpyruvate at 2.0 A Resolution," Biochemistry, 1997, 36:12526-12534.

Zhou et al., "The Pattern of Gene Expression in Human CD34+ Stem/Progenitor Cells," PNAS, Nov. 20, 2001, 98(24):13966-13971.

Office Action dated Apr. 23, 2010, in corresponding Chinese Application CN20068039397, 7 pages.

Bedeschi et al., "Synthesis and Antitumor Activity of a New Class of Water Soluble Camptothecin Derivatives," Bioorganic Med. Chem. Lett., 1996, 6(6):671-674.

Gelderblom et al., "Oral Topoisomerase 1 inhibitors in adult patients: present and future," Invest. New Drugs, 1999, 17:401-415.

Gerrits et al., "Topoisomerase 1 inhibitors: the relevance of prolonged exposure for present clinical development," British J. of Cancer, 1997, 76(7):952-962.

Hatefi et al., "Camptothecin Delivery Methods," Pharm. Res., 2002, 19(10):1389-1399.

Kehrer et al., "Modulation of camptothecin analogs in the treatment of cancer: a review," Anti-Cancer Drugs, 2001, 12:89-105.

Kingsbury et al., "Synthesis of Water-Soluble (aminoalkyl)camptothecin Analogues: Inhibition of Topoisomerase I and Antitumor Activity," J. Med. Chem., 1991, 34:98-107.

Kunimoto et al., "Antitumor Activity of 7-Ethyl-10-[4-(1-piperidino)-1-piperidino]carbonyloxycamptothecin, a Novel Water-soluble Derivative of Camptothecin, against Murine Tumors," Cancer Research, Nov. 15, 1987, 47: 5944-5947.

O'Leary et al., "Camptothecins: A Review of their Development and Schedules of Administration," Eur. J. of Cancer, 1998, 34(10):1500-1508.

Simone, Joseph V., Oncology, Introduction, Cecil Textbook of Medicine, $20_{th}$ Edition, vol. 1, 1996, pp. 1004-1010.

Sugimori et al., "Antitumor Agents. VI. Synthesis and Antitumor Activity of Ring A-, Ring B- and Ring C-Modified Derivatives of Camptothecin," Heterocycles, 1994, 38(1):81-94.

Sugimori et al., "Synthesis and Antitumor Activity of Ring A- and F-Modified Hexacyclic Camptothecin Analogues," J. Med. Chem., 1998, 41(13):2308-2318.

Sugimori et al., "Antitumor Agents. 7. Synthsis and Antitumor Activity of Novel Hexacyclic Camptothecin Analogues," J. Med. Chem., 1994, 37(19):3033-3039.

Vey et al., "The Topoisomerase I Inhibitor DX-8951f is Active in a Severe Combined Immunodeficient Mouse Model of Human Acute Myelogenous Leukemia," Clin. Cancer Res., Feb. 2000, 6:731-736.

Wall et al., "Plant Antitumor Agents. I. The Isolation and Structure of Camptothecin, a Novel Alkaloidal Leukemia and Tumor Inhibitor from *Camptotheca acuminate*," J. Am. Chem. Soc., 1966, 88(16):3888-3890.

Wani et al., "Plant Antitumor Agents. 23. Synthesis and Antileukemic Activity of Camptothecin Analogues," J. Med. Chem., 1986, 29:2358-2363.

Zunino et al., "Camptothecins in clinical development," Expert Opin. Investig. Drugs, 2004, 13(3):269-284.

Notice of Allowance in U.S. Appl. No. 10/546,287 (now US 7,595,400).

Non-Final Office Action mailed May 5, 2010, in U.S. Appl. No. 12/083,831.

Non-Final Office Action mailed Sep. 15, 2009, in U.S. Appl. No. 11/547,036.

Non-Final Office Action mailed Apr. 30, 2010, in U.S. Appl. No. 11/547,036.

Eng et al., "Biological agents versus chemotherapy in the treatment of colorectal cancer," Expert Opin. Pharmacother., Jul. 2006, 7(10):1251-1271.

Kawahara, Masaaki, "Irinotecan in the treatment of small cell lung cancer: a review of patient safety considerations," Expert Opin. Drug Saf., Mar. 2006, 5(2):303-312.

Kulke, Matthew H., "Advanced pancreatic cancer: is there a role for combination therapy?", Expert Rev. Anticancer Ther., Oct. 2003, 3(5):729-739.

Narahara et al., "Multi-agent combination chemotherapy comprising CPT-11," Jpn. J. Cancer Chemother., Nov. 2004, 31(12):1973-1977, and English translation, 10 pages.

Sasaki, Igaku no Ayumi, Jan. 31, 1998, 184(5):375-379 (see Intl Search Report for concise explanation of relevance).

Sato et al., "Positioning of combination chemotherapy for advanced gastric acner," Igaku no Ayumi, Jan. 31, 1998, 184(5):347-351, and English translation, 9 pages.

Shan et al., "Prodrug Strategies Based on Intramolecular Cyclization Reactions," J. Pharm. Sci., Jul. 1997, 86(7):765-767.

Wöhrer et al., "Palliative chemotherapy for advanced gastric cancer," Annals of Oncology, Nov. 2004, 15(11):1585-1595.

Supplementary European Search Report dated Aug. 4, 2010, in EP 05728811.0, 3 pages.

Del Poeta et al., "Comparison of in Vitro Activities of Camptothecin and Nitidine Derivatives against Fungal and Cancer Cells," Antimicrobial Agents and Chemotherapy, Dec. 1999, 43(12):2862-2868.

Smith, Michael B., Organic Synthesis, McGraw-Hill, Inc., 1994, Chapter 1, 3 pages.

Shamis et al., "Bioactivation of Self-Immolative Dendritic Prodrugs by Catalytic Antibody 38C2," J. Am. Chem. Soc., 2004, 126:1726-1731.

* cited by examiner

COMBINATION ANTICANCER AGENTS

CROSS-REFERENCE TO RELATED APPLICATIONS

This application is a National Stage application of PCT/JP2006/316353, filed Aug. 22, 2006, which claims priority from Japanese application JP 2005-240424, filed Aug. 22, 2005.

TECHNICAL FIELD

The present invention relates to novel combination anticancer therapeutic agents.

BACKGROUND ART

Camptothecins, platinum-type anticancer compounds such as cisplatin, and anticancer compounds such as taxanes are active against a wide variety of tumor cells, and are expected as therapeutic agents such as anticancer agents (Patent Documents 1 and 2). Some of these compounds are excellent anticancer agents, but there is a demand for further activity improvement.

Many of these compounds are lipophilic, and because of their low water solubility, their use in injections (parenteral administration) is sometimes limited (Patent Document 1). Water-soluble prodrugs have been studied in an attempt to solubilize such lipophilic pharmaceutical agents in water (Non-Patent document 1 and Patent Document 1).

[Patent Document 1] WO 03/043631
[Patent Document 2] WO 03/045952
[Non-Patent Document 1] Shan et al., J. Pharm. Sci., 86(7), 765-767, 1997

DISCLOSURE OF THE INVENTION

Problems to be Solved by the Invention

An objective of the present invention is to further improve the anticancer effect of camptothecins and other anticancer agents.

Most water-soluble prodrugs of lipophilic pharmaceutical agents are converted into their active form after administration, mainly by enzymes. However, this conversion occurs after a certain period of time following administration and varies among species and individuals, and thus has been an obstacle to the development of these prodrugs. Therefore, there was a high demand to develop water-soluble prodrugs that can be administered parenterally, which do not depend on enzymatic conversion and show small interspecies or individual differences.

Furthermore, in some cases, the rate and efficiency in converting a prodrug to its active form in blood was insufficient, and therefore, there was a need to shorten the time taken for the blood concentration of pharmaceutical agents to increase. The inventors of the present application have already succeeded in providing water-soluble prodrugs that can be administered parenterally, show small interspecies or individual differences and do not depend on enzymatic conversion, and have an excellent rate and efficiency in converting into the active form (PCT/JP2005/6957: published as WO 05/097803 after the priority date of this application). Therefore, an objective of the present invention is to further improve the anticancer effects of, preferably, camptothecins including specific water-soluble prodrugs, and other anticancer agents.

Means for Solving the Problems

The present inventors conducted dedicated research to solve the above-mentioned problems. As a result, they discovered that combined use of a specific anticancer agent and camptothecins having a particular structure, or water-soluble prodrugs thereof, significantly increases their anticancer effects, and thereby completed the present invention.

Accordingly, the present invention comprises the following:

[1] a cancer therapeutic agent comprising a combination of compound A described below, or a pharmaceutically acceptable salt thereof, and compound B described below, or a pharmaceutically acceptable salt thereof:

Compound A: compound A1 represented by formula (1) below, or water-soluble prodrug A2 thereof;

Compound B: at least one type of compound selected from the group consisting of a platinum-type anticancer compound, a gemcitabine-type compound, a 5-FU-type compound, a taxane-type compound, a vinca alkaloid-type compound, an anticancer tyrosine kinase inhibitor compound, and an anticancer monoclonal antibody;

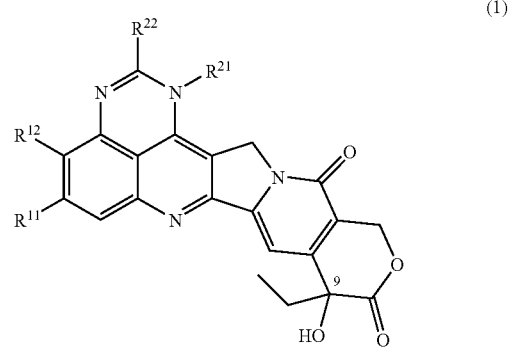

(1)

(wherein, $R^{11}$ represents a hydrogen atom, a halogen atom, or a C1-C6 alkyl group;

$R^{12}$ represents a hydrogen atom, a halogen atom, a C1-C6 alkyl group, or a hydroxyl group;

$R^{21}$ represents a hydrogen atom or a C1-C10 alkyl group which may comprise one to three substituents selected from Group B described below:

Group B: a C1-C6 alkoxy group, a hydroxy group, a halogen atom, an amino group, a mono-C1-C6 alkylamino group, a di-C1-C6 alkylamino group, a C3-C7 cycloalkyl group, a heterocycle, and an aryl ring (the aryl ring may comprise one to three substituents selected from the group consisting of a hydroxy group, a C1-C6 alkoxy group, a halogen atom, an amino group, a mono-C1-C6 alkylamino group, and a di-C1-C6 alkylamino group); and $R^{22}$ represents a hydrogen atom, an amino group, or a C1-C6 alkyl group that may comprise one to three substituents selected from Group C described below, a C1-C6 alkoxy group that may comprise one to three substituents selected from Group C described below, a C1-C6 alkylthio group that may comprise one to three substituents selected from Group C described below, a mono-C1-C6 alkylamino group that may comprise one to three substituents selected from Group C described below, or a di-C1-C6 alkylamino group that may comprise one to three substituents selected from Group C described below:

Group C: a C1-C6 alkoxy group, a hydroxy group, a halogen atom, an amino group, a C3-C7 cycloalkyl group, a heterocycle, and an aryl ring (the aryl ring may comprise one to three substituents selected from the group consisting of a hydroxy group, a C1-C6 alkoxy group, an amino group, a mono-C 1-C6 alkylamino group, and a di-C1-C6 alkylamino group);

[2] the cancer therapeutic agent of [1], wherein Compound A is Compound A1 described above, and Compound B is a platinum-type anticancer compound;

[3] the cancer therapeutic agent of [1], wherein Compound A is water-soluble prodrug A2 of compound A1 described above, and Compound B is at least one type of compound selected from the group consisting of a platinum-type anticancer compound, a gemcitabine-type compound, a 5-FU-type compound, a taxane-type compound, a vinca alkaloid-type compound, an anticancer tyrosine kinase inhibitor compound, and an anticancer monoclonal antibody;

[4] the cancer therapeutic agent of [1] or [3], wherein the cancer therapeutic agent further comprises leucovorin when Compound B comprises a 5-FU-type compound;

[5] the cancer therapeutic agent of any one of [1] to [4], wherein water-soluble prodrug A2 is a compound represented by formula (2) described below:

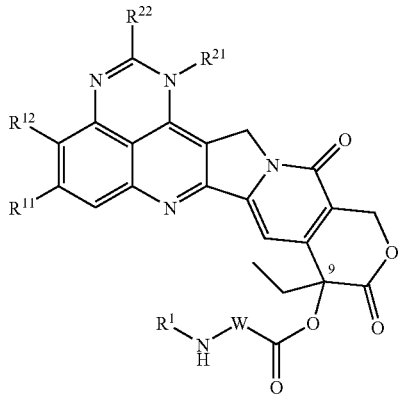

(2)

(wherein, $R^{11}$, $R^{12}$, $R^{21}$, and $R^{22}$ are as defined in [1];
$R^1$ represents a hydrogen atom or a C1-C6 alkyl group; and
W represents a divalent group comprising a secondary amino group, a divalent group comprising a tertiary amino group, or a divalent group comprising a sulfonyl group);

[6] the cancer therapeutic agent of any one of [1] to [5], wherein water-soluble prodrug A2 is a compound represented by formula (3) described below:

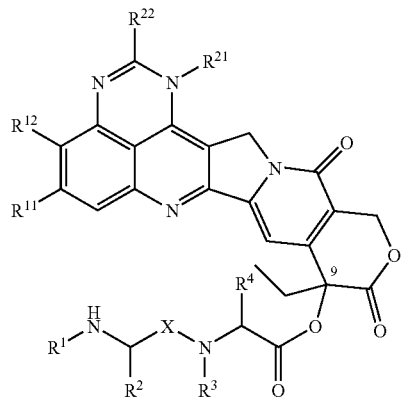

(3)

(wherein, $R^{11}$, $R^{12}$, $R^{21}$, and $R^{22}$ are as defined in [1];
$R^1$ represents a hydrogen atom or a C1-C6 alkyl group; and
$R^2$ and $R^4$ individually represent a hydrogen atom, a C1-C6 alkyl group, or an amino acid side chain, $R^3$ represents a C1-C6 alkyl group, and X represents C=O or a C1-C3 alkylene group);

[7] the cancer therapeutic agent of [6], wherein $R^1$ is a hydrogen atom, a methyl group, or an ethyl group;
[8] the cancer therapeutic agent of [6] or [7], wherein $R^2$ is a hydrogen atom or a methyl group;
[9] the cancer therapeutic agent of any one of [6] to [8], wherein $R^3$ is a C1-C3 alkyl group;
[10] the cancer therapeutic agent of any one of [6] to [9], wherein $R^4$ is a hydrogen atom or a methyl group;
[11] the cancer therapeutic agent of any one of [1] to [5], wherein water-soluble prodrug A2 is a compound represented by formula (4) described below:

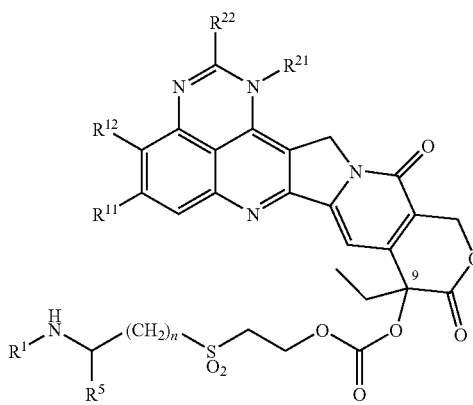

(4)

(wherein, $R^{11}$, $R^{12}$, $R^{21}$, and $R^{22}$ are as defined in [1];
$R^1$ represents a hydrogen atom or a C1-C6 alkyl group;
$R^5$ represents a hydrogen atom or —COOR$^6$ (wherein, $R^6$ represents a hydrogen atom or a C1-C6 alkyl group); and
n represents an integer of 1 to 6);

[12] the cancer therapeutic agent of [11], wherein $R^1$ is a hydrogen atom, a methyl group, or an ethyl group;
[13] the cancer therapeutic agent of [11] or [12], wherein n is 1 and $R^5$ is a hydrogen atom or —COOR$^6$ (wherein, $R^6$ represents a hydrogen atom or a C1-C6 alkyl group);
[14] the cancer therapeutic agent of [11] or [12], wherein n is an integer of 2 to 6, and $R^5$ is a hydrogen atom;

[15] the cancer therapeutic agent of any one of [1] to [5], wherein water-soluble prodrug A2 is a compound represented by formula (5) described below:

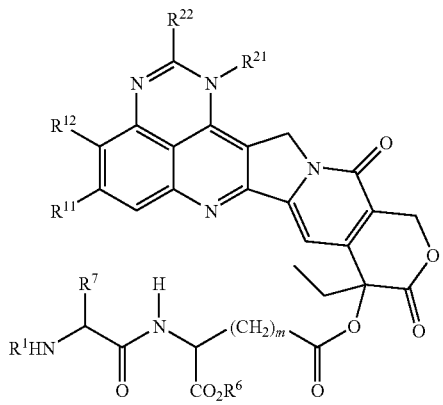

(wherein, $R^{11}$, $R^{12}$, $R^{21}$, and $R^{22}$ are as defined in [1];
$R^1$ represents a hydrogen atom or a C1-C6 alkyl group;
$R^6$ represents a hydrogen atom, a branched C3-C10 alkyl group, or a C3-C8 cycloalkyl group;
$R^7$ is a side chain of a naturally occurring or non-naturally occurring amino acid; and
m is an integer of 1 to 3);

[16] the cancer therapeutic agent of [15], wherein $R^1$ is a hydrogen atom;

[17] the cancer therapeutic agent of [15] or [16], wherein $R^6$ is a hydrogen atom;

[18] the cancer therapeutic agent of any one of [15] to [17], wherein $R^7$ is 2-methylpropyl, cyclohexylmethyl, benzyl, indol-3-ylmethyl, 4-aminobutyl, or 4-aminopropyl;

[19] the cancer therapeutic agent of any one of [1] to [18], wherein
$R^{11}$ is a hydrogen atom;
$R^{12}$ is a hydrogen atom or a C1-C3 alkyl group;
$R^{21}$ is a hydrogen atom or a C1-C8 alkyl group that may comprise one to three substituents selected from Group D described below; and
$R^{22}$ is a hydrogen atom, an amino group, or a C1-C6 alkyl group that may comprise one to three substituents selected from Group D described below, a C1-C6 alkoxy group that may comprise one to three substituents selected from Group D described below, a C1-C6 alkylthio group that may comprise one to three substituents selected from Group D described below, a mono-C1-C6 alkylamino group that may comprise one to three substituents selected from Group D described below, or a di-C1-C6 alkylamino group that may comprise one to three substituents selected from Group D described below:

Group D: a C1-C3 alkoxy group, a hydroxy group, a halogen atom, an amino group, a mono-C1-C3 alkylamino group, a di-C1-C3 alkylamino group, a C3-C7 cycloalkyl group, a heterocycle, and an aryl ring (the aryl ring may comprise one to three substituents selected from the group consisting of a hydroxy group, a C1-C3 alkoxy group, and a halogen atom);

[20] the cancer therapeutic agent of any one of [1] to [19], wherein compound A1 or active form (A1) of water-soluble prodrug A2 thereof, is at least one type of compound selected from the group consisting of:

a) (9S)-1-butyl-9-ethyl-9-hydroxy-1H,12H-pyrano[3",4":6',7']indolizino[1',2':6,5]pyrido[4,3,2-de]quinazoline-10,13(9H,15H)-dione;

b) (9S)-9-ethyl-9-hydroxy-1-[2-(4-morpholino)ethyl]-1H,12H-pyrano[3",4":6',7']indolizino[1',2':6,5]pyrido[4,3,2-de]quinazoline-10,13(9H,15H)-dione;

c) (9S)-9-ethyl-9-hydroxy-1-propyl-1H,12H-pyrano[3",4":6',7']indolizino[1',2':6,5]pyrido[4,3,2-de]quinazoline-10,13(9H,15H)-dione;

d) (9S)-1-benzyl-9-ethyl-9-hydroxy-1H,12H-pyrano[3",4":6',7']indolizino[1',2':6,5]pyrido[4,3,2-de]quinazoline-10,13(9H,15H)-dione;

e) (9S)-9-ethyl-9-hydroxy-1-phenethyl-1H,12H-pyrano[3",4":6',7']indolizino[1',2':6,5]pyrido[4,3,2-de]quinazoline-10,13(9H,15H)-dione;

f) (9S)-2,9-diethyl-9-hydroxy-1-phenethyl-1H,12H-pyrano[3",4":6',7']indolizino[1',2':6,5]pyrido[4,3,2-de]quinazoline-10,13(9H,15H)-dione;

g) (9S)-9-ethyl-9-hydroxy-1-(3-phenylpropyl)-1H,12H-pyrano[3",4":6',7']indolizino[1',2':6,5]pyrido[4,3,2-de]quinazoline-10,13(9H,15H)-dione;

h) (9S)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

i) (9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

j) (9S)-2,9-diethyl-9-hydroxy-1-(2-methylpropyl)-1H,12H-pyrano[3",4":6',7']indolizino[1',2':6,5]pyrido[4,3,2-de]quinazoline-10,13(9H,15H)-dione;

k) (9S)-9-ethyl-1-heptyl-9-hydroxy-1H,12H-pyrano[3",4":6',7']indolizino[1',2':6,5]pyrido[4,3,2-de]quinazoline-10,13(9H,15H)-dione;

l) (9S)-9-ethyl-9-hydroxy-1-methyl-1H,12H-pyrano[3",4":6',7']indolizino[1',2':6,5]pyrido[4,3,2-de]quinazoline-10,13(9H,15H)-dione;

m) (9S)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione;

n) (9S)-9-ethyl-1-hexyl-9-hydroxy-1H,12H-pyrano[3",4":6',7']indolizino[1',2':6,5]pyrido[4,3,2-de]quinazoline-10,13(9H,15H)-dione;

o) (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione;

p) (9S)-1,9-diethyl-9-hydroxy-1H,12H-pyrano[3",4":6',7']indolizino[1',2':6,5]pyrido[4,3,2-de]quinazoline-10,13(9H,15H)-dione;

q) (9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-10,13(9H,15H)-dione;

r)
(9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-10,13(9H,15H)-dione;
s)
(9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-10,13(9H,15H)-dione;
t)
(9S)-9-ethyl-1-[2-(4-fluorophenyl)ethyl]-9-hydroxy-2-methyl-1H,12H-pyrano[3",4":6',7']indolizino[1',2':6,5]pyrido[4,3,2-de]quinazoline-10,13(9H,15H)-dione;
u)
(9S)-9-ethyl-9-hydroxy-1-(1-methylethyl)-1H,12H-pyrano[3",4":6',7']indolizino[1',2':6,5]pyrido[4,3,2-de]quinazoline-10,13(9H,15H)-dione;
v)
(9S)-1-(3,3-dimethylbutyl)-9-ethyl-9-hydroxy-1H,12H-pyrano[3",4":6',7']indolizino[1',2':6,5]pyrido[4,3,2-de]quinazoline-10,13(9H,15H)-dione;
w)
(9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13(9H,15H)-dione;
x)
(9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;
y)
(9RS)-9-ethyl-9-hydroxy-4-methyl-1-pentyl-1H,12H-pyrano[3",4":6',7']indolizino[1',2':6,5]pyrido[4,3,2-de]quinazoline-10,13(9H,15H)-dione;
z)
(9S)-9-ethyl-9-hydroxy-1-(2-hydroxyethyl)-1H,12H-pyrano[3",4":6',7']indolizino[1',2':6,5]pyrido[4,3,2-de]quinazoline-10,13(9H,15H)-dione;
aa)
(9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H,15H)-dione;
bb)
(9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione;
cc)
(9S)-2,9-diethyl-9-hydroxy-1-pentyl-1H,12H-pyrano[3",4":6',7']indolizino[1',2':6,5]pyrido[4,3,2-de]quinazoline-10,13(9H,15H)-dione;
dd)
(9S)-9-ethyl-9-hydroxy-1-pentyl-2-propyl-1H,12H-pyrano[3",4":6',7']indolizino[1',2':6,5]pyrido[4,3,2-de]quinazoline-10,13(9H,15H)-dione;
ee)
(9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione;
ff)
(9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13(9H,15H)-dione;
gg)
(9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione;

hh)
(9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;
ii)
(9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,15H)-dione;
jj)
(9S)-9-ethyl-9-hydroxy-1-pentyl-2-trifluoromethyl-1H,12H-pyrano[3",4":6',7']indolizino[1',2':6,5]pyrido[4,3,2-de]quinazoline-10,13(9H,15H)-dione;
kk)
(9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13(9H,15H)-dione;
ll)
(9S)-9-ethyl-2-ethylthio-9-hydroxy-1-(3-methylbutyl)-1H,12H-pyrano[3",4":6',7']indolizino[1',2':6,5]pyrido[4,3,2-de]quinazoline-10,13(9H,15H)-dione;
mm)
(9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione; and
nn)
(9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

[21] the cancer therapeutic agent of any one of [1] to [10], wherein water-soluble prodrug A2 is represented by the following formula:

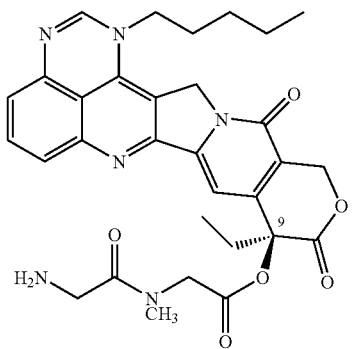

[22] the cancer therapeutic agent of [1] or [2], wherein compound A1 is represented by the following formula:

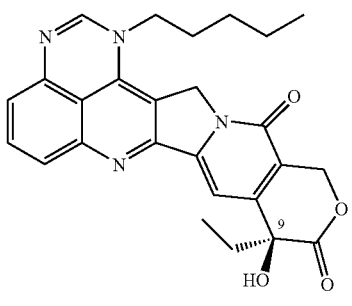

[23] the cancer therapeutic agent of any one of [1] to [22], which is a compounded agent;

[24] the cancer therapeutic agent of any one of [1] to [22], wherein the cancer therapeutic agent is a kit which comprises a pharmaceutical agent comprising compound A and a pharmaceutical agent comprising compound B;
[25] the cancer therapeutic agent of any one of [1] to [24], wherein the cancer is a solid tumor;
[26] the cancer therapeutic agent of any one of [1] to [25], wherein the cancer is colorectal cancer, lung cancer, breast cancer, stomach cancer, cervical cancer, bladder cancer, rectal cancer, pancreatic cancer, and/or ovarian cancer;
[27] a method for treating cancer comprising the step of administering to a patient a therapeutically effective dose of the cancer therapeutic agent of any one of [1] to [26]; and
[28] use of the cancer therapeutic agent of any one of [1] to [26] for preparing a therapeutic agent for cancer.

As used herein, the term "alkyl group" refers to a monovalent group, which is derived by removing a single hydrogen atom from an aliphatic hydrocarbon, and has a partial assembly of hydrocarbyl or hydrocarbon structure comprising hydrogen and carbon atoms, and does not contain a heteroatom or an unsaturated carbon-carbon bond in its backbone. The alkyl group may have a straight-chain or branched-chain structure.

The term "C1-C3 alkyl group" refers to an alkyl group with 1 to 3 carbon atoms, the term "C1-C6 alkyl group" refers to an alkyl group with 1 to 6 carbon atoms, the term "C1-C8 alkyl group" refers to an alkyl group with 1 to 8 carbon atoms, the term "C1-C10 alkyl group" refers to an alkyl group with 1 to 10 carbon atoms, and the term "C3-C10 alkyl group" refers to an alkyl group with 3 to 10 carbon atoms.

Specific examples of the "alkyl group" include a methyl group, ethyl group, n-propyl group, i-propyl group, n-butyl group, sec-butyl group, t-butyl group, isobutyl group, pentyl group, isopentyl group, 2,3-dimethylpropyl group, hexyl group, 2,3-dimethylhexyl group, 1,1-dimethylpentyl group, heptyl group, and octyl group.

As used herein, the term "alkylene group" refers to a divalent group derived by removing a second hydrogen atom from the "alkyl group" defined above, and examples of the alkylene group preferably include a C1-C3 alkylene group, and more preferably include a C 1-C2 alkylene group. Specific examples of the alkylene group include a methylene group, 1,2-ethylene group, 1,1-ethylene group, 1,3-propylene group, tetramethylene group, pentamethylene group, and hexamethylene group.

As used herein, the term "alkoxy group" refers to an —O—R' group, wherein R' is the alkyl group defined above. Examples of the "C1-C6 alkoxy group" include a methoxy group, ethoxy group, propoxy group, isopropoxy group, butoxy group, isobutoxy group, tert-butoxy group, pentoxy group, 3-methylbutoxy group, and 2,2-dimethylpropoxy group.

As used herein, the term "alkylthio group" refers to an —S—R' group, in which R' is the alkyl group defined above. Examples of the "C1-C8 alkylthio group" include a methylthio group, ethylthio group, propylthio group, butylthio group, pentylthio group, hexylthio group, heptylthio group, and octylthio group.

As used herein, the term "hydroxy group" refers to an HO— group.

As used herein, the term "halogen atom" refers to a fluorine atom, chlorine atom, bromine atom, or iodine atom.

As used herein, the term "amino group" refers to an $NH_2$— group, and includes amino groups protected with formyl, acetyl, trityl, tert-butoxycarbonyl, benzyl, benzyloxycarbonyl, and such protecting groups that are well known in the art. Among the amino groups, $NH_2$— is preferred.

As used herein, the term "monoalkylamino group" refers to an —NH—R' group, wherein R' is the alkyl group defined above, and comprises amino groups which, through substitution of the hydrogen atom on the nitrogen atom, are protected with formyl, acetyl, trityl, tert-butoxycarbonyl, benzyl, benzyloxycarbonyl, and such protecting groups that are well known in the art. Examples of the "mono-C1-C6 alkylamino group" preferably include an N-methylamino group, N-ethylamino group, N-propylamino group, N-isopropylamino group, N-butylamino group, N-(1-methylpropyl)amino group, N-(2-methylpropyl)amino group, and N-pentylamino group, and more preferably include N-ethylamino group, N-propylamino group, and N-butylamino group.

As used herein, the term "dialkylamino group" refers to an —NR'R" group, wherein R' and R" (each independently) represents an alkyl group defined above. Examples of the "di-C1-C6 alkylamino group" preferably include an N,N-dimethylamino group, N,N-diethylamino group, N,N-dipropylamino group, N,N-diisopropylamino group, N,N-dibutylamino group, N-methyl-N-ethylamino group, and N-methyl-N-propylamino group, and more preferably include an N,N-dimethylamino group and N,N-diethylamino group.

As used herein, the term "tertiary amino group" refers to a group in which all of the hydrogens of an amino group are substituted.

As used herein, the term "C3-C7 cycloalkyl group" refers to a 3- to 7-membered ring that does not comprise any heteroatom in the ring. The term "C3-C8 cycloalkyl group" refers to a 3- to 8-membered ring that does not comprise any heteroatom in the ring. Examples of the "cycloalkyl group" preferably include a cyclopropyl group, cyclobutyl group, cyclopentyl group, cyclohexyl group, and cycloheptyl group, and more preferably include a cyclopentyl group and cyclohexyl group.

As used herein, the term "heterocycle" refers to a 3- to 10-membered ring comprising one or more heteroatoms selected from N, S, and O. Preferred examples of such include an oxazolyl group, thiazolyl group, 4,5-dihydrooxazolyl group, 4,5-dihydrothiazolyl group, furyl group, pyrolyl group, thienyl group, imidazolyl group, triazolyl group, tetrazolyl group, pyridyl group, pyrazinyl group, pyrimidinyl group, triazinyl group, oxadiazolyl group, thiadiazolyl group, pyrrolidinyl group, tetrahydrothienyl group, tetrahydrofuryl group, morpholinyl group, piperidyl group, piperazinyl group, and 1-methylpiperazinyl group, and more preferably include an imidazolyl group, pyridyl group, morpholinyl group, and pyrrolidinyl group.

As used herein, the term "aryl ring" refers to an aromatic carbocyclic group, or more specifically a 6- to 10-membered aromatic ring or a partially aromatic ring, and examples include phenyl, naphthyl, and tetrahydronaphthyl rings, preferably phenyl and naphthyl rings, and most preferably phenyl rings.

The term "pharmaceutically acceptable salt" refers to a common salt of the water-soluble prodrug represented by formula (1), which is formed with an appropriate nontoxic organic or inorganic acid, or an organic or inorganic base, and which maintains the prodrug's biological efficacy and characteristic.

Examples of the salt with an acid include those derived from inorganic acids such as hydrochloric acid, hydrobromic acid, hydroiodic acid, sulfuric acid, sulfamic acid, phosphoric acid, and nitric acid; and those derived from organic acids such as p-toluenesulfonic acid, salicylic acid, methanesulfonic acid, oxalic acid, succinic acid, citric acid, malic acid, lactic acid, and fumaric acid.

Examples of the salt with a base include those derived from potassium hydroxide, sodium hydroxide, ammonium hydroxide, and quaternary ammonium hydroxide such as tetramethylammonium hydroxide.

The water-soluble prodrugs of the present invention may absorb moisture, adsorb water, or form hydrates when they are left to stand in the atmosphere, and such hydrates are also included in this invention.

Furthermore, the water-soluble prodrugs of the present invention may absorb certain other types of solvents to form solvates, and such solvates are also included in this invention.

Examples of the "amino acid side chain" as used herein include naturally occurring amino acid side chains and non-naturally occurring amino acid side chains.

Examples of the "naturally occurring amino acid side chain" are preferably side chains of naturally occurring amino acids such as a methyl group, isopropyl group, 2-methylpropyl group, 1-methylpropyl group, benzyl group, indol-3-ylmethyl group, 2-(methylthio)ethyl group, 4-aminobutyl group, and 3-aminopropyl group, and more preferably side chains of naturally occurring lipophilic amino acids such as a methyl group, 2-methylpropyl group, benzyl group, and indol-3-ylmethyl group.

Examples of the "non-naturally occurring amino acid side chain" are preferably C5-C12 alkyl groups, cycloalkylmethyl groups, substituted or unsubstituted arylmethyl groups, (cycloalkylthio)methyl groups, and alkylthio-$(CH_2)_r$— in which r is an integer of 1 or 2.

Examples of the "C5-C12 alkyl group" are straight-chain or branched-chain alkyl groups comprising 5 to 12 carbon atoms; and more preferably C8-C12 straight-chain alkyl chains such as an n-octyl group, nonyl group, decyl group, undecyl group, and dodecyl group.

Examples of "alkylthio-$(CH_2)_r$—" are alkylthiomethyl groups or alkylthioethyl groups comprising a straight or branched alkyl chain containing 2 to 10 carbon atoms, such as an ethylthiomethyl group, ethylthioethyl group, n-propylthiomethyl group, n-butylthiomethyl group, n-pentylthiomethyl group, n-octylthiomethyl group, n-nonylthiomethyl group, n-decylthiomethyl group, and tert-butylthiomethyl group; and more preferably an ethylthioethyl group, n-propylthiomethyl group, and n-butylthiomethyl group.

Examples of the "substituted or unsubstituted arylmethyl group" preferably include a 4-phenylbenzyl group, naphtho-2-ylmethyl group, [4-(4-hydroxyphenoxy)phenyl]methyl group, and (4-lower-alkoxyphenyl)methyl group (the term "lower-alkoxy" refers to a straight or branched alkyl chain containing 1 to 6 carbon atoms, and preferred examples include a methoxy group, ethoxy group, propoxy group, butoxy group, and isopropoxy group). The most preferred embodiments of the "substituted or unsubstituted arylmethyl group" include a 4-phenylbenzyl group, naphtho-2-ylmethyl group, (4-methoxyphenyl)methyl group, and [4-(4-hydroxyphenoxy)phenyl]methyl group.

As used herein, the term "active form" refers to a compound that is given by hydrolysis of the water-soluble prodrug, a pharmaceutically acceptable salt thereof, or a hydrate or solvate thereof, and specifically, it refers to compound A1, an ion or salt of compound A1, or the like.

As used herein, the term "camptothecins" [(a) Cancer Chemotherapy and Biotherapy: Principle and Practice, 2nd edition, Lippincott-Ravenmeans, p. 463-484, (b) Biochim. Biophys. Acta (1998), 1400(1-3), 107-119, (c) Expert Opinion, Investig. Drugs (2004) 13(3), pages 269-284] refers to a compound comprising a camptothecin backbone, such as camptothecin, SN-38, 9-aminocamptothecin, 9-nitrocamptothecin, and BN-80915 [Anti-cancer Drugs (2001), 12(1), 9-19] and the camptothecin derivatives described in the above documents.

As used herein, the term "platinum-type anticancer compound" refers to a platinum complex having antitumor effect, and examples include cisplatin (CDDP), carboplatin, oxaliplatin, and nedaplatin.

As used herein, the term "gemcitabine-type compound" refers to a cytidine-type antimetabolite, and examples include gemcitabine and Ara-C. Of the two, gemcitabine is preferred.

As used herein, the term "5-FU-type compound" refers to a fluoropyrimidine-type antimetabolite, and examples include 5-FU (5-fluorouracil), doxifluridine, UFT, carmofur, and S-1. Capecitabine which is a prodrug of 5-FU is also included.

Of these, 5-FU, capecitabine, and doxifluridine are preferred.

Herein, examples of a "taxane-type compound" include Taxol (Front. Biotechnol. Pharm. (2000), 1, 336-348), Taxotere (J. Med. Aromat. Plant Sci. (2001), 22/4A-23/1A4-5), IDN 5109 (Chirality, (2000), 12(⅚), 431-441), BMS 188797 (Clinical Cancer Research. 5 (suppl.), 3859, November 1999), BMS184476 (J. Clinical Oncology 19:2493-2503, 1 May 2001), paclitaxel, and docetaxel.

As used herein, the term "vinca alkaloid-type compound" refers to a type of plant alkaloid, and examples include vinorelbine, vincristine, vinblastine, and vindesine. Of these, vinorelbine is preferred.

As used herein, the term "anticancer tyrosine kinase inhibitor compound" refers to a tyrosine kinase inhibitor compound having anticancer activity, and the term "tyrosine kinase inhibitor compound" refers to a compound that inhibits "tyrosine kinase" which transfers the γ-phosphate group of ATP to the hydroxyl group of a specific tyrosine of a protein. Examples of "anticancer tyrosine kinase inhibitor compounds" include Iressa (gefitinib), and Tarceva (erlotinib).

As used herein, the term "anticancer monoclonal antibody" refers to a monoclonal antibody having anticancer activity, and "monoclonal antibody", also called single-clonal antibody, refers to an antibody produced by a single clone of antibody-producing cells. Examples of "anticancer monoclonal antibodies" include Avastin (bevacizumab), Herceptin (trastuzumab), and Erbitux (cetuximab).

The present invention relates to combination pharmaceuticals comprising compound A and compound B. Specifically, they are cancer therapeutic agents comprising a combination of compound A described below or a pharmaceutically acceptable salt thereof, and compound B described below or a pharmaceutically acceptable salt thereof.

Compound A: Compound A1 represented by formula (1) or the water-soluble prodrug A2 thereof. The active form of the water-soluble prodrug A2 is compound A1.

Compound B: at least one compound selected from the group consisting of: a platinum-type anticancer compound, a gemcitabine-type compound, a 5-FU (5-fluorouracil)-type compound, a taxane-type compound, a vinca alkaloid-type compound, an anticancer tyrosine kinase inhibitor compound, and an anticancer monoclonal antibody.

In the present invention, the phrase "combination cancer therapeutic agents" refers to agents comprising two or more formulations to be administered simultaneously, separately, or successively in therapy, and they may also be pharmaceutical compositions in the form of so-called kit-type formulation or compounded agent.

Agents prepared by further combining one or more formulations to the above-mentioned combination formulations comprising two separate formulations to be used in cancer therapy are also included in the above-mentioned "combination cancer therapeutic agents".

The two separate formulations described above can be further combined with one or more formulations comprising at least one or more compounds selected from the group consisting of a camptothecin, a platinum-type anticancer compound, a gemcitabine-type compound, a 5-FU-type compound, a taxane-type compound, a vinca alkaloid-type compound, an anticancer tyrosine kinase inhibitor compound, and an anticancer monoclonal antibody, or a pharmaceutically acceptable salt thereof, together with pharmaceutically acceptable carriers or diluents. In this case, the further added formulations (one or more) can be administered simultaneously, separately, or successively with the two separate formulations described above. For example, cancer therapeutic agents comprising a combination of three or more compounds are, for example, formulations comprising compounds in the following combinations:

the above-mentioned compound A, a 5-FU-type compound (preferably 5-FU), and leucovorin;

the above-mentioned compound A, a 5-FU-type compound (preferably 5-FU), leucovorin, and Avastin;

the above-mentioned compound A, a 5-FU-type compound (preferably capecitabine), and Avastin;

the above-mentioned compound A, a platinum-type anticancer compound (preferably oxaliplatin), and Avastin;

the above-mentioned compound A, a platinum-type anticancer compound (preferably cisplatin), and 5-FU; and the above-mentioned compound A, a platinum-type anticancer compound (preferably cisplatin), and a taxane-type compound (preferably Taxol).

Of these, examples of preferred combinations are as follows:

the above-mentioned compound A, a 5-FU-type compound (preferably 5-FU), and leucovorin;

the above-mentioned compound A, a 5-FU-type compound (preferably 5-FU), leucovorin, and Avastin;

the above-mentioned compound A, a 5-FU-type compound (preferably capecitabine), and Avastin; and the above-mentioned compound A, a platinum-type anticancer compound (preferably oxaliplatin), and Avastin.

Herein, in the above-mentioned "combination cancer therapeutic agents", one or both of the two separate formulations may be parenteral formulations, preferably injections or drip infusions, and more preferably intravenous drip infusions.

Usually, the "formulations" of the present invention may comprise a therapeutically effective dose of a compound of the present invention together with a pharmaceutically acceptable carrier or diluent. This formulation technique is considered common technical knowledge and well known to those skilled in the art. Preferably, the formulations can be prepared for intravenous drip infusions or injections together with pharmaceutically acceptable carriers or diluents using various methods well known to those skilled in the art.

Furthermore, the term "administer" used herein refers to parenteral administration and/or oral administration when using the "combination cancer therapeutic agents" according to the present invention, and preferably refers to parenteral administration. More specifically, when administering the "combination cancer therapeutic agents", both formulations may be administered parenterally; one may be administered parenterally while the other is administered orally; or both may be administered orally. Preferably, both formulations of the "combination cancer therapeutic agents" are administered parenterally. Herein, "parenteral administration" refers to, for example, intravenous administration, subcutaneous administration, and intramuscular administration, and it is preferably intravenous administration. Furthermore, when three or more formulations are administered in combination, at least one formulation may be administered parenterally, preferably intravenously, and more preferably by intravenous drip infusion or intravenous injection.

When carrying out the present invention, compound A may be administered simultaneously with other anticancer agents such as compound B. Alternatively, other compounds such as compound B may be successively administered after compound A is administered, or compound A may be successively administered after other anticancer agents such as compound B are administered. Furthermore, other anticancer agents may be separately administered some time after compound A is administered, or compound A may be separately administered some time after the other compounds are administered. The order and interval of administration can be appropriately selected by those skilled in the art depending on the formulation comprising compound A of use, formulation comprising the anticancer agent to be used in combination, type of cancer cells to be treated, condition of the patient, and such.

Furthermore, the term "simultaneously" used herein refers to using the agents for treatment at about the same time; and the term "separately" refers to using the agents for treatment separately at different times, for example, use one pharmaceutical agent on the first day and the other pharmaceutical agent for treatment on the second day. The term "successively" refers to using the agents in order; for example, one pharmaceutical agent is used first, and subsequently, after a set period of time, another pharmaceutical agent is used for treatment.

Compound A1

Compound A1 used in the present invention is represented by formula (1) shown below.

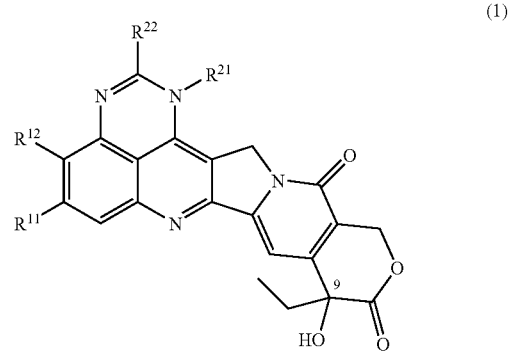

(1)

Herein, $R^{11}$ represents a hydrogen atom, a halogen atom, or a C1-C6 alkyl group.

$R^{12}$ represents a hydrogen atom, a halogen atom, a C1-C6 alkyl group, or a hydroxyl group.

$R^{21}$ represents a hydrogen atom or a C1-C10 alkyl group which may have one to three substituents selected from Group B described below:

Group B: a C1-C6 alkoxy group, a hydroxy group, a halogen atom, an amino group, a mono-C1-C6 alkylamino group, a di-C1-C6 alkylamino group, a C3-C7 cycloalkyl group, a heterocycle, and an aryl ring (the aryl ring may comprise one to three substituents selected from the group consisting of a hydroxy group, a C1-C6 alkoxy group, a halogen atom, an amino group, a mono-C 1-C6 alkylamino group, and a di-C1-C6 alkylamino group).

$R^{22}$ represents a hydrogen atom, an amino group, or a C1-C6 alkyl group that may comprise one to three substituents selected from Group C described below, a C1-C6 alkoxy group that may comprise one to three substituents selected from Group C described below, a C1-C6 alkylthio group that may comprise one to three substituents selected from Group C described below, a mono-C1-C6 alkylamino group that may comprise one to three substituents selected from Group C described below, or a di-C1-C6 alkylamino group that may comprise one to three substituents selected from Group C described below:

Group C: a C1-C6 alkoxy group, a hydroxy group, a halogen atom, an amino group, a C3-C7 cycloalkyl group, a heterocycle, and an aryl ring (the aryl ring may comprise one to three substituents selected from the group consisting of a hydroxy group, a C1-C6 alkoxy group, an amino group, a mono-C 1-C6 alkylamino group, and a di-C1-C6 alkylamino group).

(i) In formula (1), $R^{11}$ mentioned above is preferably a hydrogen atom.

(ii) $R^{12}$ is preferably a hydrogen atom or a C1-C3 alkyl group, and is more preferably a hydrogen atom or methyl group.

(iii) $R^{21}$ is preferably a hydrogen atom, or a C1-C8 alkyl group that may comprise 1 to 3 substituents selected from Group D described below:

Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (the aryl ring may comprise 1 to 3 substituents selected from the group consisting of a hydroxy group, C1-C3 alkoxy group, and halogen atom).

(iv) $R^{21}$ is more preferably a methyl group, ethyl group, n-propyl group, 1-methylethyl group, n-butyl group, 1,1-dimethylethyl group, 2-methylpropyl group, 2,2-dimethylpropyl group, n-pentyl group, 3-methylbutyl group, 2-n-hexyl group, 3,3-dimethylbutyl group, n-heptyl group, n-octyl group, benzyl group, phenethyl group, 2-(dimethylamino)ethyl group, 2-(4-morpholino)ethyl group, 3-(dimethylamino)propyl group, 2-(pyridin-2-yl)ethyl group, 2-(pyridin-3-yl)ethyl group, 2-(4-methoxyphenyl)ethyl group, 2-(4-chlorophenyl)ethyl group, 2-(4-fluorophenyl)ethyl group, or 3-phenylpropyl group.

(v) $R^{22}$ is preferably a hydrogen atom, amino group, C1-C6 alkyl group that may comprise 1 to 3 substituents selected from Group D described below, C1-C6 alkoxy group that may comprise 1 to 3 substituents selected from Group D described below, a C1-C6 alkylthio group that may comprise 1 to 3 substituents selected from Group D described below, a mono-C1-C6 alkylamino group that may comprise 1 to 3 substituents selected from Group D described below, or a di-C1-C6 alkyl amino group that may comprise 1 to 3 substituents selected from Group D described below:

Group D: a C1-C3 alkoxy group, hydroxy group, halogen atom, amino group, mono-C1-C3 alkylamino group, di-C1-C3 alkylamino group, C3-C7 cycloalkyl group, heterocycle, and aryl ring (the aryl ring may comprise 1 to 3 substituents selected from the group consisting of a hydroxy group, C1-C3 alkoxy group, and halogen atom).

(vi) $R^{22}$ is more preferably a hydrogen atom, methyl group, ethyl group, propyl group, hydroxymethyl group, aminomethyl group, (methylamino)methyl group, (dimethylamino) methyl group, chloromethyl group, trifluoromethyl group, phenyl group, 2-pyridyl group, methoxy group, ethoxy group, methylthio group, ethylthio group, methylamino group, butylamino group, or dimethylamino group.

Regarding the above-mentioned (i) to (vi), preferred embodiments can be arbitrarily combined. Examples of the combinations are (i), (ii), (iii), and (v); (i), (ii), (iii), and (vi); (i), (ii), (iv), and (v); and (i), (ii), (iv), and (vi).

More specifically, examples of compound A represented by such formula (1) include the following compounds:

a)
(9S)-1-butyl-9-ethyl-9-hydroxy-1H,12H-pyrano[3",4":6',7'] indolizino[1',2':6,5]pyrido[4,3,2-de]quinazoline-10,13 (9H,15H)-dione;

b)
(9S)-9-ethyl-9-hydroxy-1-[2-(4-morpholino)ethyl]-1H, 12H-pyrano[3",4":6',7']indolizino[1',2': 6,5]pyrido[4,3,2-de]quinazoline-10,13(9H,15H)-dione salt;

c)
(9S)-9-ethyl-9-hydroxy-1-propyl-1H,12H-pyrano[3",4":6', 7']indolizino[1',2':6,5]pyrido[4,3,2-de]quinazoline-10,13 (9H,15H)-dione;

d)
(9S)-1-benzyl-9-ethyl-9-hydroxy-1H,12H-pyrano[3",4":6', 7']indolizino[1',2':6,5]pyrido[4,3,2-de]quinazoline-10,13 (9H,15H)-dione;

e)
(9S)-9-ethyl-9-hydroxy-1-phenethyl-1H,12H-pyrano[3",4": 6',7']indolizino[1',2':6,5]pyrido[4,3,2-de]quinazoline-10, 13(9H,15H)-dione;

f)
(9S)-2,9-diethyl-9-hydroxy-1-phenethyl-1H,12H-pyrano [3",4":6',7']indolizino[1',2':6,5]pyrido[4,3,2-de]quinazoline-10,13(9H,15H)-dione;

g)
(9S)-9-ethyl-9-hydroxy-1-(3-phenylpropyl)-1H,12H-pyrano [3",4":6',7']indolizino[1',2':6,5]pyrido[4,3,2-de]quinazoline-10,13(9H,15H)-dione;

h)
(9S)-9-ethyl-9-hydroxy-1-(3-methylbutyl)-1H,12H-pyrano [3",4":6',7']indolizino[1',2':6,5]pyrido[4,3,2-de]quinazoline-10,13(9H,15H)-dione;

i)
(9S)-2,9-diethyl-9-hydroxy-1-(3-methylbutyl)-1H,12H-pyrano[3",4":6',7']indolizino[1',2':6,5]pyrido[4,3,2-de] quinazoline-10,13(9H,15H)-dione;

j)
(9S)-2,9-diethyl-9-hydroxy-1-(2-methylpropyl)-1H,12H-pyrano[3",4":6',7']indolizino[1',2':6,5]pyrido[4,3,2-de] quinazoline-10,13(9H,15H)-dione;

k)
(9S)-9-ethyl-1-heptyl-9-hydroxy-1H,12H-pyrano[3",4":6', 7']indolizino[1'2':6,5]pyrido[4,3,2-de]quinazoline-10,13 (9H,15H)-dione;

l)
(9S)-9-ethyl-9-hydroxy-1-methyl-1H,12H-pyrano[3",4":6', 7']indolizino[1',2':6,5]pyrido[4,3,2-de]quinazoline-10,13 (9H,15H)-dione;

m)
(9S)-9-ethyl-9-hydroxy-1-(2-methylpropyl)-1H,12H-pyrano[3",4":6',7']indolizino[1',2':6,5]pyrido[4,3,2-de] quinazoline-10,13(9H,15H)-dione;

n)
(9S)-9-ethyl-1-hexyl-9-hydroxy-1H,12H-pyrano[3",4":6',7'] indolizino[1',2':6,5]pyrido[4,3,2-de]quinazoline-10,13 (9H,15H)-dione;

o)
(9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione;

p)
(9S)-1,9-diethyl-9-hydroxy-1H,12H-pyrano[3",4":6',7']indolizino[1',2':6,5]pyrido[4,3,2-de]quinazoline-10,13(9H,15H)-dione;

q)
(9S)-9-ethyl-9-hydroxy-1-[2-(4-methoxyphenyl)ethyl]-1H,12H-pyrano[3",4":6',7']indolizino[1',2':6,5]pyrido[4,3,2-de]quinazoline-10,13(9H,15H)-dione;

r)
(9S)-1-[2-(4-chlorophenyl)ethyl]-9-ethyl-9-hydroxy-1H,12H-pyrano[3",4":6',7']indolizino[1',2':6,5]pyrido[4,3,2-de]quinazoline-10,13(9H,15H)-dione;

s)
(9S)-9-ethyl-1-[2-(4-fluorophenyl)ethyl]-9-hydroxy-1H,12H-pyrano[3",4":6',7']indolizino[1',2':6,5]pyrido[4,3,2-de]quinazoline-10,13(9H,15H)-dione;

t)
(9S)-9-ethyl-1-[2-(4-fluorophenyl)ethyl]-9-hydroxy-2-methyl-1H,12H-pyrano[3",4":6',7']indolizino[1',2':6,5]pyrido[4,3,2-de]quinazoline-10,13(9H,15H)-dione;

u)
(9S)-9-ethyl-9-hydroxy-1-(1-methylethyl)-1H,12H-pyrano[3",4":6',7']indolizino[1',2':6,5]pyrido[4,3,2-de]quinazoline-10,13(9H,15H)-dione;

v)
(9S)-1-(3,3-dimethylbutyl)-9-ethyl-9-hydroxy-1H,12H-pyrano[3",4":6',7']indolizino[1',2':6,5]pyrido[4,3,2-de]quinazoline-10,13(9H,15H)-dione;

w)
(9S)-9-ethyl-9-hydroxy-2-methoxy-1-(3-methylbutyl)-1H,12H-pyrano[3",4":6',7']indolizino[1',2':6,5]pyrido[4,3,2-de]quinazoline-10,13(9H,15H)-dione;

x)
(9S)-2,9-diethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

y)
(9RS)-9-ethyl-9-hydroxy-4-methyl-1-pentyl-1H,12H-pyrano[3",4":6',7']indolizino[1',2':6,5]pyrido[4,3,2-de]quinazoline-10,13(9H,15H)-dione;

z)
(9S)-9-ethyl-9-hydroxy-1-(2-hydroxyethyl)-1H,12H-pyrano[3",4":6',7']indolizino[1',2':6,5]pyrido[4,3,2-de]quinazoline-10,13(9H,15H)-dione;

aa)
(9S)-9-ethyl-9-hydroxy-1-(2-hydroxyethyl)-2-methyl-1H,12H-pyrano[3",4":6',7']indolizino[1',2':6,5]pyrido[4,3,2-de]quinazoline-10,13(9H,15H)-dione;

bb)
(9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione;

cc)
(9S)-2,9-diethyl-9-hydroxy-1-pentyl-1H,12H-pyrano[3",4":6',7']indolizino[1',2':6,5]pyrido[4,3,2-de]quinazoline-10,13(9H,15H)-dione;

dd)
(9S)-9-ethyl-9-hydroxy-1-pentyl-2-propyl-1H,12H-pyrano[3",4":6',7']indolizino[1',2':6,5]pyrido[4,3,2-de]quinazoline-10,13(9H,15H)-dione;

ee)
(9S)-9-ethyl-9-hydroxy-2-hydroxymethyl-1-pentyl-1H,12H-pyrano[3",4":6',7']indolizino[1',2': 6,5]pyrido[4,3,2-de]quinazoline-10,13(9H,15H)-dione;

ff)
(9S)-9-ethyl-9-hydroxy-2-hydroxymethyl-1-(2-methylpropyl)-1H,12H-pyrano[3",4":6',7']indolizino[1',2':6,5]pyrido[4,3,2-de]quinazoline-10,13(9H,15H)-dione;

gg)
(9S)-9-ethyl-9-hydroxy-2-hydroxymethyl-1-(3-methylbutyl)-1H,12H-pyrano[3",4":6',7']indolizino[1',2':6,5]pyrido[4,3,2-de]quinazoline-10,13(9H,15H)-dione;

hh)
(9S)-2-chloromethyl-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione;

ii)
(9S)-2-aminomethyl-9-ethyl-9-hydroxy-1-pentyl-1H,12H-pyrano[3",4":6',7']indolizino[1',2':6,5]pyrido[4,3,2-de]quinazoline-10,13(9H,15H)-dione;

jj)
(9S)-9-ethyl-9-hydroxy-1-pentyl-2-trifluoromethyl-1H,12H-pyrano[3",4":6',7']indolizino[1',2':6,5]pyrido[4,3,2-de]quinazoline-10,13(9H,15H)-dione;

kk)
(9S)-9-ethyl-9-hydroxy-1-(3-methylbutyl)-2-methylthio-1H,12H-pyrano[3",4":6',7']indolizino[1',2':6,5]pyrido[4,3,2-de]quinazoline-10,13(9H,15H)-dione;

ll)
(9S)-9-ethyl-2-ethylthio-9-hydroxy-1-(3-methylbutyl)-1H,12H-pyrano[3",4":6',7']indolizino[1',2':6,5]pyrido[4,3,2-de]quinazoline-10,13(9H,15H)-dione;

mm)
(9S)-2-(dimethylamino)-9-ethyl-9-hydroxy-1-(2-methylpropyl)-1H,12H-pyrano[3",4":6',7']indolizino[1',2':6,5]pyrido[4,3,2-de]quinazoline-10,13(9H,15H)-dione hydrochloride; and nn)
(9S)-2-(butylamino)-9-ethyl-9-hydroxy-1-(3-methylbutyl)-1H,12H-pyrano[3",4":6',7']indolizino[1',2':6,5]pyrido[4,3,2-de]quinazoline-10,13(9H,15H)-dione hydrochloride.

Among compounds A1 indicated above, particularly preferred examples are the following compounds:
4(S)-ethyl-4-hydroxy-1H-pyrano[3',4':6,7]indolizino[1,2-b]quinoline-3,14(4H,12H)-dione(camptothecin);
5(R)-ethyl-9,10-difluoro-1,4,5,13-tetrahydro-5-hydroxy-3H,15H-oxepino[3',4':6,7]indolizino[1,2-b]quinoline-3,15-dione (BN-80915);

o)
(9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione;

bb)
(9S)-9-ethyl-9-hydroxy-2-methyl-1-pentyl-1H,12H-pyrano[3",4":6',7']indolizino[1',2':6,5]pyrido[4,3,2-de]quinazoline-10,13(9H,15H)-dione; and ee)
(9S)-9-ethyl-9-hydroxy-2-hydroxymethyl-1-pentyl-1H,12H-pyrano[3",4":6',7']indolizino[1',2':6,5]pyrido[4,3,2-de]quinazoline-10,13(9H,15H)-dione.

Of the compounds of A1 indicated above, the following compound is particularly preferred:

o)
(9S)-9-ethyl-9-hydroxy-1-pentyl-1H,12H-pyrano[3",4",6',7']indolizino[1',2':6,5]pyrido[4,3,2-de]quinazolin-10,13(9H,15H)-dione.

Water-Soluble Prodrug A2

Water-soluble prodrug A2 included in the present invention is a water-soluble prodrug of compound A1 mentioned above.

Examples of the aforementioned water-soluble prodrug A2 of A1 are preferably prodrug compounds represented by formula (2) shown below.

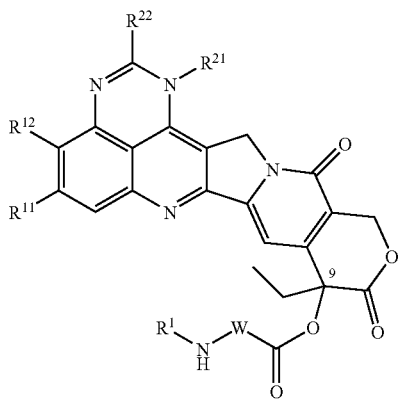

(2)

Herein, $R^{11}$, $R^{12}$, $R^{21}$, and $R^{22}$ are as defined for compound A1, and preferred embodiments thereof are also the same.

$R^1$ represents a hydrogen atom or a C1-C6 alkyl group; and W represents a divalent group comprising a secondary amino group, a divalent group comprising a tertiary amino group, or a divalent group comprising a sulfonyl group.

Preferred examples of the compounds represented by formula (2) are prodrug compounds represented by formula (3) shown below.

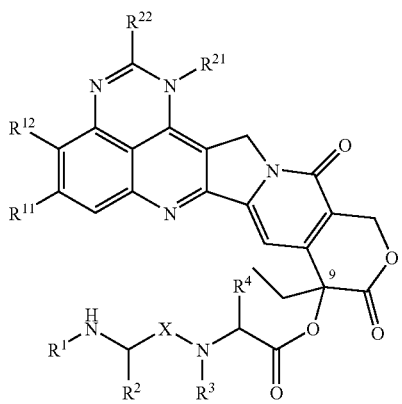

(3)

Herein, $R^{11}$, $R^{12}$, $R^{21}$, and $R^{22}$ are as defined for compound A1, and the preferred embodiments are also the same. Preferred active forms for the prodrug of formula (3) are also the same as the preferred embodiments of compound A1 mentioned above.

$R^1$ represents a hydrogen atom or a C1-C6 alkyl group.

$R^2$ and $R^4$ individually represent a hydrogen atom, a C1-C6 alkyl group, or an amino acid side chain, $R^3$ represents a C1-C6 alkyl group, and X represents C=O or a C1-C3 alkylene group.

In prodrug compounds represented by formula (3) above, $R^1$ mentioned above is preferably a hydrogen atom, a methyl group, or an ethyl group, more preferably a hydrogen atom or a methyl group, and particularly preferably a hydrogen atom.

The aforementioned $R^2$ is preferably a hydrogen atom or a methyl group.

The aforementioned $R^3$ is preferably a C1-C3 alkyl group, more preferably a methyl group or an ethyl group, and particularly preferably a methyl group.

The aforementioned $R^4$ is preferably a hydrogen atom or a methyl group.

The aforementioned X is preferably a carbonyl group or a methylene group, and more preferably a carbonyl group.

Examples of preferred combinations of X and $R^1$ to $R^4$ which constitute the solubilizing side chain portion of compounds represented by formula (3) are shown below, but the present invention is not limited thereto.

TABLE 1

|    | $R^1$     | $R^2$       | $R^3$     | $R^4$       | X       |
|----|-----------|-------------|-----------|-------------|---------|
| 1  | H         | H OR —CH$_3$ | —CH$_3$   | H OR —CH$_3$ | C=O     |
| 2  | H         | H OR —CH$_3$ | —C$_2$H$_5$ | H OR —CH$_3$ | C=O     |
| 3  | —CH$_3$   | H OR —CH$_3$ | —CH$_3$   | H OR —CH$_3$ | C=O     |
| 4  | —CH$_3$   | H OR —CH$_3$ | —C$_2$H$_5$ | H OR —CH$_3$ | C=O     |
| 5  | —C$_2$H$_5$ | H OR —CH$_3$ | —CH$_3$   | H OR —CH$_3$ | C=O     |
| 6  | —C$_2$H$_5$ | H OR —CH$_3$ | —C$_2$H$_5$ | H OR —CH$_3$ | C=O     |
| 7  | H         | H OR —CH$_3$ | —CH$_3$   | H OR —CH$_3$ | —CH$_2$— |
| 8  | H         | H OR —CH$_3$ | —C$_2$H$_5$ | H OR —CH$_3$ | —CH$_2$— |
| 9  | —CH$_3$   | H OR —CH$_3$ | —CH$_3$   | H OR —CH$_3$ | —CH$_2$— |
| 10 | —CH$_3$   | H OR —CH$_3$ | —C$_2$H$_5$ | H OR —CH$_3$ | —CH$_2$— |
| 11 | —C$_2$H$_5$ | H OR —CH$_3$ | —CH$_3$   | H OR —CH$_3$ | —CH$_2$— |
| 12 | —C$_2$H$_5$ | H OR —CH$_3$ | —C$_2$H$_5$ | H OR —CH$_3$ | —CH$_2$— |

Compounds of formula (3) are preferably, for example, compounds comprising the solubilizing side chain included in reference number 1, 2, 3, or 4 in Table 1, and more preferably, for example, compounds comprising the solubilizing side chain included in reference number 1 or 2 in Table 1.

If such a solubilizing side chain is present, even if compound A1 is a poorly soluble compound, it can be made into a compound having good water solubility. In addition, for example, the water-soluble prodrug can exist stably for a long period of time in a solution at pH4 or lower; however, under physiological conditions of pH5 or higher, in particular, pH7 to 8, the active form (such as compound A1) can be rapidly and quantitatively dissociated within a short period of time.

The anticancer effect of such water-soluble prodrugs remarkably increases when the prodrugs are combined with specific anticancer compound B.

Further, more preferable examples of prodrug compounds for the compounds represented by formula (2) are compounds represented by formula (4) described below.

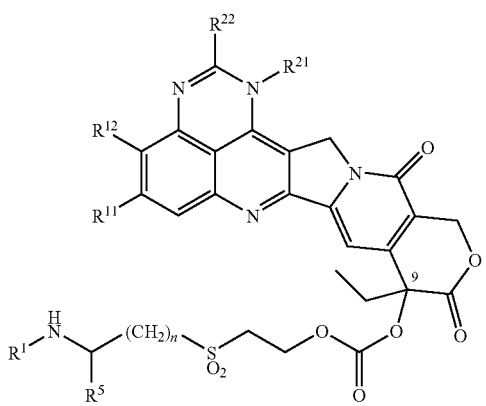

(4)

Herein, $R^{11}$, $R^{12}$, $R^{21}$, and $R^{22}$ are as defined for compound A1, and the preferred embodiments are also the same. Preferred active forms for the prodrug of formula (4) are also the same as the preferred embodiments of compound A1 mentioned above.

$R^1$ represents a hydrogen atom or a C1-C6 alkyl group.

$R^5$ represents a hydrogen atom or —COOR$^6$ (wherein, $R^6$ represents a hydrogen atom or a C1-C6 alkyl group). n represents an integer of 1 to 6.

In the compounds represented by the aforementioned formula (4), the aforementioned $R^1$ is preferably a hydrogen atom, a methyl group, or an ethyl group, more preferably a hydrogen atom or a methyl group, and particularly preferably a hydrogen atom.

In formula (4), n is preferably 1 to 3, and more preferably 1.

When n is 1, $R^5$ is preferably a hydrogen atom or —COOR$^6$ ($R^6$ is a C1-C3 alkyl group), and more preferably a hydrogen atom, —COOCH$_3$, or —COOC$_2$H$_5$.

When n is 2 to 6, $R^5$ is preferably a hydrogen atom.

Examples of preferred combinations of n, $R^1$, and $R^5$ which constitute the solubilizing side chain portion of compounds represented by formula (4) are shown below, but the present invention is not limited thereto.

TABLE 2

|    | $R^1$    | n | $R^5$       |
|----|----------|---|-------------|
| 1  | H        | 1 | H           |
| 2  | H        | 1 | —CO$_2$CH$_3$ |
| 3  | H        | 1 | —CO$_2$C$_2$H$_5$ |
| 4  | —CH$_3$  | 1 | H           |
| 5  | —CH$_3$  | 1 | —CO$_2$CH$_3$ |
| 6  | —CH$_3$  | 1 | —CO$_2$C$_2$H$_5$ |
| 7  | —C$_2$H$_5$ | 1 | H        |
| 8  | —C$_2$H$_5$ | 1 | —CO$_2$CH$_3$ |
| 9  | —C$_2$H$_5$ | 1 | —CO$_2$C$_2$H$_5$ |
| 10 | H        | 2 | H           |
| 11 | H        | 2 | —CO$_2$CH$_3$ |
| 12 | H        | 2 | —CO$_2$C$_2$H$_5$ |
| 13 | —CH$_3$  | 2 | H           |
| 14 | —CH$_3$  | 2 | —CO$_2$CH$_3$ |
| 15 | —CH$_3$  | 2 | —CO$_2$C$_2$H$_5$ |
| 16 | —C$_2$H$_5$ | 2 | H        |
| 17 | —C$_2$H$_5$ | 2 | —CO$_2$CH$_3$ |
| 18 | —C$_2$H$_5$ | 2 | —CO$_2$C$_2$H$_5$ |
| 19 | H        | 3 | H           |
| 20 | H        | 3 | —CO$_2$CH$_3$ |
| 21 | H        | 3 | —CO$_2$C$_2$H$_5$ |
| 22 | —CH$_3$  | 3 | H           |
| 23 | —CH$_3$  | 3 | —CO$_2$CH$_3$ |

TABLE 2-continued

|    | $R^1$    | n | $R^5$       |
|----|----------|---|-------------|
| 24 | —CH$_3$  | 3 | —CO$_2$C$_2$H$_5$ |
| 25 | —C$_2$H$_5$ | 3 | H        |
| 26 | —C$_2$H$_5$ | 3 | —CO$_2$CH$_3$ |
| 27 | —C$_2$H$_5$ | 3 | —CO$_2$C$_2$H$_5$ |

Compounds of formula (4) are preferably, for example, compounds comprising the solubilizing side chain included in reference number 1, 2, 3, 4, 5, or 6 in Table 2, and more preferably, for example, compounds comprising the solubilizing side chain included in reference number 1, 3, or 4 in Table 2.

If such a solubilizing side chain is present, even if compound A1 is a poorly soluble compound, it can be made into a compound having good water solubility. In addition, for example, the water-soluble prodrug can exist stably for a long period of time in a solution at pH4 or lower; however, under physiological conditions of pH5 or higher, in particular, pH7 to 8, the active form (such as compound A1) can be rapidly and quantitatively dissociated within a short period of time.

The anticancer effect of such water-soluble prodrugs remarkably increases when the prodrugs are combined with specific anticancer compound B.

Further, more preferable examples of prodrug compounds for the compounds represented by formula (2) are compounds represented by formula (5) described below.

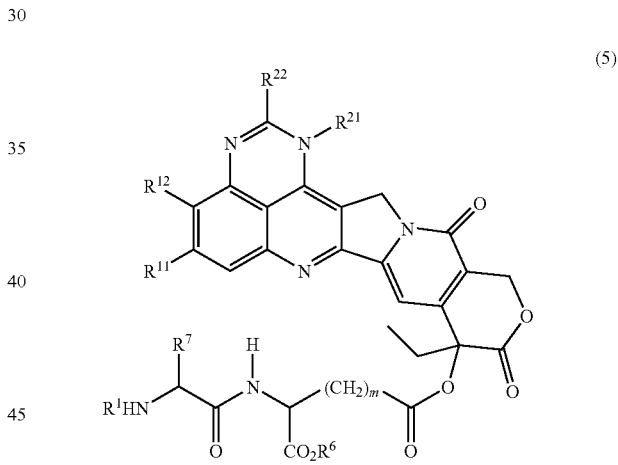

(5)

Herein, $R^{11}$, $R^{12}$, $R^{21}$, and $R^{22}$ are as defined for compound A1, and the preferred embodiments are also the same. Preferred active forms for the prodrug of formula (5) are also the same as the preferred embodiments of compound A1 mentioned above.

$R^1$ represents a hydrogen atom or a C1-C6 alkyl group. $R^6$ represents a hydrogen atom, a branched C3-C10 alkyl group, or a C3-C8 cycloalkyl group. $R^7$ is a naturally occurring or non-naturally occurring amino acid side chain. m is an integer of 1 to 3.

$R^1$ is preferably a hydrogen atom.

$R^6$ is preferably a hydrogen atom.

$R^7$ is preferably 2-methylpropyl, cyclohexylmethyl, benzyl, indol-3-ylmethyl, 4-aminobutyl, or 4-aminopropyl, or more preferably 2-methylpropyl, cyclohexylmethyl, benzyl, or indol-3-ylmethyl.

If such a solubilizing side chain is present, even if compound A1 is a poorly soluble compound, it can be made into a compound having good water solubility. In addition, for example, the water-soluble prodrug can exist stably for a long period of time in a solution at pH4 or lower; however, under physiological conditions of pH5 or higher, in particular, pH7 to 8, the active form (such as compound A1) can be rapidly and quantitatively dissociated within a short period of time.

The anticancer effect of such water-soluble prodrugs remarkably increases when the prodrugs are combined with specific anticancer compound B.

Examples of water-soluble prodrug A2 of the present invention are preferably compounds represented by the above-mentioned formulas (3) to (5), more preferably compounds represented by the above-mentioned formula (3) or (4), and particularly preferably compounds represented by the above-mentioned formula (3).

Compound B

Examples of compound B used in the present invention include at least one compound selected from the group consisting of a platinum-type anticancer compound, a gemcitabine-type compound, a 5-FU-type compound, a taxane-type compound, a vinca alkaloid-type compound, an anticancer tyrosine kinase inhibitor compound, and an anticancer monoclonal antibody.

For compound B used in the present invention, a platinum-type anticancer compound is preferred.

Therapeutic Agents for Cancer

The present invention relates to combination pharmaceuticals comprising the aforementioned compound A and compound B. Specifically, they are cancer therapeutic agents comprising combination of the aforementioned compound A, or a pharmaceutically acceptable salt thereof, and the aforementioned compound B, or a pharmaceutically acceptable salt thereof.

When compound A and compound B are used in combination as described above, the anticancer effects increase remarkably.

Examples of the aforementioned therapeutic agents for cancer are preferably therapeutic agents for cancer in which the aforementioned compound A is compound A1 described above and the aforementioned compound B is a platinum-type anticancer compound.

In another preferred embodiment of the aforementioned therapeutic agent for cancer, for example, the aforementioned compound A is the aforementioned water-soluble prodrug A2 of compound A1, and the aforementioned compound B is at least one compound selected from the group consisting of a platinum-type anticancer compound, a gemcitabine-type compound, a 5-FU-type compound, a taxane-type compound, a vinca alkaloid-type compound, an anticancer tyrosine kinase inhibitor compound, and an anticancer monoclonal antibody, or preferably one compound selected from the group consisting of a platinum-type anticancer compound, a gemcitabine-type compound, and a 5-FU-type compound.

More preferable examples are cancer therapeutic agents in which the aforementioned compound A is the aforementioned water-soluble prodrug A2 and the aforementioned compound B is a platinum-type anticancer compound.

When compound A and compound B are combined this way, the anticancer effects become more pronounced.

The preferred embodiments and specific embodiments of the aforementioned compound A1, water-soluble prodrug A2, and compound B in the therapeutic agents for cancer are as described above.

The following are preferred embodiments of the combination of compound A and compound B mentioned above by the cancer type:

lung cancer: the aforementioned compound A1 and a platinum-type anticancer compound (preferably cisplatin);

lung cancer: the aforementioned water-soluble prodrug A2 and a platinum-type anticancer compound (preferably cisplatin and carboplatin);

stomach cancer: the aforementioned compound A1 and a platinum-type anticancer compound (preferably cisplatin);

stomach cancer: the aforementioned water-soluble prodrug A2, a 5-FU-type compound (preferably capecitabine), and a platinum-type anticancer compound (preferably cisplatin and carboplatin);

colorectal cancer: the aforementioned water-soluble prodrug A2 and a 5-FU-type compound (preferably capecitabine);

rectal cancer: the aforementioned water-soluble prodrug A2 and a platinum-type anticancer compound (preferably oxaliplatin);

pancreatic cancer: the aforementioned water-soluble prodrug A2 and a gemcitabine-type compound (preferably gemcitabine);

breast cancer: the aforementioned water-soluble prodrug A2 and a 5-FU-type compound (preferably capecitabine); and ovarian cancer: the aforementioned compound A1 and a platinum-type anticancer compound (preferably cisplatin).

The cancer therapeutic agents of the present invention may be a compounded agent comprising compound A and compound B, or they may be kits comprising a formulation comprising compound A and a formulation comprising compound B. In these kits, compound A and compound B are administered separately.

Methods for Producing the Compounds

Compounds represented by formula (1) which are used in the present invention may be, for example, commercially available products or can be obtained by known methods (for example, WO 03/045952 and WO 03/043631).

Compounds represented by formula (2) and particularly formula (5) which are used in the present invention may be, for example, commercially available products or can be obtained by known methods (for example, WO 03/043631).

Compounds represented by formula (2) and particularly formulas (3) and (4) which are used in the present invention can be produced, for example, according to the methods described below. Starting material compounds used for the production may be commercially available compounds or may be produced by standard methods, as necessary.

In the production methods shown below, $R^1$, $R^2$, $R^3$, $R^4$, X, $R^5$, and n have the same meaning as $R^1$, $R^2$, $R^3$, $R^4$, X, $R^5$, and n, respectively, defined in formulas (2), (3), and (4). Furthermore, $P^1$ represents an amino protecting group, $P^2$ represents a carbonylating agent residue, and Hal represents a halogen atom (a chlorine atom, a bromine atom, or an iodine atom). Y represents a hydroxyl group residue at position 9 in compound A1 (Y—OH). $R^8$ represents a halogen atom or a group represented by $OR^9$. $R^9$ represents a hydrogen atom or a C1-C6 alkyl group.

Reaction Process 1-1

Y-OH + 1a → 2a

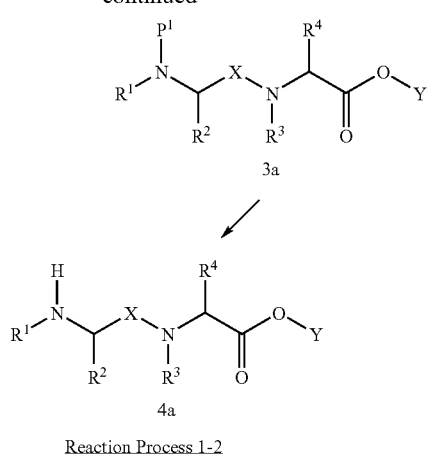

3a

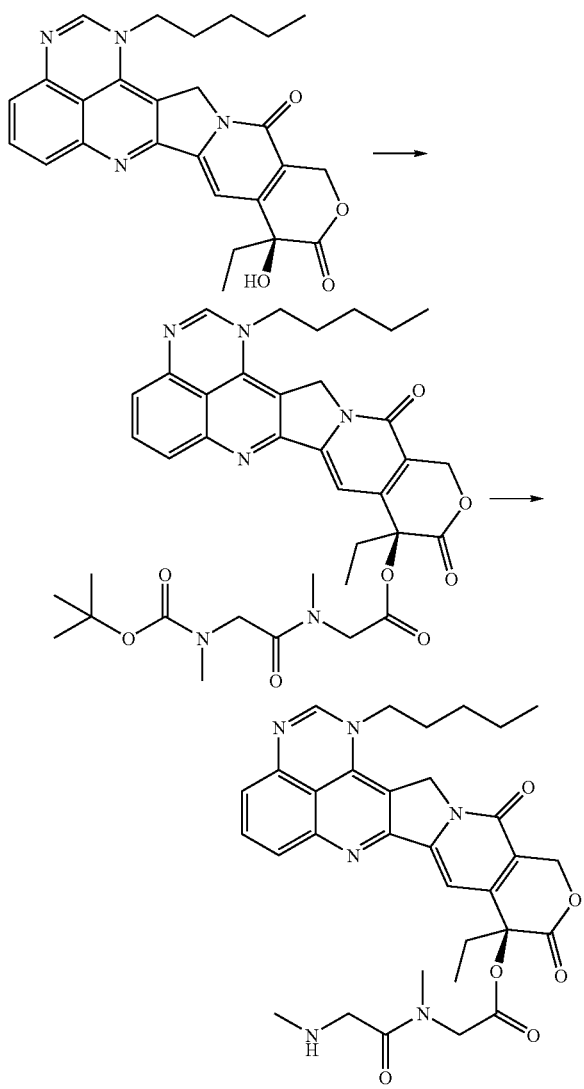

Reaction Process 1-2

<Reaction Process 1>

Reaction Processes 1-1 and 1-2 show an example of the production of a water-soluble prodrug comprising a tertiary amino group in its solubilizing side chain, which is represented by the aforementioned formula (3).

The water-soluble prodrug represented by the aforementioned formula (3) can be obtained easily by, for example, acylation of the hydroxyl group on position 9 of compound A1 of formula (1).

Preparation of Compound 3a

As indicated in Reaction Process 1-1, ester (3a) can be obtained by reacting compound A1 (1a) with a corresponding compound (2a) in an appropriate solvent, in the presence of a coupling agent. Examples of compound 2a include a carboxylic acid ($R^8$=OH), a carboxylate ester ($R^8$=$OR^9$), and a acyl halide compound ($R^8$=halogen atom (chlorine atom or such)), with carboxylic acid being the preferred one.

When compound (2a) is a dipeptide (X=CO) carboxylic acid, or a peptide derivative (X=$CH_2$), the amino acid derivative used to prepare such a compound (2a) is commercially available, or it can be prepared by known methods described in the literature (for example, J. Am. Chem. Soc. 2000, 122, 762-766; J. Org. Chem., 1998, 5240; Tetrahedron Asymmetry, 1995, 1741; Tetrahedron Asymmetry, 1998, 4249). The carboxylic acid can be converted into a carboxylate ester ($R^8$=$OR^9$) or a acyl halide compound ($R^8$=halogen atom) by known methods.

Furthermore, the dipeptide derivative can be prepared by standard peptide chemistry well known to those skilled in the art (see, "The Practice of Peptide Synthesis" by M. Bodansky and A. Bodansky, 2nd edition, 1994 (Springer-Verlag)).

Examples of solvents used in the above coupling reaction include methylene chloride, ethyl acetate, tetrahydrofuran, acetonitrile, chloroform, dioxane, and dimethylformamide.

Examples of the coupling agents include 1-ethyl-3-(3-dimethylaminopropyl)-carbodiimide hydrochloride, dicyclohexylcarbodiimide, BOP, HBTU, TNTU, PyBroP™, PyBOP™, TBTU, TSTU, and HOBt (see, The Combinatorial Chemistry Catalog, February, 1997; Novabiochem., for commercially available coupling reagents).

Preparation of Compound 4a

While preparation of compound 4a depends on the type of the corresponding carboxylic acid, a corresponding carboxylic acid (2a) with a protected amino group is usually preferred. The coupling reaction is followed by removal of the protecting group from compound (3a), to give the water-soluble prodrug represented by compound (4a).

The obtained water-soluble prodrug comprising an amino protecting group is deprotected, for example, as shown in Process 1-2.

The coupling reaction and selection of the amino protecting group $P^1$ in Processes 1-1 and 1-2 can be performed suitably using known methods (see, "The Practice of Peptide Synthesis" by M. Bodansky and A. Bodansky, 2nd edition, 1994 (Springer-Verlag); "Protective Groups in Organic Synthesis" by Theodora Greene, 1999 (Wiley-Interscience)).

Examples of amino protecting groups include the following:

Carbamate-Types a methyloxycarbonyl group, 9-fluorenylmethyloxycarbonyl group, 9-(2-sulfo)fluorenylmethyloxycarbonyl group, 9-(2,7-dibromo)fluorenylmethyloxycarbonyl group, 4-methoxyphenacyloxycarbonyl group, ethyloxycarbonyl group, 2,2,2-trichloroethyloxycarbonyl group, 2-trimethylsilylethyloxycarbonyl group, phenethyloxycarbonyl group, 1-(1-adamantyl)-1-methylethyloxycarbonyl group, 2-chloroethyloxycarbonyl group, 2-bromoethyloxycarbonyl group, 2-iodoethyloxycarbonyl group, 2,2-dichloroethyloxycarbonyl group, 2,2-dibromoethyloxycarbonyl group, 2,2,2-trichloroethyloxycarbonyl group, 2,2,2-tribromoethyloxycarbonyl group, 1,1-dimethyl-2-chloroethyloxycarbonyl group, 1,1-dimethyl-2-bromoethyloxycarbonyl group, 1,1- dimethyl-2,2-dibromoethyloxycarbonyl group, 1,1-dimethyl-2,2,2-trichloroethyloxycarbonyl group, 1-methyl-1-(4-biphenylyl)ethyloxycarbonyl group, 1-(3,5-di t-butylphenyl)-1-methylethyloxycarbonyl group, 2-(2'-pyridyl)ethyloxycarbonyl group, 2-(4'-pyridyl)ethyloxycarbonyl group, 2-(N,N-dicyclohexylcarboxamide) ethyloxycarbonyl group, t-butyloxycarbonyl group, 1-adamantyloxycarbonyl group, vinyloxycarbonyl group, allyloxycarbonyl group, 1-isopropylallyloxycarbonyl group, cinnamyloxycarbonyl group, 4-nitrocinnamyloxycarbonyl group, 8-quinolyloxycarbonyl group, piperidinyloxycarbonyl group, benzyloxycarbonyl group, p-methoxybenzyloxycarbonyl group, p-nitrobenzyloxycarbonyl group, p-chlorobenzyloxycarbonyl group, p-bromobenzyloxycarbonyl group, p-cyanobenzyloxycarbonyl group, o-nitrobenzyloxycarbonyl group, 2,4-dichlorobenzyloxycarbonyl group, 4-methylsulfinylbenzyloxycarbonyl group, 9-anthrylmethyloxycarbonyl group, diphenylmethyloxycarbonyl group, 2-methylthioethyloxycarbonyl group, 2-methylsulfonylethyloxycarbonyl group, 2-(p-toluenesulfonyl)ethyloxycarbonyl group, [2-(1,3-dithianyl)]methyloxycarbonyl group, 4-methylthiophenyloxycarbonyl group, 2,4-dimethylthiophenyloxycarbonyl group, 2-phosphinoethyloxycarbonyl group, 2-triphenylphosphonioisopropyloxycarbonyl group, 1,1-dimethyl-2-cyanoethyloxycarbonyl group, m-chloro-p-acetylbenzyloxycarbonyl group, p-(dihydroxyboryl)benzyloxycarbonyl group, 5-benzisoxazolylmethyloxycarbonyl group, 2-(trifluoromethyl)-6-chromonylmethyloxycarbonyl group, m-nitrophenyloxycarbonyl group, 3,5-dimethoxybenzyloxycarbonyl group, 3,4-dimethoxy-6-nitrobenzyloxycarbonyl group, and phenyl(o-nitrophenyl)methyloxycarbonyl group;

Urea Types a piperidinylcarbonyl group, p-toluenesulfonylaminocarbonyl group, and phenylaminothiocarbonyl group;

Others a t-amyloxycarbonyl group, benzylthiocarbonyl group, cyclobutyloxycarbonyl group, cyclopentyloxycarbonyl group, cyclohexyloxycarbonyl group, cyclopropylmethyloxycarbonyl group, p-decyloxybenzyloxycarbonyl group, diisopropylmethyloxycarbonyl group, 2,2-dimethoxycarbonylvinyloxycarbonyl group, o-(N,N-dimethylcarboxamide) benzyloxycarbonyl group, 1,1-dimethyl-3-(N,N-dimethylcarboxamide)propyloxycarbonyl group, 1,1-dimethylpropynyloxycarbonyl group, di(2-pyridyl) methyloxycarbonyl group, 2-furanylmethyloxycarbonyl group, isobornyloxycarbonyl group, isobutyloxycarbonyl group, isonicotinyloxycarbonyl group, p-(p'-methoxyphenylazo)benzyloxycarbonyl group, 1-methylcyclobutyloxycarbonyl group, 1-methylcyclohexyloxycarbonyl group, 1-methyl-1-cyclopropylmethyloxycarbonyl group, 1-methyl-1-(3,5-dimethoxyphenyl)ethyloxycarbonyl group, 1-methyl-1-(p-phenylazophenyl)ethyloxycarbonyl group, 1-methyl-1-phenylethyloxycarbonyl group, 1-methyl-1-(4-pyridyl) ethyloxycarbonyl group, p-(phenylazo)benzyloxycarbonyl group, 2,4,6-tri-t-butylphenyloxycarbonyl group, 4-(trimethylammonium)benzyloxycarbonyl group, and 2,4,6-trimethylbenzyloxycarbonyl group; and Amide-Types a formyl group, acetyl group, chloroacetyl group, trichloroacetyl group, trifluoroacetyl group, phenylacetyl group, 3-phenylpropionyl group, picolinoyl group, benzoyl group, p-phenylbenzoyl group, o-nitrophenylacetyl group, o-nitrophenoxyacetyl group, acetoacetyl group, (N-dithiobenzyloxycarbonylamino)acetyl group, 3-(p-hydroxyphenyl)propionyl group, 3-(o-nitrophenyl)propionyl group, 2-methyl-2-(o-nitrophenoxy)propionyl group, 2-methyl-2-(o-phenylazophenoxy)propionyl group, 4-chlorobutyryl group, 3-methyl-3-nitrobutyryl group, o-nitrocinnamoyl group, o-nitrobenzoyl group, and o-(benzoyloxymethyl)benzoyl group.

Removal of the amino protecting group after a coupling reaction can be performed by methods well known to those skilled in the art, such as reacting trifluoroacetic acid for the removal of a Boc group, piperidine for the removal of an Fmoc group, and tetrabutylammonium fluoride for the removal of 2-(trimethylsilyl)ethoxycarbonyl (Teoc), trimethylsilylethyl and ter-butyldimethylsilyl groups, and using catalytic hydrogenation for the removal of a Cbz group.

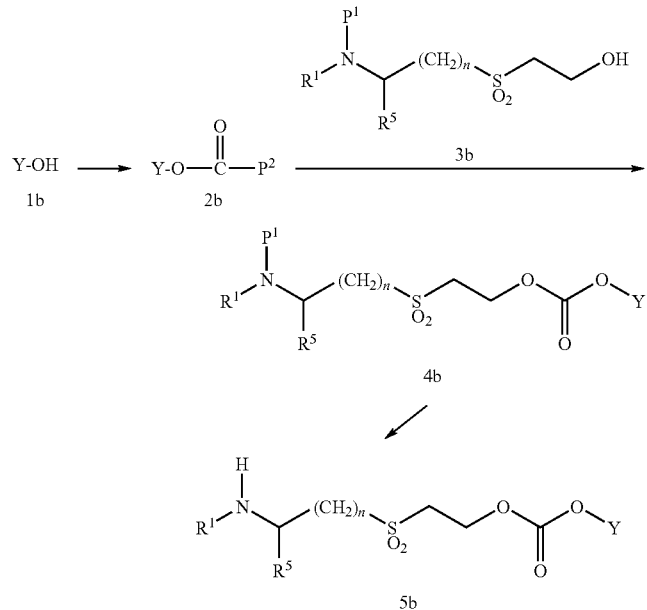

Reaction Process 2-1

-continued

Reaction Process 2-2

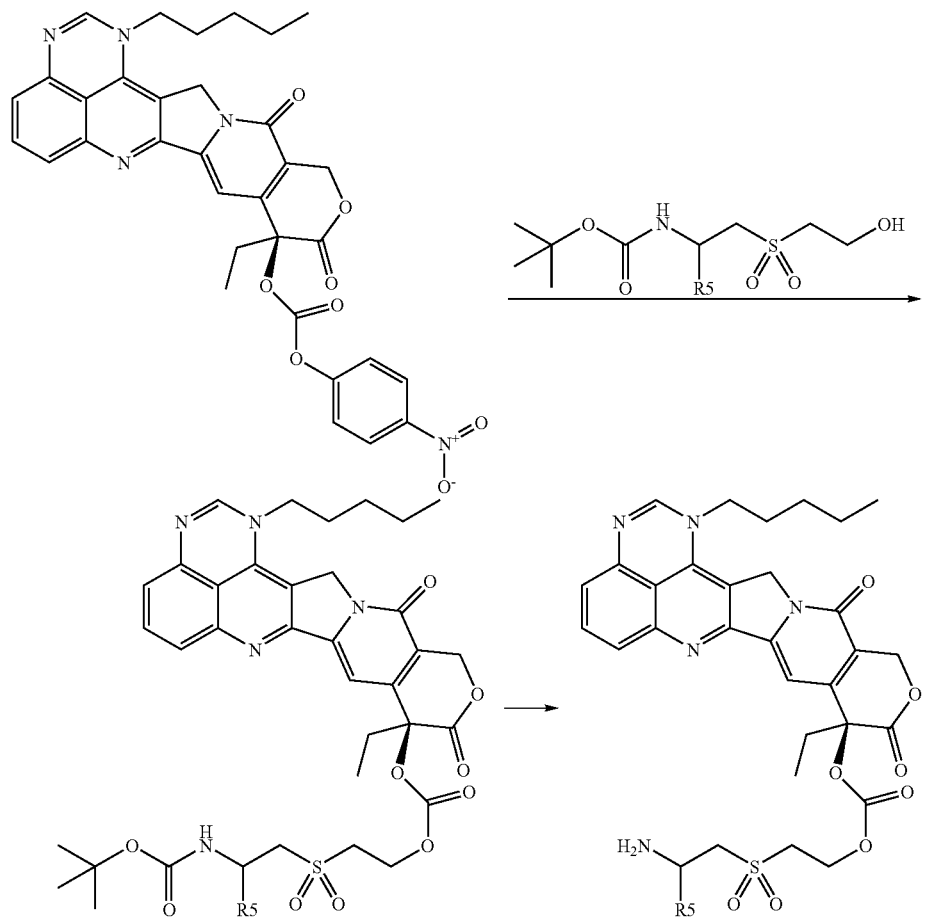

<Reaction Process 2>

Reaction Processes 2-1 and 2-2 show an example of the method for producing water-soluble prodrugs whose solubilizing side chain comprises a sulfonyl group, which are represented by the aforementioned formula (4).

Preparation of Compound 2b

First, alcohol (1b) is carbonylated to produce compound (2b). Carbonylation of the hydroxyl group is accomplished by reacting alcohol (1b) with an appropriate carbonylating agent in an appropriate solvent.

Examples of a solvent that may be used include methylene chloride, ethyl acetate, tetrahydrofuran, acetonitrile, chloroform, dioxane, and dimethylformamide.

Examples of a carbonylating agent that may be used include p-nitrophenyl chloroformate, carbonyldiimidazole, and phosgenes.

Usually, the reaction can be performed at −10° C. to 25° C., for 1 to 24 hours.

Preparation of Compound 3b

Compound 3b comprising a solubilizing side chain can be prepared by a known method (Tetrahedron (1999), 55: 6623-6634).

Protection of the amino group in alcohol (3b) can be performed suitably using known methods (see, The Practice of Peptide Synthesis, M. Bodansky, and A. Bodansky/2nd edition, 1994 (Springer-Verlag)).

Preparation of Compound 4b

Next, alcohol (3b) comprising a corresponding protected amino group can be reacted with carbonylated compound (2b) in the presence of an appropriate solvent to give an amino-group-protected carbonate (4b).

Examples of a solvent that may be used include methylene chloride, ethyl acetate, tetrahydrofuran, acetonitrile, chloroform, dioxane, and dimethylformamide.

Usually, the reaction can be performed at 15° C. to 25° C., for 2 to 48 hours.

Preparation of Compound 5b

By removing the amino protecting group of carbonate (4b) by known methods, compound (5b) can be obtained. Removal of the amino group can be performed using known methods, as in the above-described Reaction Process 1. Examples include reacting trifluoroacetic acid for the removal of a Boc group, piperidine for the removal of an Fmoc group, and tetrabutylammonium fluoride for the removal of 2-(trimethylsilyl)ethoxycarbonyl (Teoc), trimethylsilylethyl and ter-butyldimethylsilyl groups, and using catalytic hydrogenation for the removal of a Cbz group.

Reaction Process 2-2 described above shows a specific example of such.

Reaction Process 3-1
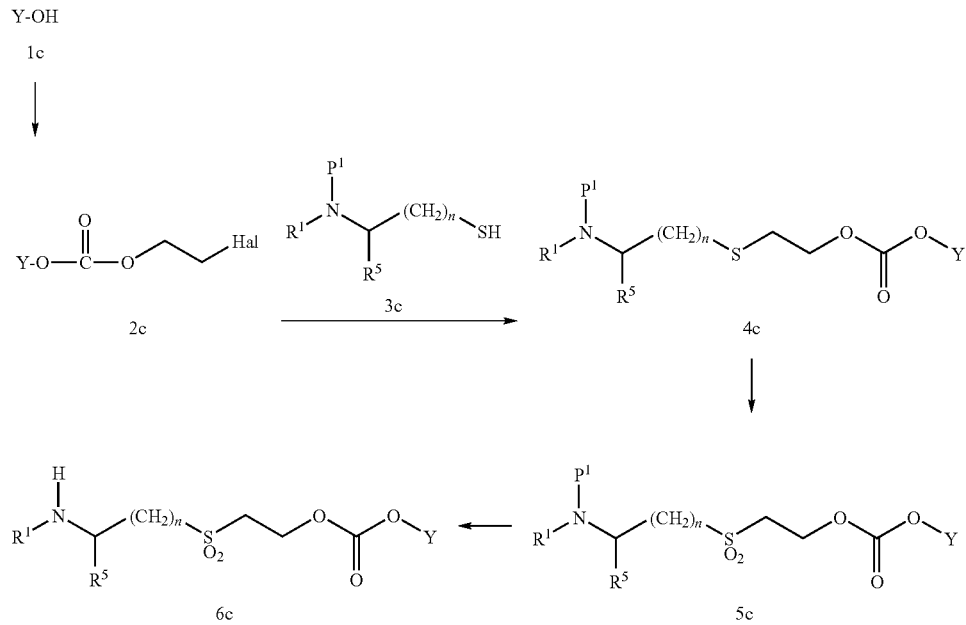
Reaction Process 3-2
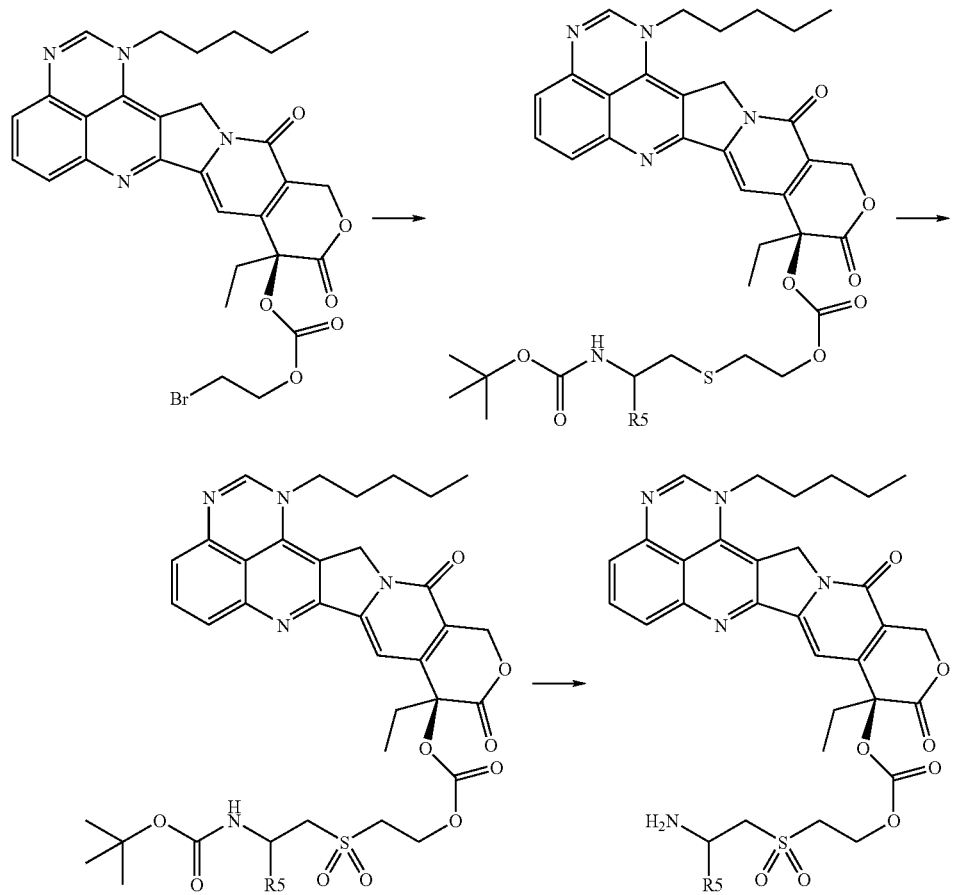

<Reaction Process 3>

Reactions 3-1 and 3-2 show another example of methods for producing water-soluble prodrugs whose solubilizing side chain comprises a sulfonyl group, as represented by the aforementioned formula (4).

Preparation of Compound 2c

First, a 2-halogenated ethyl carbonate (2c) is prepared from an alcohol (1c).

Conversion of the hydroxyl group of alcohol (1c) into a 2-halogenated ethyl carbonate can be performed by reaction with a commercially available chloroformate in an appropriate solvent.

Examples of a solvent that may be used include methylene chloride, ethyl acetate, tetrahydrofuran, acetonitrile, chloroform, dioxane, and dimethylformamide.

Usually, the reaction can be performed at −10° C. to 25° C., for 1 to 24 hours.

Preparation of Compound 3c

Thiol compound 3c comprising a solubilizing side chain can be prepared from a commercially available product, or it may be prepared by known methods (Tetrahedron, 1999, 55, 6623-6634; and J. Org. Chem. 1995, 60, 8105-8109).

Protection of the amino group in thiol compound (3c) can be performed suitably using known methods (see, The Practice of Peptide Synthesis, M. Bodansky, and A. Bodansky/2nd edition, 1994 (Springer-Verlag)).

Preparation of Compound 4c

Next, amino-group-protected carbonate (4c) can be obtained by reacting the corresponding amino-group-protected thiol compound (3c) with 2-halogenated ethyl carbonate (2c) in an appropriate solvent, under the presence of a base.

Examples of a solvent that may be used include methylene chloride, ethyl acetate, tetrahydrofuran, acetonitrile, chloroform, dioxane, dimethylformamide, methanol, and ethanol.

Examples of a base that may be used include triethylamine, diisopropylethylamine, potassium carbonate, and sodium carbonate.

Usually, the reaction can be performed at 15° C. to 100° C., for 1 to 24 hours.

Preparation of Compound 5c

Furthermore, compound 5c can be obtained using known methods by reacting compound 4c with a peroxidizing reagent.

Examples of a peroxidizing reagent that may be used include oxone, hydrogen peroxide, and m-chloroperbenzoic acid.

Usually, the reaction can be performed at −10° C. to 100° C., for 1 to 24 hours.

Preparation of Compound 6c

Compound (6c) can be obtained by removing the amino protecting group of compound 5c using known methods. Removal of the amino protecting group can be performed using known methods, as in the above-described Reaction Process 1. Examples include reacting trifluoroacetic acid for the removal of a Boc group, piperidine for the removal of an Fmoc group, and tetrabutylammonium fluoride for the removal of 2-(trimethylsilyl)ethoxycarbonyl (Teoc), trimethylsilylethyl and ter-butyldimethylsilyl groups, and removal of a Cbz group by catalytic hydrogenation.

Reaction Process 3-2 described above shows a specific example of such.

The above illustrates an example of the methods for producing the water-soluble prodrugs A2 of the present invention. The isolation and purification of the compounds of interest indicated in the Reaction Processes 1 to 3 described above can be performed by applying standard chemical operations, such as extraction, concentration, solvent removal, crystallization, filtration, recrystallization, and various chromatographies.

The compound A1 represented by formula (1), the water-soluble prodrugs A2 represented by formulas (2) to (5), and pharmaceutically acceptable salts, hydrates, and solvates thereof which are used in the present invention include all stereoisomers of the compounds mentioned above (for example, enantiomers, and diastereomers including cis and trans geometric isomers), racemates of the isomers, and other mixtures. In the present invention, the compound A1 represented by formula (1), the water-soluble prodrugs A2 represented by formulas (2) to (5), and compound B include stereoisomers, in particular.

The compound A1 represented by formula (1), the water-soluble prodrugs A2 represented by formulas (2) to (5), compound B, and pharmaceutically acceptable salts, hydrates, or solvates thereof which are used in the present invention, may exist in different tautomeric forms, such as the keto and enol forms, and the imine and enamine forms, or as mixtures of both. Tautomers exist as mixtures of a tautomeric set in solution. In solid form, usually one of the tautomers predominates. The compounds used in the present invention include all tautomers, even when only one of the tautomers is described.

Furthermore, the compounds used in the present invention include atropisomers. Atropisomers refer to compound A1 represented by formula (1), water-soluble prodrugs A2 represented by formulas (2) to (5), and compound B that can be resolved into isomers with restricted rotation.

These isomers can be isolated by standard methods based on their differences in physicochemical properties. For example, racemic compounds can be resolved into sterically pure isomers by standard optical resolution methods, such as optical resolution by derivatization to diastereomeric salts using an optically active acid such as tartaric acid. Diastereomeric mixtures can be resolved by using fractional crystallization, and various chromatographic techniques (for example, thin layer chromatography, column chromatography, and gas chromatography).

When the compounds used in the present invention can be obtained in the free form, they can be formed into salts, or converted to hydrates or solvates thereof, by standard methods.

Alternatively, when the compounds used in the present invention are obtained as salts, hydrates, or solvates, these compounds can be converted to their free form by standard methods. When compounds used in the present invention are obtained as salts, hydrates, or solvates, the dosage or the amount of active ingredient in a formulation can be determined by converting their weight to the weight of their free form (the weight obtained by subtracting the weight of the salt portion, water, or solvent from the weight of the salt, hydrate, or solvate).

Compound A (compound A1 represented by formula (1), or water-soluble prodrugs A2 represented by formulas (2) to (5)), and compound B (at least one type of compound selected from the group consisting of a platinum-type anticancer compound, a gemcitabine-type compound, a 5-FU-type compound, a taxane-type compound, a vinca alkaloid-type compound, an anticancer tyrosine kinase inhibitor compound, and an anticancer monoclonal antibody) used in the present invention have their own anticancer effects; however, by using compound A and compound B in combination, their anticancer effects increase synergistically.

In the present invention, prodrug A2 shows excellent water solubility. Moreover, because it is rapidly converted into the active form through chemical conversion while its characteristics (such as small interspecies and interindividual differences, and readiness to be made water-soluble) are maintained, the anticancer effect can be increased by combination with another compound B.

Examples of cancers for which the cancer therapeutic agents of the present invention are effective in treating include solid tumors. The agents can be applied to cancers such as brain tumor, glioma, head and neck cancer (pharyngeal cancer, laryngeal cancer, tongue cancer, etc.), esophageal cancer, stomach cancer, cancers of the large intestine (cecal cancer, colon cancer (ascending colon cancer, transverse colon cancer, sigmoid colon cancer), rectal cancer, colorectal carcinoma), lung cancer (small cell cancer, non-small cell cancer, etc.), thyroid cancer, breast cancer, gallbladder cancer, pancreatic cancer, liver cancer, prostate cancer, ovarian cancer, uterine cancer (cervical cancer, endometrial cancer), testicular cancer, renal cell cancer, bladder cancer, renal pelvis/ureter cancer, malignant melanoma, and skin cancer; preferably to colorectal cancer, lung cancer, breast cancer, stomach cancer, cervical cancer, bladder cancer, rectal cancer, pancreatic cancer, ovarian cancer, and such; and more preferably to colorectal cancer, lung cancer, breast cancer, stomach cancer, rectal cancer, pancreatic cancer, ovarian cancer, and such.

The present invention also relates to preventive or therapeutic methods for cancer, which comprise the step of administering a therapeutically effective dose of the aforementioned cancer therapeutic agents to patients in need. In cancer, these methods are particularly effective for treating, for example, solid tumors and cancers such as colorectal cancer, lung cancer, breast cancer, stomach cancer, cervical cancer, bladder cancer, rectal cancer, pancreatic cancer, and ovarian cancer, and preferably colorectal cancer, lung cancer, breast cancer, stomach cancer, rectal cancer, pancreatic cancer, and ovarian cancer.

When using the cancer therapeutic agents of the present invention as therapeutic agents or preventive agents for cancer, preferable examples of methods for administering them are parenteral (intravenous, intramuscular, subcutaneous) and local (drip infusion) administrations, and inhalation (intraoral or nasal spray).

The form of the individual formulations in the combination cancer therapeutic agents of the present invention can be selected according to the administration method. Examples are oral formulations such as tablets, capsules, powders, granules, or solutions, or sterilized liquid solutions and suspensions such as parenteral formulations, suppositories, and ointments.

Solid formulations can be produced in the form of tablets, capsules, granules, or powders by themselves, or they can be prepared using suitable carriers (additives). Examples of such carriers (additives) include sugars such as lactose or glucose; starch such as corn, wheat, or rice; fatty acids such as stearic acid; inorganic salts such as magnesium aluminometasilicate or anhydrous calcium phosphate; synthetic polymers such as polyvinylpyrrolidone or polyalkyleneglycol; fatty acid salts such as calcium stearate or magnesium stearate; alcohols such as stearyl alcohol or benzyl alcohol; synthetic cellulose derivatives such as methylcellulose, carboxymethylcellulose, ethylcellulose, or hydroxypropylmethylcellulose; and other conventionally used additives such as gelatin, talc, vegetable oil, gum arabic, and such.

Generally, these solid formulations including tablets, capsules, granules, and powders may comprise, as an active ingredient, for example, compound A at 0.1 to 100 weight percent, preferably 5 to 100 weight percent, more preferably 5 to 60 weight percent, and particularly preferably 5 to 40 weight percent of the total weight of the formulation.

Liquid formulations are produced in the form of suspensions, syrups, injections, drip infusions (intravenous drip infusions), or such using suitable additives conventionally used in liquid formulations, such as water, alcohols, or plant-derived oils such as soybean oil, peanut oil, or sesame oil.

In particular, examples of suitable solvents or diluents for parenteral administration in the form of intramuscular injection, intravenous injection, or subcutaneous injection include distilled water for injection, lidocaine hydrochloride solution (for intramuscular injection), physiological saline solution, aqueous glucose solution, ethanol, polyethylene glycol, propylene glycol, liquid for intravenous injection (for example, aqueous solutions of citric acid and sodium citrate), electrolyte solutions (for intravenous drip infusion and intravenous injection), and mixtures of these.

These injections may exist in a pre-dissolved form. Alternatively, they may exist in a powdered form or a form combined with a suitable carrier (additive) that is dissolved at the time of use. These injection solutions may comprise the active ingredient, for example, at 0.1 to 10 weight percent or preferably 0.1 to 5 weight percent of the total weight of the formulation.

Liquid formulations such as suspensions or syrups for oral administration may include the active ingredient, for example, at 0.5 to 10 weight percent of the total weight of the formulation.

When compound A is water-soluble prodrug A2, compound A is preferably used as an aqueous liquid formulation. More specifically, it can be used as an aqueous solution comprising water-soluble prodrug A2 which can be used in the present invention, its pharmaceutically acceptable salts, or hydrates or solvates thereof. Aqueous solutions that may be used include phosphate buffer, physiological saline, and various infusion solutions.

The pH of the aqueous solution is preferably 4 or less, more preferably 3 or less, and even more preferably between 2 and 3. In a solution at such pH, the water-soluble prodrugs represented by formulas (2) to (5), their pharmaceutically acceptable salts, or hydrates or solvates thereof can exist stably for long periods of time. On the other hand, under physiological conditions of preferably pH5 or higher, or more preferably pH7 to 8, the active form A1 can be rapidly and quantitatively dissociated in a short period of time.

Therefore, when using water-soluble prodrug A2, the active form A1 can be rapidly dissociated, for example in the blood, by injecting an aqueous liquid formulation that is particularly effective for use as an injection and whose pH is adjusted to preferably 4 or less, more preferably 3 or less, and even more preferably between 2 and 3.

In this case, examples of the dosage forms of water-soluble prodrug A2 preferably include aqueous solutions and suspensions for oral use and parenteral solutions packaged into containers suitable for separation into single doses. Furthermore, the dosage forms can be adapted to various administration methods including controlled-release formulations such as subcutaneous implants.

When using the cancer therapeutic agents of the present invention as therapeutic agents or preventive agents for cancer, the proportion and total amount of compound A, compound B, pharmaceutically acceptable salts thereof, or hydrates or solvates thereof which are used differently depending on the symptoms, age, body weight, relative health condition, presence of other administered pharmaceuticals, method of administration, and such.

For example, the generally effective amount delivered to a patient (warm-blooded animal, especially human) in terms of the dosage of compound A is roughly, for example, a daily dose in the range of 1 to 500 mg per adult in the case of oral administration.

In the case of parenteral administration, preferably intravenous administration, or more preferably intravenous drip infusion, the daily dose of compound A is, for example, preferably 0.1 to 1000 mg per kg body weight, and more preferably 10 to 800 mg per kg body weight. This is desirably administered once daily or in several portions throughout the day depending on the symptoms.

When using compound A, their pharmaceutically acceptable salts, or hydrates or solvates thereof as an aqueous solution, concentration of the aqueous solution (total amount of active ingredient) is not limited and varies according to the degree or type of the disease, but the preferred range is ordinarily 1 µM to 500 µM.

Herein, in the case of intravenous drip infusion, the administration may be continued, for example, for 1 to 4 hours, preferably for 2 to 3 hours, and more preferably for 2 hours. The number of administrations varies depending on the method of administration and the symptoms, but for example, it is once to five times a day, preferably once to twice a day, and more preferably once a day. Alternatively, it can be used for administration methods such as intermittent administrations, including alternate day administration and administration on every third day. In the case of treatment by parenteral administration, the period of medication discontinuation is, for example, 1 to 6 weeks, preferably 2 to 4 weeks, and more preferably 3 to 4 weeks.

The therapeutic course of the second anticancer agent such as compound B to be used in combination with compound A is not particularly limited, but it can be determined, if necessary, by those skilled in the art according to known literature and such. Examples are as indicated below.

In the case of intravenous injection, the therapeutic course of cisplatin is, for example, administration of 50 to 70 mg/m$^2$ (body surface area) once a day followed by three weeks or more of medication discontinuation (the dosage may be suitably decreased or increased). This is repeated as a course.

The therapeutic course of carboplatin is, for example, 300 to 400 mg/m$^2$ once a day over 30 minutes or more of intravenous drip infusion, followed by at least four weeks of medication discontinuation (the dose may be suitably decreased or increased). This is repeated as a course.

The therapeutic course of oxaliplatin is one intravenous injection of 85 mg/m$^2$ a day, followed by discontinuation of medication for two weeks. This is repeated as a course.

The therapeutic course of gemcitabine is, for example, 1 g/m$^2$ gemcitabine per administration over 30 minutes of intravenous drip infusion; and one administration per week for three consecutive weeks, followed by discontinuation of medication in the fourth week. This is repeatedly administered as a course. The dosage is suitably reduced according to the age, symptoms, or development of side effects.

The therapeutic course of 5-fluorouracil (5-FU) is as follows: in the case of oral administration, for example, 200 to 300 mg is administered daily for once to three times; in the case of injections, for example, 5 to 15 mg/kg is administered daily by intravenous injection or intravenous drip infusion for the first five consecutive days, followed by one administration of 5 to 7.5 mg/kg per day by intravenous injection or intravenous drip infusion every other day (the dose may be suitably decreased or increased).

In the case of oral administration, the therapeutic course of capecitabine is administration of a fixed dose, for example, twice a day for 14 to 21 consecutive days or so, followed by discontinuation of medication for seven days. This is repeatedly administered as a course. Depending on the body surface area, a single dose is, for example, 900 mg when the body surface area is less than 1.31 m$^2$, 1200 mg when the body surface area is 1.31 m$^2$ or more and less than 1.64 m$^2$, and 1500 mg when the body surface area is 1.64 m or more.

The therapeutic course of docetaxel (docetaxel hydrate) is, for example, administration of 60 mg/m$^2$ (body surface area) of docetaxel per day by one hour or longer of intravenous drip infusion at three to four week intervals (the dose may be suitably decreased or increased).

The therapeutic course of paclitaxel is, for example, administration of 210 mg/m$^2$ (body surface area) per day by three hours of intravenous drip infusion, followed by discontinuation of medication for at least three weeks. This is repeated as a course. The dosage may be suitably decreased or increased.

When anticancer compounds other than compound B are used additionally, therapeutic courses such as the following are preferable.

The therapeutic course of S-1 (Tegafur-Gimestat-Ostat potassium) is, for example, as follows: the initial dose (single dose) is set at the following standard quantity based on the body surface area, and administration is carried out orally twice a day: after breakfast and dinner, for 28 consecutive days, followed by discontinuation of medication for 14 days. This is repeatedly administered as a course. The initial standard quantity per body surface area (Tegaful equivalent) is as follows: 40 mg/dose for less than 1.25 m$^2$; 50 mg/dose for 1.25 m$^2$ or more to less than 1.5 m$^2$; and 60 mg/dose for 1.5 m$^2$ or more. This is suitably decreased or increased depending on the patient's conditions.

The therapeutic course of doxorubicin (for example, doxorubicin hydrochloride) in the case of intravenous injection is, for example, intravenous administration of 10 mg (0.2 mg/kg) (potency) in one shot per day for four to six consecutive days, followed by discontinuation of medication for seven to ten days. This is repeated two to three times as a course. The total dosage is preferably no more than 500 mg (potency)/m$^2$ (body surface area), and it may be suitably decreased or increased within this range.

The therapeutic course of etoposide in the case of intravenous injection is, for example, administration of 60 to 100 mg/m$^2$ (body surface area) per day for five consecutive days, followed by discontinuation of medication for three weeks (the dose may be suitably decreased or increased). This is repeated as a course. In contrast, in the case of oral administration, for example, 175 to 200 mg is administered per day for five consecutive days, followed by discontinuation of medication for three weeks (the dosage may be suitably decreased or increased). This is repeated as a course.

The therapeutic course of irinotecan (for example, irinotecan hydrochloride) is, for example, administration of 100 mg/m$^2$ once per day with three to four times of intravenous drip infusion at one week intervals, followed by discontinuation of medication for at least two weeks.

The therapeutic course of topotecan is, for example, administration of 1.5 mg/m$^2$ by intravenous drip infusion once a day for five days, followed by discontinuation of medication for at least three weeks.

The therapeutic course of cyclophosphamide is as follows: in the case of intravenous injection, for example, administration of 100 mg once a day by intravenous injection every day; if the patient can bear, the dosage may be increased to 200 mg per day. In total, 3,000 to 8,000 mg is administered; however, this may be suitably decreased or increased. Doses may be injected or infused intramuscularly, intrathoracically, or intratumorally, as required. In contrast, in the case of oral administration, for example, 100 to 200 mg is administered per day.

The therapeutic course of Iressa is, for example, oral administration of 250 mg once a day.

The therapeutic course of SU5416 is, for example, administration of 145 mg/m$^2$ by 60 minutes of intravenous drip infusion twice a week for four weeks. This is repeated as a course.

The therapeutic course of IMC-C225 is, for example, administration of 400 mg/m$^2$ by intravenous drip infusion on the first day, followed by administration of 250 mg/m$^2$ by intravenous drip infusion every week thereafter.

The therapeutic course of RhuMabVEGF is, for example, intravenous drip infusion of 3 mg/kg every week.

When 5-FU is combined with leucovorin, the therapeutic course is, for example, 425 mg/m$^2$ of 5-FU and 200 mg/m$^2$ of leucovorin administered by intravenous drip infusion from the first day to the fifth day, and this is repeated at four-week intervals.

The therapeutic course of Tarceva is oral administration of 150 mg erlotinib once a day on an empty stomach.

The therapeutic course of Herceptin is administration of 4 mg/kg (body weight) trastuzumab once a day for the initial administration, and administration of 2 mg/kg (body weight) by 90 minutes or longer of intravenous drip infusion for the second and later administrations at one-week intervals.

Cancer therapeutic agents of the present invention can be produced by known methods using additives such as stabilizers, flavoring agents, and diluents.

Examples of stabilizers include paraoxybenzoic acid esters such as methyl paraben, and propyl paraben; alcohols such as chlorobutanol, benzyl alcohol, and phenylethyl alcohol; benzalkonium chloride; phenols such as phenol and cresol; thimerosal; dehydroacetic acid; and sorbic acid.

Examples of flavoring agents include the commonly used sweetening agents, sour agents, and flavors.

Furthermore, examples of solvents that can be used to produce liquid agents include ethanol, phenol, chlorocresol, purified water, and distilled water.

Examples of surfactants or emulsifiers include polysorbate 80, polyoxyl 40 stearate, and lauromacrogol.

More specifically, for example, when a formulation comprising a second anticancer agent such as compound B which is used in combination with compound A is an oral formulation, it can be produced, for example, by mixing an appropriate amount of the anticancer agent with a suitable amount of lactose and filling this into a hard gelatin capsule suitable for oral administration. On the other hand, when the formulation comprising the anticancer agent is an injection, it can be prepared, for example, by mixing an appropriate amount of the anticancer agent with a suitable amount of 0.9% physiological saline solution, and filling this mixture into a vial for injection.

Furthermore, combination agents comprising compound A according to the present invention and another anticancer agent such as compound B can be easily produced by those skilled in the art according to conventional methods or common techniques.

All prior art references cited herein are incorporated by reference into this description.

BRIEF DESCRIPTION OF THE DRAWINGS

FIG. 1-2 shows the result of isobologram analysis on the effect of combining compound 10A (the active form of compound 2A prepared in Preparation Example 2) with compound 1B (CDDP) in the human stomach cancer cell lines MKN-28 and MKN-45, and the human ovarian cancer cell line OVCAR-3.

FIG. 2-1 shows the antitumor effects as a result of single or combination therapy using compound 2A, CPT-11, and capecitabine (compound 6B) in the human colorectal cancer HCT116 xenograft model. The arrows indicate the days that compound 2A or CPT-11 was administered, and the horizontal bars on the X axis indicate the days that capecitabine was administered. The vertical bars at each point indicate standard deviation. Symbols in the graph are the following: capecitabine: open triangles; compound 2A or CPT-11: filled circles; combination: filled triangles; and vehicle: open circles. Each group consisted of five mice, and the tumor volume is their average.

FIG. 2-2 shows the antitumor effects as a result of single or combination therapy using compound 2A, CPT-11, and capecitabine (compound 6B) in the human stomach cancer NCI-N87 xenograft model. The arrows indicate the days that compound 2A or CPT-11 was administered, and the horizontal bars on the X axis indicate the days that capecitabine was administered. The vertical bars at each point indicate standard deviation. Symbols in the graph are the following: capecitabine: open triangles; compound 2A or CPT-11: filled circles; combination: filled triangles; and vehicle: open circles. Each group consisted of five mice, and the tumor volume is their average.

FIG. 4-1 shows the antitumor effects as a result of combination therapy using compound 2A or CPT-11 and CDDP in the human lung cancer Calu-6 xenograft model. The arrows in the upper row indicate the days compound 2A or CPT-11 was administered, and the arrows in the lower row indicate the days CDDP was administered. The vertical bars at each point indicate standard deviation. Symbols in the graph are the following: CDDP: open triangles; compound 2A or CPT-11: filled circles; combination: filled triangles; and vehicle: open circles. Each group consisted of five mice, and the tumor volume is their average.

FIG. 4-2 shows the antitumor effects as a result of combination therapy using compound 2A and carboplatin in the human lung cancer Calu-6 xenograft model. The arrows in the upper row indicate the days that compound 2A was administered, and the arrows in the lower row indicate the days that carboplatin was administered. The vertical bars at each point indicate standard deviation. Symbols in the graph are the following: carboplatin: open triangles; compound 2A: filled circles; combination: filled triangles; and vehicle: open circles. Each group consisted of five mice, and the tumor volume is their average.

FIG. 5-1 shows the antitumor effects as a result of combination therapy using compound 2A and oxaliplatin in the human rectal cancer COL-16-JCK xenograft model, in which compound 2A was administered once a week. The arrows in the upper row indicate the days that compound 2A was administered, and the arrows in the lower row indicate the days that oxaliplatin was administered. The vertical bars at each point indicate standard deviation. Symbols in the graph are the following: oxaliplatin: open triangles; compound 2A: filled circles; combination: filled triangles; and vehicle: open circles. Each group consisted of five mice, and the tumor volume is their average.

FIG. 5-2 shows the antitumor effects as a result of combination therapy using compound 2A and oxaliplatin in the human rectal cancer COL-16-JCK xenograft model, in which compound 2A was administered once in two weeks. The arrows in the upper row indicate the days that compound 2A was administered, and the arrows in the lower row indicate the days that oxaliplatin was administered. The vertical bars at each point indicate standard deviation. Symbols in the graph are the following: oxaliplatin: open triangles; compound 2A: filled circles; combination: filled triangles; and vehicle: open circles. Each group consisted of five mice, and the tumor volume is their average.

BEST MODE FOR CARRYING OUT THE INVENTION

Figure 1:
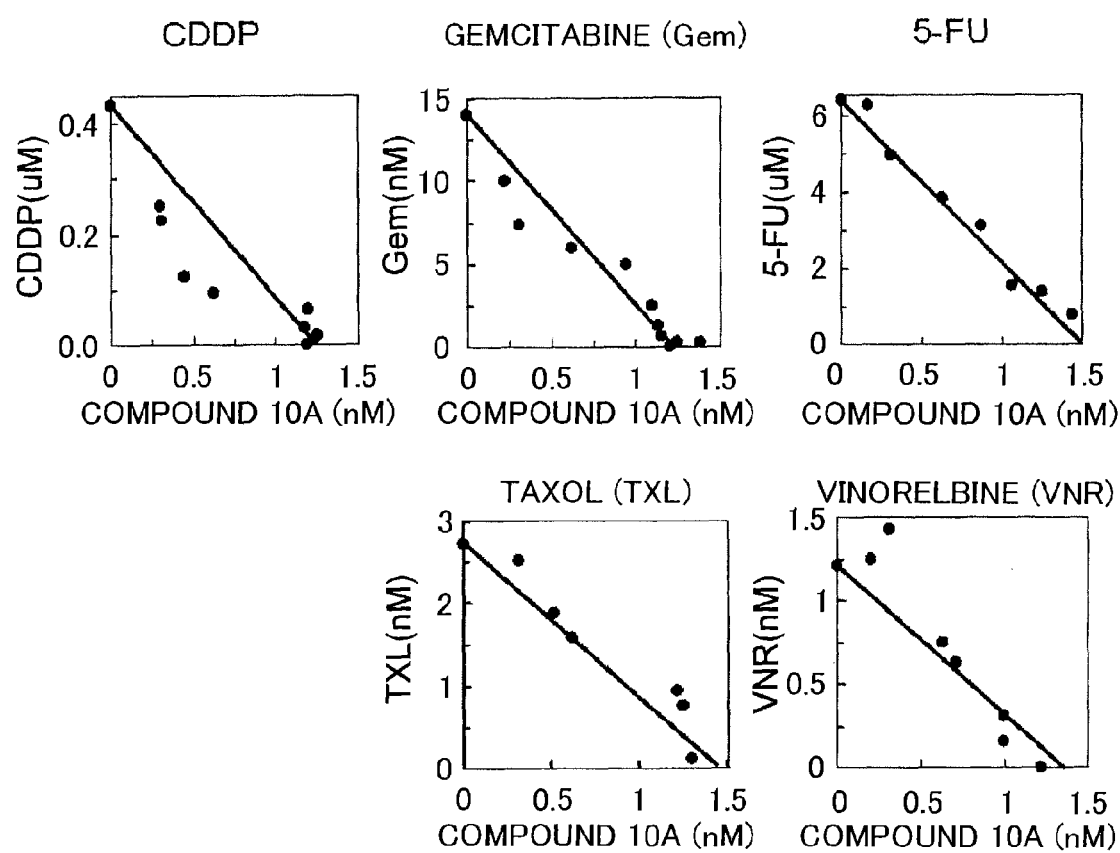
FIG. 1-1 shows the result of isobologram analysis on the effect of combining compound 10A (the active form of compound 2A prepared in Preparation Example 2) with another cytotoxic substance in the human lung cancer cell line Calu-6.

Hereinafter, an embodiment of the present invention is specifically illustrated with reference to Examples, but it is not to be construed as being limited thereto.

NMR analysis was performed using JEOL JNM-EX270 (270 MHz), JNMGSX400 (400 MHz), or JNM-A500 (500 MHz). NMR data were reported in ppm (parts per million) and referenced to the deuterium lock signal of the sample solvent.

Mass spectral data were obtained using JEOL JMS-DX303 or JMS-SX/SX102A.

Data from mass spectrometers equipped with a high performance liquid chromatography instrument were obtained using micromass (Micromass, ZMD) equipped with a Waters 996-600E gradient high performance liquid chromatography instrument, or micromass (Finnigan, Navigator) equipped with an Agilent 1100 gradient high performance liquid chromatography instrument (Agilent Technologies).

For synthetic organic reactions, commercially available reagents were used without further purification.

In the Examples, room temperature refers to a temperature in the range of approximately 20° C. to 25° C.

All water-free reactions were performed under nitrogen atmosphere. Concentration or solvent removal under reduced pressure was performed using a rotary evaporator, unless stated otherwise.

Compounds were prepared while having their functional groups protected with protecting groups, as necessary, and the protecting groups were removed after preparation of the protected form of a target molecule was completed. Selection of the protecting group, and attachment and detachment manipulations were performed, for example, according to the methods described in "Greene and Wuts, Protective Group in Organic Synthesis/2nd edition, John Wiley & Sons, 1991".

High performance liquid chromatography employed one of the following two conditions.

High Performance Liquid Chromatography Condition 1
Column: Combi ODS (ODS, 5 µm, 4.6 mm I.D.×50 mm, Wako Pure Chemicals), COSMOSIL (ODS, 5 µm, 4.6 mm I.D.×50 mm, Nakalai Tesque), or Inertsil C18 (ODS, 5 µm, 4.6 mm I.D.×50 mm, GL Science)
Mobile phase: (A) water containing 0.01% trifluoroacetic acid, and (B) acetonitrile containing 0.01% trifluoroacetic acid.
Elution method: stepwise solvent gradient elution of: 10% B to 95% B (3.5 minutes), 95% B to 10% B (1 minute), and 10% B (0.5 minutes)
Flow rate: 4.0 mL/minute
High Performance Liquid Chromatography Condition 2
Column: Combi ODS (ODS, 5 µm, 4.6 mm I.D.×50 mm, Wako Pure Chemicals), COSMOSIL (ODS, 5 µm, 4.6 mm I.D.×50 mm, Nakalai Tesque), or Inertsil C18 (ODS, 5 µm, 4.6 mm I.D.×50 mm, GL Science)
Mobile phase: (A) water containing 0.01% trifluoroacetic acid, and (B) acetonitrile containing 0.01% trifluoroacetic acid.
Elution method: stepwise solvent gradient elution of: 30% B to 35% B (0.2 minutes), 35% B to 98% B (3.3 minute), 98% B to 30% B (1 minute), and 30% B (0.5 minutes)
Flow rate: 4.0 mL/minute

Preparation Example 1

(9S)-9-Ethyl-9-{[methyl-(2-methylamino-ethyl)-amino]-acetoxy}-1-pentyl-1H,12H-pyrano[3",4":6'7']indolizino[1',2':6,5]pyrido[4,3,2-de]quinazoline-10,13(9H,15H)-dione hydrochloride (Compound 1A)

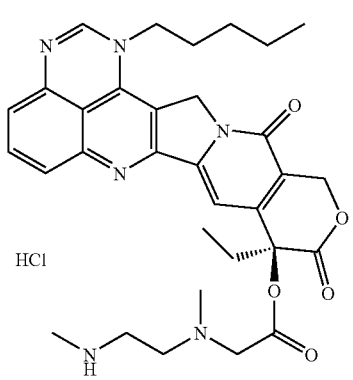

Process 1-A

{[2-(tert-Butoxycarbonyl-methyl-amino)-ethyl]-methyl-amino}-acetic Acid Benzyl Ester

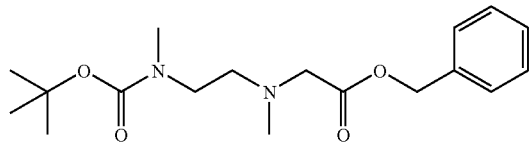

854 mg (4.54 mmol) of methyl-(2-methyl-amino-ethyl)-carbamic acid tert-butyl ester, which is a known substance (J. Med. Chem., 2000, 43, 3093), was dissolved in methylene chloride (50 mL), and then benzyl 2-bromoacetate (1.0 mL, 6.35 mmol) was added to this solution, and the mixture was stirred at room temperature for approximately 24 hours.

After completion of the reaction, the reaction solution was concentrated, and the residue obtained was purified by silica gel column chromatography (hexane:ethyl acetate=5:1 to 3:1) to give 534.3 mg (35%) of {[2-(tert-butoxycarbonyl-methyl-amino)-ethyl]-methyl-amino}-acetic acid benzyl ester as a colorless viscous oil.

$^1$H-NMR (270 MHz, CDCl$_3$) δ(ppm): 1.42 (9H, s), 2.40 (3H, s), 2.65 (2H, t, J=7.1 Hz), 2.82 (3H, s), 3.20-3.38 (2H, m), 3.34 (2H, s), 5.13 (2H, s), 7.24-7.38 (5H, m)

ESI (LC-MS positive mode) m/z 337 (M+H).

Process 1-B

{[2-(tert-Butoxycarbonyl-methyl-amino)-ethyl]-methyl-amino}-acetic Acid

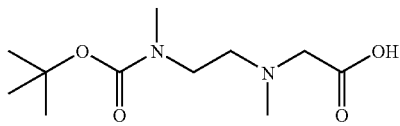

534.3 mg (1.59 mmol) of {[2-(tert-butoxycarbonyl-methyl-amino)-ethyl]-methyl-amino}-acetic acid benzyl ester prepared in Process 1-A was dissolved in methanol (20 mL), and then 51 mg of 5% palladium-carbon was added, and this was stirred for 1 hour under hydrogen atmosphere at room temperature. Insoluble substances were removed by filtration, and the filtrate was concentrated to give 391.1 mg (100%) of {[2-(tert-butoxycarbonyl-methyl-amino)-ethyl]-methyl-amino}-acetic acid as a colorless viscous oil.

$^1$H-NMR (270 MHz, CDCl$_3$) δ(ppm): 1.43 (9H, s), 2.72 (3H, s), 2.87 (3H, s), 2.95-3.10 (2H, m), 3.45 (2H, s), 3.31-3.63 (2H, m)

ESI (LC-MS positive mode) m/z 247 (M+H)

Process 1-C (9S)-9-({[2-(tert-Butoxycarbonyl-methyl-amino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione

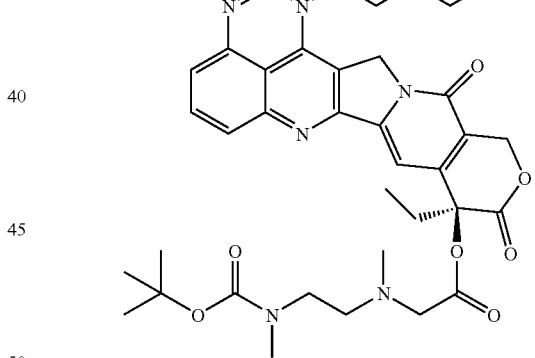

391 mg (1.59 mmol) of {[2-(tert-butoxycarbonyl-methyl-amino)-ethyl]-methyl-amino}-acetic acid prepared in Process 1-B, 279 mg (0.61 mmol) of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione (prepared according to Example 2.15 of WO03/045952), 525 mg (2.74 mmol) of 1-ethyl-3-(3-dimethylaminopropyl)-carbodiimide hydrochloride, and 224 mg (1.83 mmol) of 4-dimethylaminopyridine were dissolved in methylene chloride (15 mL), and then stirred at room temperature for four hours.

The reaction solution was washed with 0.15 N aqueous hydrochloric acid, dried over anhydrous sodium sulfate, and then the solvent was distilled off under reduced pressure. By purifying the resulting residue using silica gel column chromatography (methylene chloride:methanol=30:0 to 10:1), 136.4 mg (33%) of (9S)-9-({[2-(tert-butoxycarbonyl-methylamino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione was obtained as a yellow amorphous substance.

¹H-NMR (270 MHz, CDCl₃) δ(ppm): 0.85-0.95 (6H, m), 1.27-1.50 (4H, m), 1.40 (9H, s), 1.70-1.84 (2H, m), 2.03-2.30 (2H, m), 2.39 (3H, s), 2.58-2.70 (2H, m), 2.80 (3H, s), 3.18-3.36 (2H, m), 3.48 (2H, s), 3.81 (2H, t, J=7.3 Hz), 5.21 (2H, s), 5.37 (1H, d, J=17.3 Hz), 5.64 (1H, d, J=17.3 Hz), 7.07 (1H, s), 7.14 (1H, dd, J=1.3, 7.3 Hz), 7.38 (1H, s), 7.53-7.70 (2H, m)

ESI (LC-MS positive mode) m/z 687 (M+H).

Process 1-D (9S)-9-Ethyl-9-{[methyl-(2-methylamino-ethyl)-amino]-acetoxy}-1-pentyl-1H,12H-pyrano[3",4":6',7']indolizino[1',2':6,5]pyrido[4,3,2-de]quinazoline-10,13(9H,15H)-dione hydrochloride

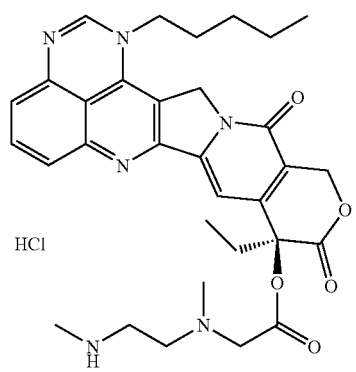

136.4 mg (0.20 mmol) of (9S)-9-({[2-(tert-butoxycarbonyl-methyl-amino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione prepared in Process 1-C was dissolved in 1 N hydrochloric acid-acetic acid solution (3 mL), and then stirred at room temperature for 2.5 hours.

Ethyl acetate was added to the reaction solution, this was then stirred at room temperature for 30 minutes, and the resulting solid was collected by filtration, and 102.7 mg (74%) of (9S)-9-ethyl-9-{[methyl-(2-methylamino-ethyl)-amino]-acetoxy}-1-pentyl-1H,12H-pyrano[3",4":6',7']indolizino[1',2':6,5]pyrido[4,3,2-de]quinazoline-10,13(9H,15H)-dione hydrochloride (compound 1A) was obtained as a yellowish red solid.

¹H-NMR (270 MHz, CD₃OD) δ(ppm): 0.99 (3H, t, J=6.9 Hz), 1.09 (3H, t, J=7.4 Hz), 1.40-1.62 (4H, m), 1.88-2.02 (2H, m), 2.15-2.31 (2H, m), 2.75 (3H, s), 2.96-3.06 (3H, m), 3.39-3.62 (4H, m), 4.25 (2H, t, J=7.9 Hz), 4.44-4.60 (1H, m), 4.87-5.03 (1H, m), 5.53 (2H, s), 5.54 (1H, d, J=17.2 Hz), 5.67 (1H, d, J=17.2 Hz), 7.55 (1H, d, J=7.3 Hz), 7.96-8.17 (3H, m), 8.33 (1H, s)

ESI (LC-MS positive mode) m/z 587 (M+H).

Preparation Example 2

(9S)-9-Ethyl-9-(glycyl-sarcosyloxy)-1-pentyl-1H,12H-pyrano[3",4":6',7']indolizino[1',2':6,5]pyrido[4,3,2-de]quinazoline-10,13(9H,15H)-dione hydrochloride (Compound 2A)

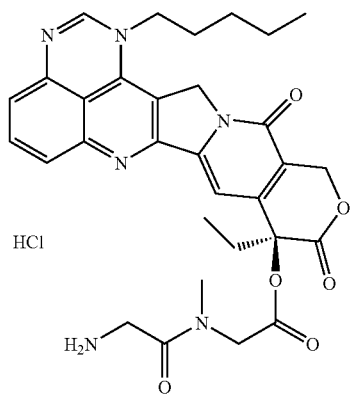

Process 2-A (9S)-9-{[N-(tert-Butoxycarbonyl)-glycyl]-sarcosyloxy}-9-ethyl-1-pentyl-1H,12H-pyrano[3",4":6',7']indolizino[1',2':6,5]pyrido[4,3,2-de]quinazoline-10,13(9H,15H)-dione

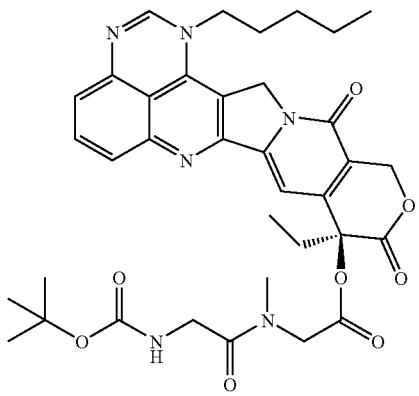

1.4 g (5.67 mmol) of [N-(tert-butoxycarbonyl)-glycyl]-sarcosine, which is a known substance (Helvetica Chimica Acta, 1991, 74, 197), 1.3 g (2.84 mmol) of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione, 2.2 g (11.34 mmol) of 1-ethyl-3-(3-dimethylaminopropyl)-carbodiimide hydrochloride, and 1.4 g (11.34 mmol) of 4-dimethylaminopyridine were dissolved in methylene chloride (50 mL), and then stirred at room temperature for 1.5 hours.

The reaction solution was washed with 0.2 N aqueous hydrochloric acid and saturated aqueous sodium hydrogen carbonate solution, then dried over anhydrous sodium sulfate, and then the solvent was distilled off under reduced pressure. Purification of the resulting residue was performed using silica gel column chromatography (methylene chloride: methanol=100:1 to 30:1), and as a result, 1.34 g (69%) of (9S)-9-{[N-(tert-butoxycarbonyl)-glycyl]-sarcosyloxy}-9-ethyl-1-pentyl-1H,12H-pyrano[3",4":6',7']indolizino[1',2':6,5]pyrido[4,3-2-de]quinazoline-10,13(9H,15H)-dione was obtained as a yellowish red amorphous substance.

¹H-NMR (270 MHz, CDCl₃) δ(ppm):
Rotamer A* 0.86-1.04 (6H, m), 1.24-1.53 (4H, m), 1.38 (9H, s), 1.70-1.90 (2H, m), 2.03-2.36 (2H, m), 3.04 (3H, s), 3.83 (2H, t, J=7.1 Hz), 3.96-4.05 (2H, m), 4.12 (1H, d, J=17.7 Hz), 4.57 (1H, d, J=17.7 Hz), 5.21 (2H, s), 5.38 (1H, d, J=17.3 Hz), 5.46-5.56 (1H, m), 5.66 (1H, d, J=17.3 Hz), 7.10-7.21 (2H, m), 7.40 (1H, s), 7.60-7.75 (2H, m);

Rotamer B* 0.86-1.04 (6H, m), 1.24-1.53 (4H, m), 1.38 (9H, s), 1.70-1.90 (2H, m), 2.03-2.36 (2H, m), 3.02 (3H, s), 3.83 (2H, t, J=7.1 Hz), 3.90-3.96 (2H, m), 4.12 (1H, d, J=17.7 Hz), 4.57 (1H, d, J=17.7 Hz), 5.24 (2H, s), 5.38 (1H, d, J=17.3 Hz), 5.46-5.56 (1H, m), 5.68 (1H, d, J=17.3 Hz), 7.10-7.21 (2H, m), 7.40 (1H, s), 7.60-7.75 (2H, m).

*The ratio of the two rotamers, A and B, was approximately 5:1.

ESI (LC-MS positive mode) m/z 687 (M+H).

Process 2-B (9S)-9-Ethyl-9-(glycyl-sarcosyloxy)-1-pentyl-1H, 12H-pyrano[3",4":6',7']indolizino[1',2':6,5]pyrido[4,3-2-de]quinazoline-10,13(9H,15H)-dione hydrochloride

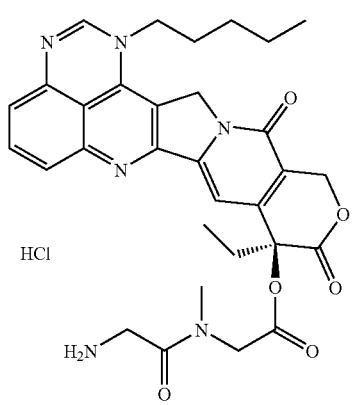

1.33 g (1.94 mmol) of (9S)-9-{[N-(tert-butoxycarbonyl)-glycyl]-sarcosyloxy}-9-ethyl-1-pentyl-1H,12H-pyrano[3", 4":6',7']indolizino[1',2':6,5]pyrido[4,3-2-de]quinazoline-10, 13(9H,15H)-dione, which was prepared in Process 2-A, was dissolved in 1 N hydrochloric acid-acetic acid solution (15 mL), and then stirred at room temperature for 2 hours and 45 minutes.

Ethyl acetate was added to the reaction solution, which was then stirred at room temperature for 30 minutes, the resulting solid was collected by filtration, and 1.28 g (100%) of (9S)-9-ethyl-9-(glycyl-sarcosyloxy)-1-pentyl-1H,12H-pyrano[3",4":6',7']indolizino[1',2':6,5]pyrido[4,3-2-de]quinazoline-10,13(9H,15H)-dione hydrochloride (compound 2A) was obtained as a yellow solid.

¹H-NMR (270 MHz, CD₃OD) δ(ppm):
Rotamer A* 0.99 (3H, t, J=7.1 Hz), 1.03 (3H, t, J=7.6 Hz), 1.34-1.58 (4H, m), 1.90-2.00 (2H, m), 2.14-2.30 (2H, m), 3.11 (3H, s), 3.99 (2H, s), 4.25 (2H, t, J=7.3 Hz), 4.56 (1H, d, J=17.9 Hz), 4.57 (1H, d, J=17.9 Hz), 5.51 (1H, d, J=17.4 Hz), 5.52 (2H, s), 5.61 (1H, d, J=17.4 Hz), 7.52-7.57 (1H, m), 7.89 (1H, s), 7.80 (1H, d, J=8.2 Hz), 8.10 (1H, t, J=8.2 Hz), 8.38 (1H, s);

Rotamer B* 0.99 (3H, t, J=7.1 Hz), 1.08 (3H, t, J=7.3 Hz), 1.34-1.58 (4H, m), 1.90-2.00 (2H, m), 2.14-2.30 (2H, m), 3.08 (3H, s), 3.90 (1H, d, J=16.5 Hz), 4.02 (1H, d, J=16.5 Hz), 4.25 (2H, t, J=7.3 Hz), 4.62 (1H, d, J=18.8 Hz), 4.76 (1H, d, J=18.8 Hz), 5.52 (2H, s), 5.53 (1H, d, J=16.9 Hz), 5.65 (1H, d, J=16.9 Hz), 7.52-7.57 (1H, m), 8.03 (1H, d, J=8.2 Hz), 8.10 (1H, t, J=8.2 Hz), 8.19 (1H, s), 8.34 (1H, s).

*The ratio of the two rotamers, A and B, was approximately 3:2.

ESI (LC-MS positive mode) m/z 587 (M+H).

Preparation Example 3

(9S)-9-{[(2-Amino-ethyl)-methyl-amino]-acetoxy}-9-ethyl-1-pentyl-1H,12H-pyrano[3",4":6',7']indolizino[1',2':6,5]pyrido[4,3-2-de]quinazoline-10,13 (9H,15H)-dione hydrochloride (Compound 3A)

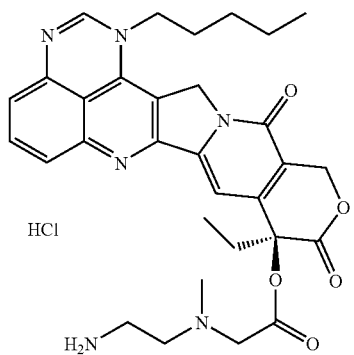

Process 3-A

{[2-(tert-Butoxycarbonylamino)-ethyl]-methyl-amino}-acetic Acid Benzyl Ester

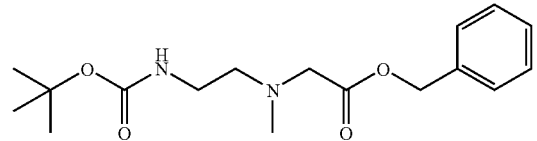

500 mg (1.42 mmol) of sarcosine benzyl ester p-toluenesulfonate, 478 mg (2.13 mmol) of 2-(tert-butoxycarbonylamino)-ethyl bromide, and 0.25 mL (2.13 mmol) of diisopropyl-ethylamine were dissolved in methylene chloride (10 mL), and then stirred at room temperature for approximately three days. After completion of the reaction, the reaction solution was concentrated and the residue obtained was purified by silica gel column chromatography (ethyl acetate) to yield 175 mg (38%) of {[2-(tert-butoxycarbonylamino)-ethyl]-methyl-amino}-acetic acid benzyl ester as a colorless viscous oil.

¹H-NMR (270 MHz, CDCl₃) δ(ppm): 1.44 (9H, s), 2.37 (3H, s), 2.63 (2H, t, J=6.0 Hz), 3.20 (2H, br.q), 3.33 (2H, s), 5.15 (1H, br.s), 5.16 (2H, s), 7.32-7.39 (5H, m)

ESI (LC-MS positive mode) m/z 323 (M+H).

Process 3-B

{[2-(tert-Butoxycarbonylamino)-ethyl]-methyl-amino}-acetic Acid

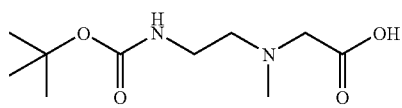

162 mg (0.5 mmol) of {[2-(tert-butoxycarbonylamino)-ethyl]-methyl-amino}-acetic acid benzyl ester prepared in Process 3-A was dissolved in methanol (5 mL), and then 5% palladium-carbon was added to it, and this was stirred under a hydrogen atmosphere at room temperature for one hour. After filtering off the insoluble material, the filtrate was concentrated to yield 116 mg (100%) of {[2-(tert-butoxycarbonylamino)-ethyl]-methyl-amino}-acetic acid as a colorless viscous oil.

$^1$H-NMR (270 MHz, CD$_3$OD) δ(ppm): 1.45 (9H, s), 2.91 (3H, s), 3.22 (2H, t, J=6.3 Hz), 3.41 (2H, t, J=6.3 Hz), 3.63 (2H, s)

ESI (LC-MS positive mode) m/z 233 (M+H).

Process 3-C (9S)-9-({[2-(tert-Butoxycarbonylamino)-ethyl]-methyl-amino}-acetoxy)-9-ethyl-1-pentyl-1H,12H-pyrano[3",4":6',7']indolizino[1',2':6,5]pyrido[4,3-de]quinazoline-10,13(9H,15H)-dione

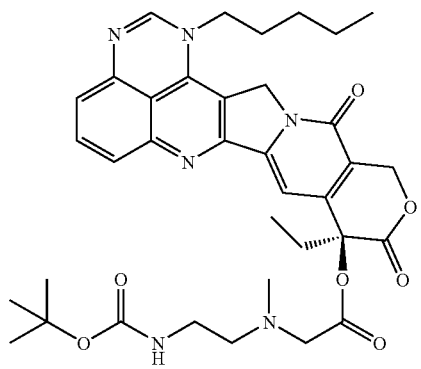

112 mg (0.48 mmol) of {[2-(tert-butoxycarbonylamino)-ethyl]-methyl-amino}-acetic acid prepared in Process 3-B, 157 mg (0.34 mmol) of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione, 197 mg (1.03 mmol) of 1-ethyl-3-(3-dimethylaminopropyl)-carbodiimide hydrochloride, and 83 mg (0.68 mmol) of 4-dimethylaminopyridine were dissolved in methylene chloride (10 mL), and then stirred at room temperature for three hours.

The reaction solution was washed with 0.3 N aqueous hydrochloric acid solution, dried over anhydrous sodium sulfate, and then the solvent was distilled off under reduced pressure. By purifying the obtained residue by silica gel column chromatography (methylene chloride:methanol=50:1), 61 mg (27%) of (9S)-9-({[2-(tert-butoxycarbonylamino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione was obtained as a yellow viscous oil.

$^1$H-NMR (270 MHz, CDCl$_3$) δ(ppm): 0.88-1.00 (6H, m), 1.32-1.53 (4H, m), 1.42 (9H, s), 1.73-1.86 (2H, m), 2.08-2.36 (2H, m), 2.39 (3H, s), 2.63 (2H, t, J=5.9 Hz), 3.20 (2H, br.q), 3.46 (2H, s), 3.82 (2H, t, J=7.1 Hz), 5.21 (1H, br.s), 5.22 (2H, s), 5.40 (1H, d, J=17.2 Hz), 5.67 (1H, d, J=17.2 Hz), 7.10 (1H, s), 7.14 (1H, br.d), 7.40 (1H, br.s), 7.58-7.70 (2H, m)

ESI (LC-MS positive mode) m/z 673 (M+H).

Process 3-D (9S)-9-{[(2-Amino-ethyl)-methyl-amino]-acetoxy}-9-ethyl-1-pentyl-1H,12H-pyrano[3",4":6',7']indolizino[1',2':6,5]pyrido[4,3,2-de]quinazoline-10,13(9H,15H)-dione hydrochloride

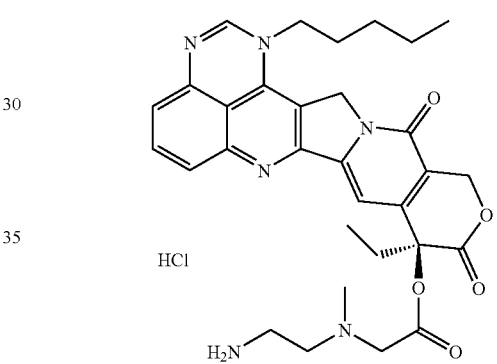

58 mg (0.086 mmol) of (9S)-9-({[2-(tert-butoxycarbonylamino)-ethyl]-methyl-amino}-acetoxy)-9-ethyl-1-pentyl-1H,12H-pyrano[3",4":6',7']indolizino[1',2':6,5]pyrido[4,3,2-de]quinazoline-10,13(9H,15H)-dione prepared in Process 3-C was dissolved in 1N hydrochloric acid-acetic acid solution (2 mL), and then stirred at room temperature for four hours.

Ethyl acetate was added to the reaction solution, which was then stirred at room temperature for 30 minutes, and the resulting solid was collected by filtration, and thus, 54 mg (93%) of (9S)-9-{[(2-amino-ethyl)-methyl-amino]-acetoxy}-9-ethyl-1-pentyl-1H,12H-pyrano[3",4":6',7']indolizino[1',2':6,5]pyrido[4,3,2-de]quinazoline-10,13(9H,15H)-dione hydrochloride (compound 3A) was obtained as a yellow solid.

$^1$H-NMR (270 MHz, CD$_3$OD) δ(ppm): 0.99 (3H, t, J=6.9 Hz), 1.09 (3H, t, J=7.3 Hz), 1.39-1.62 (4H, m), 1.88-2.02 (2H, m), 2.16-2.30 (2H, m), 3.07 (3H, s), 3.37-3.61 (4H, m), 4.25 (2H, br.t), 4.62 (1H, d, J=17.5 Hz), 5.05 (1H, d, J=17.5 Hz), 5.52 (2H, s), 5.53 (1H, d, J=17.5 Hz), 5.67 (1H, d, J=17.5 Hz), 7.55 (1H, br.d), 7.98-8.16 (3H, m), 8.32 (1H, s)

ESI (LC-MS positive mode) m/z 573 (M+H).

Preparation Example 4

(9S)-9-Ethyl-9-(sarcosyl-sarcosyloxy)-1-pentyl-1H, 12H-pyrano[3",4":6',7']indolizino[1',2':6,5]pyrido[4, 3,2-de]quinazoline-10,13(9H,15H)-dione hydrochloride (compound 4A)

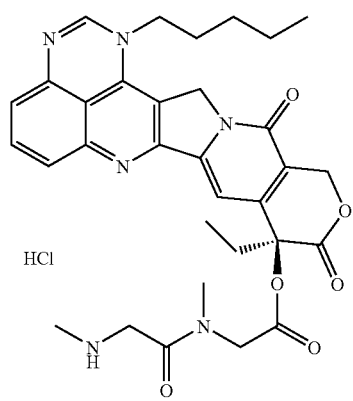

Process 4-A (9S)-9-{[N-(tert-Butoxycarbonyl)-sarcosyl]-sarcosyloxy}-9-ethyl-1-pentyl-1H,12H-pyrano[3",4":6',7'] indolizino[1',2':6,5]pyrido[4,3,2-de]quinazoline-10, 13(9H,15H)-dione

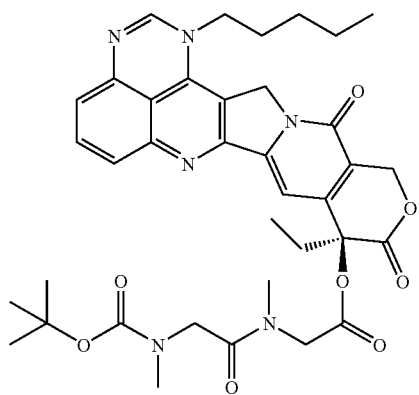

113 mg (0.44 mmol) of [N-(tert-butoxycarbonyl)-sarcosyl]-sarcosine, which is a known substance, 100 mg (0.22 mmol) of (9S)-9-ethyl-9-hydroxy-1-pentyl-1H,12H-pyrano [3",4":6',7']indolizino[1',2':6,5]pyrido[4,3,2-de]quinazoline-10,13(9H,15H)-dione, 125 mg (0.65 mmol) of 1-ethyl-3-(3-dimethylaminopropyl)-carbodiimide hydrochloride, and 53 mg (0.44 mmol) of 4-dimethylaminopyridine were dissolved in methylene chloride (6 mL), and then stirred at room temperature for 3.5 hours.

The reaction solution was washed with 0.25 N aqueous hydrochloric acid and aqueous sodium hydrogen carbonate solution, dried over anhydrous sodium sulfate, and then the solvent was distilled off under reduced pressure. The obtained residue was purified by silica gel column chromatography (methylene chloride:methanol=50:1), and 103 mg (68%) of (9S)-9-{[N-(tert-butoxycarbonyl)-sarcosyl]-sarcosyloxy}-9-ethyl-1-pentyl-1H,12H-pyrano[3",4":6',7']indolizino[1', 2':6,5]pyrido[4,3,2-de]quinazoline-10,13(9H,15H)-dione was obtained as a yellow amorphous substance.

$^1$H-NMR (400 MHz, CDCl$_3$) δ(ppm):
0.88-1.02 (6H, m), 1.25-1.51 (13H, m), 1.73-1.82 (2H, m), 2.11-2.32 (2H, m), 2.84 (3H, m), 3.02 (3H, m), 3.80 (2H, br.t), 3.92-4.29 (3H, m), 4.58-4.71 (1H, m), 5.12-5.70 (4H, m), 7.04-7.19 (2H, m), 7.39 (1H, m), 7.55-7.68 (2H, m)

ESI (LC-MS positive mode) m/z 701 (M+H).

Process 4-B (9S)-9-Ethyl-9-(sarcosyl-sarcosyloxy)-1-pentyl-1H, 12H-pyrano[3",4":6',7']indolizino[1',2':6,5]pyrido[4, 3,2-de]quinazoline-10,13(9H,15H)-dione hydrochloride

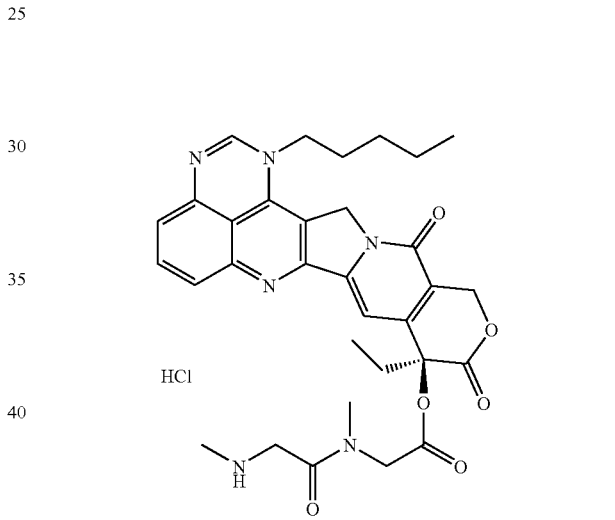

98 mg (0.14 mmol) of (9S)-9-{[N-(tert-butoxycarbonyl)-sarcosyl]-sarcosyloxy}-9-ethyl-1-pentyl-1H,12H-pyrano [3",4":6',7']indolizino[1',2':6,5]pyrido[4,3,2-de]quinazoline-10,13(9H,15H)-dione prepared in Process 4-A was dissolved in 1 N hydrochloric acid-acetic acid solution (3 mL), and then stirred at room temperature for two hours.

Ethyl acetate was added to the reaction solution, which was then stirred at room temperature for 30 minutes, and the resulting solid was collected by filtration, and thus, 67 mg (71%) of (9S)-9-ethyl-9-(sarcosyl-sarcosyloxy)-1-pentyl-1H,12H-pyrano[3",4":6',7']indolizino[1',2':6,5]pyrido[4,3, 2-de]quinazoline-10,13(9H,15H)-dione hydrochloride (compound 4A) was obtained as a yellow solid.

$^1$H-NMR (270 MHz, CD$_3$OD) δ(ppm):
0.96-1.11 (6H, m), 1.40-1.62 (4H, m), 1.87-2.01 (2H, m), 2.15-2.31 (2H, m), 2.71 (3H, s), 3.10 (3H, m), 4.05-4.15 (2H, m), 4.24 (2H, br.t), 4.55-4.70 (2H, m), 5.46-5.70 (4H, m), 7.52 (1H, m), 7.81-8.15 (3H, m), 8.34 (1H, m)

ESI (LC-MS positive mode) m/z 601 (M+H).

Preparation Example 5

(9S)-9-{2-[(R-2-Amino-2-methoxycarbonyl)ethanesulfonyl]ethoxycarbonyloxy}-9-ethyl-1-pentyl-1H, 12H-pyrano[3",4":6' 7']indolizino[1',2':6,5]pyrido[4,3,2-de]quinazoline-10,13(9H, 15H)-dione trifluoroacetate (Compound 5A)

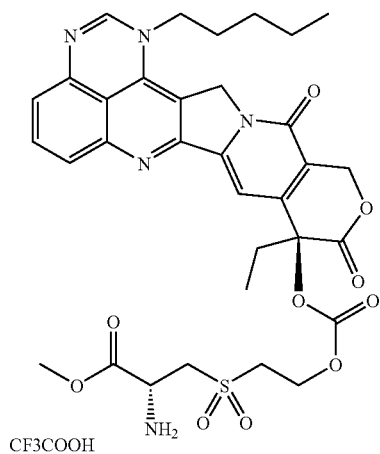

Process 5-A (9S)-9-(2-Bromo-ethoxycarbonyloxy)-9-ethyl-1-pentyl-1H,12H-pyrano[3",4":6',7']indolizino[1',2':6, 5]pyrido[4,3,2-de]quinazoline-10,13(9H,15H)-dione

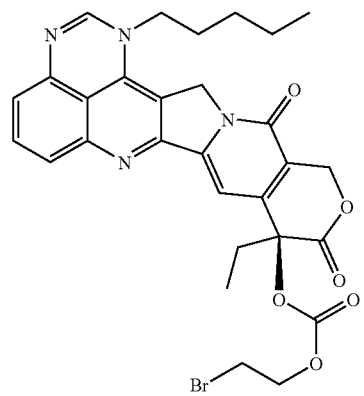

620 mg (1.35 mmol) of (9S)-9-ethyl-9-hydroxy-1-pentyl-1H,12H-pyrano[3",4":6',7']indolizino[1',2':6,5]pyrido[4,3,2-de]quinazoline-10,13(9H,15H)-dione, 0.29 mL (2.70 mmol) of 2-bromoethyl chloroformate, 0.47 mL (2.70 mmol) of diisopropyl-ethylamine, and 165 mg (1.35 mmol) of 4-dimethylaminopyridine were dissolved in methylene chloride (20 mL), and then stirred at room temperature for approximately 24 hours.

The reaction solution was washed with 0.3 N aqueous hydrochloric acid, dried over anhydrous sodium sulfate, and then the solvent was distilled off under reduced pressure. By purifying the obtained residue by silica gel column chromatography (ethyl acetate), 681 mg (83%) of (9S)-9-(2-bromo-ethoxycarbonyloxy)-9-ethyl-1-pentyl-1H,12H-pyrano[3", 4":6',7']indolizino[1',2':6,5]pyrido[4,3,2-de]quinazoline-10, 13(9H,15H)-dione was obtained as a yellow solid.

$^1$H-NMR (270 MHz, CDCl$_3$) δ(ppm): 0.93 (3H, t, J=7.3 Hz), 1.00 (3H, t, J=7.6 Hz), 1.31-1.54 (4H, m), 1.72-1.86 (2H, m), 2.08-2.35 (2H, m), 3.50 (2H, t, J=6.2 Hz), 3.83 (2H, t, J=7.3 Hz), 4.41 (2H, t, J=6.2 Hz), 5.23 (2H, s), 5.37 (1H, d, J=17.0 Hz), 5.68 (1H, d, J=17.0 Hz), 7.16 (1H, br.d), 7.22 (1H, s), 7.40 (1H, s), 7.59-7.71 (2H, m)

ESI (LC-MS positive mode) m/z 609, 611 (M+H).

Process 5-B (9S)-9-{2-[(R-2-tert-Butoxycarbonylamino-2-methoxycarbonyl)ethanesulfanyl]ethoxycarbonyloxy}-9-ethyl-1-pentyl-1H,12H-pyrano[3",4":6',7']indolizino [1',2':6,5]pyrido[4,3,2-de]quinazoline-10,13(9H, 15H)-dione

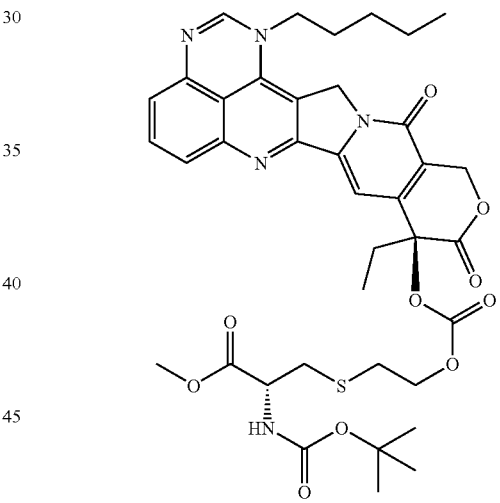

50 mg (0.082 mmol) of (9S)-9-(2-bromo-ethoxycarbonyloxy)-9-ethyl-1-pentyl-1H,12H-pyrano[3",4":6',7']indolizino[1',2':6,5]pyrido[4,3,2-de]quinazoline-10,13(9H, 15H)-dione prepared in Process 5-A, 58 mg (0.25 mmol) of tert-butoxycarbonyl-cysteine methyl ester, and 34 mg (0.25 mmol) of potassium carbonate were stirred in acetonitrile (2 mL), at room temperature for six hours.

Following the addition of methylene chloride to the reaction mixture, the solution was washed with 0.3 N aqueous hydrochloric acid, dried over anhydrous sodium sulfate, and then the solvent was distilled off under reduced pressure. By purifying the obtained residue by silica gel column chromatography (methylene chloride:methanol=50:1), 51 mg (82%) of (9S)-9-{2-[(R-2-tert-butoxycarbonylamino-2-methoxycarbonyl)ethanesulfanyl]ethoxycarbonyloxy}-9-ethyl-1- pentyl-1H,12H-pyrano[3",4":6',7']indolizino[1',2':6,5]pyrido[4,3,2-de]quinazoline-10,13(9H,15H)-dione was obtained as a yellow solid.

¹H-NMR (270 MHz, CDCl₃) δ(ppm): 0.93 (3H, t, J=7.0 Hz), 0.98 (3H, t, J=7.6 Hz), 1.30-1.54 (4H, m), 1.41 (9H, s), 1.68-1.86 (2H, m), 2.05-2.34 (2H, m), 2.78 (2H, t, J=6.8 Hz), 2.89-3.05 (2H, m), 3.71 (3H, s), 3.82 (2H, t, J=7.3 Hz), 4.23 (2H, t, J=6.8 Hz), 4.46 (1H, m), 5.23 (2H, s), 5.37 (1H, d, J=17.0 Hz), 5.42 (1H, m), 5.67 (1H, d, J=17.0 Hz), 7.17 (1H, br.d), 7.22 (1H, s), 7.40 (1H, s), 7.60-7.70 (2H, m)

ESI (LC-MS positive mode) m/z 764 (M+H).
Process 5-C (9S)-9-{2-[(R-2-tert-Butoxycarbonylamino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione

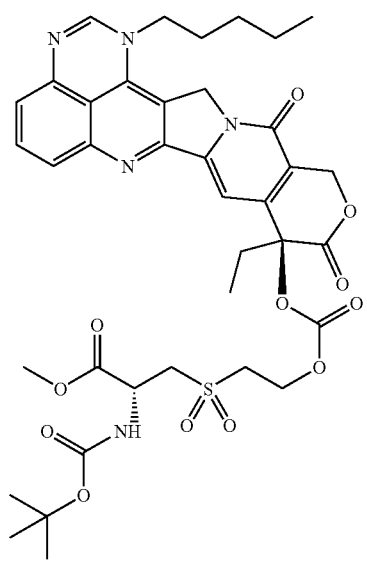

98 mg (0.13 mmol) of (9S)-9-{2-[(R-2-tert-butoxycarbonylamino-2-methoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione produced in Process 5-B, and 158 mg (0.26 mmol) of Oxone™ were stirred in methanol (5 mL) at room temperature for 2.5 hours.

Methylene chloride was added to the reaction mixture, the mixture was washed with water and dried over anhydrous sodium sulfate, and the solvent was distilled off under reduced pressure. By purifying the obtained residue by silica gel column chromatography (methylene chloride:methanol=40:1), 93 mg (92%) of (9S)-9-{2-[(R-2-tert-butoxycarbonylamino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione was obtained as a yellow solid.

ESI (LC-MS positive mode) m/z 796 (M+H).
Process 5-D (9S)-9-{2-[(R-2-Amino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione trifluoroacetate

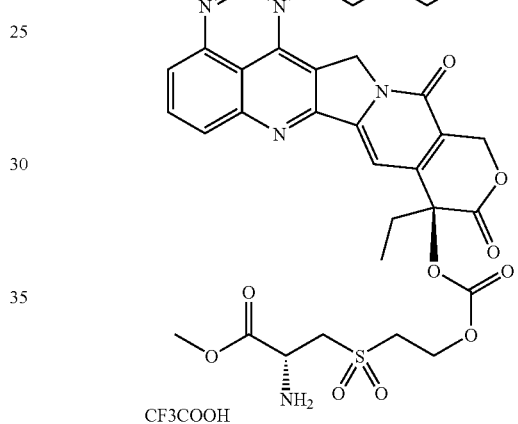

93 mg (0.12 mmol) of (9S)-9-{2-[(R-2-tert-butoxycarbonylamino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione prepared in Process 5-C was dissolved in trifluoroacetic acid (3 mL), and then stirred at room temperature for one hour.

Diethyl ether was added to the reaction solution, and this was stirred at room temperature for 10 minutes. The resulting solid was collected by filtration to yield 88 mg (94%) of (9S)-9-{2-[(R-2-amino-2-methoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione trifluoroacetate (compound 5A) as a yellow solid.

¹H-NMR (270 MHz, CD₃OD) δ(ppm): 0.95 (3H, t, J=7.3 Hz), 1.03 (3H, t, J=7.3 Hz), 1.37-1.56 (4H, m), 1.76-1.92 (2H, m), 2.10-2.28 (2H, m), 3.69-4.05 (6H, m), 3.90 (3H, s), 4.48-4.82 (3H, m), 5.35 (2H, s), 5.48 (1H, d, J=16.8 Hz), 5.64 (1H, d, J=16.8 Hz), 7.13 (1H, br.d), 7.28 (1H, s), 7.56 (1H, d, J=8.3 Hz), 7.71 (1H, m), 7.80 (1H, s)

ESI (LC-MS positive mode) m/z 696 (M+H).

Preparation Example 6

(9S)-9-{2-[(R-2-Amino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H, 15H)-dione hydrochloride (Compound 6A)

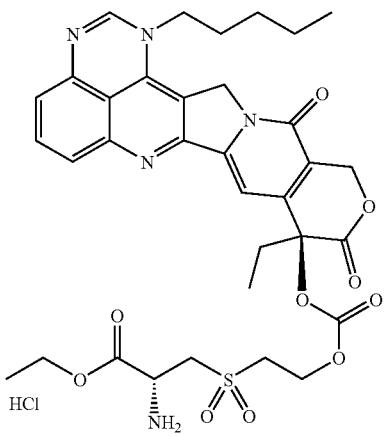

Process 6-A (9S)-9-{2-[(R-2-tert-Butoxycarbonylamino-2-ethoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione

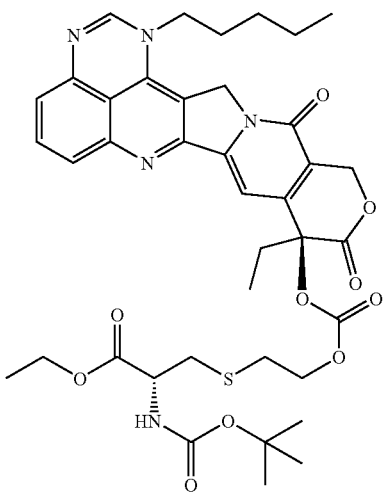

270 mg (0.44 mmol) of (9S)-9-(2-bromo-ethoxycarbonyloxy)-9-ethyl-1-pentyl-1H,12H-pyrano[3",4":6',7']indolizino[1',2':6,5]pyrido[4,3,2-de]quinazoline-10,13(9H, 15H)-dione, 333 mg (1.33 mmol) of tert-butoxycarbonyl-cysteine ethyl ester, and 184 mg (1.33 mmol) of potassium carbonate were stirred in acetonitrile (10 mL) at room temperature for 20 hours.

Following the addition of methylene chloride to the reaction mixture, the mixture was washed with 0.3 N aqueous hydrochloric acid, dried over anhydrous sodium sulfate, and the solvent was distilled off under reduced pressure. By purifying the obtained residue by silica gel column chromatography (methylene chloride:methanol=50:1), 159 mg (46%) of (9S)-9-{2-[(R-2-tert-butoxycarbonylamino-2-ethoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione was obtained as a yellow oil.

$^1$H-NMR (270 MHz, CDCl$_3$) δ(ppm): 0.93 (3H, t, J=7.3 Hz), 0.97 (3H, t, J=7.3 Hz), 1.25 (3H, t, J=7.3 Hz), 1.32-1.53 (4H, m), 1.41 (9H, s), 1.73-1.85 (2H, m), 2.05-2.35 (2H, m), 2.79 (2H, t, J=6.9 Hz), 2.88-3.05 (2H, m), 3.83 (2H, t, J=7.3 Hz), 4.09-4.28 (4H, m), 4.43 (1H, m), 5.23 (2H, s), 5.37 (1H, d, J=17.2 Hz), 5.43 (1H, m), 5.67 (1H, d, J=17.2 Hz), 7.17 (1H, br.d), 7.21 (1H, s), 7.40 (1H, s), 7.60-7.70 (2H, m)

ESI (LC-MS positive mode) m/z 778 (M+H).

Process 6-B (9S)-9-{2-[(R-2-tert-Butoxycarbonylamino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H,15H)-dione

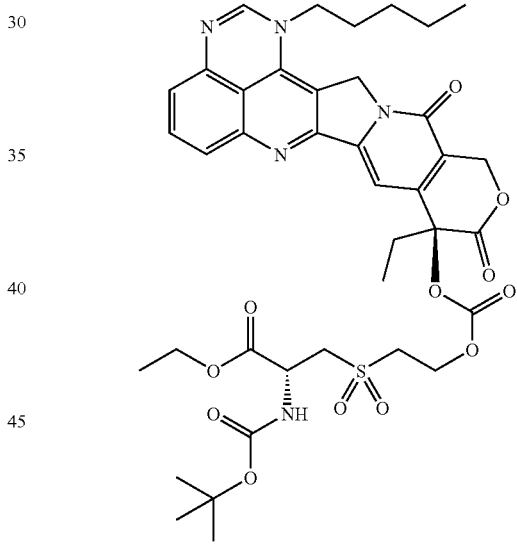

159 mg (0.20 mmol) of (9S)-9-{2-[(R-2-tert-butoxycarbonylamino-2-ethoxycarbonyl)ethanesulfanyl]ethoxycarbonyloxy}-9-ethyl-1-pentyl-1H,12H-pyrano[3",4":6',7']indolizino[1',2':6,5]pyrido[4,3,2-de]quinazoline-10,13(9H, 15H)-dione prepared in Process 6-A and 252 mg (0.41 mmol) of Oxone™ were stirred in methanol (8 mL) at room temperature for two hours.

Following the addition of methylene chloride to the reaction mixture, the mixture was washed with water and dried over anhydrous sodium sulfate, and the solvent was distilled off under reduced pressure. By purifying the obtained residue by silica gel column chromatography (methylene chloride:methanol=40:1), 141 mg (88%) of (9S)-9-{2-[(R-2-tert-butoxycarbonylamino-2-ethoxycarbonyl)ethanesulfonyl]ethoxycarbonyloxy}-9-ethyl-1-pentyl-1H,12H-pyrano[3", 4":6',7']indolizino[1',2':6,5]pyrido[4,3,2-de]quinazoline-10, 13(9H,15H)-dione was obtained as a yellow solid.

¹H-NMR (270 MHz, CDCl₃) δ(ppm): 0.93 (3H, t, J=6.9 Hz), 0.99 (3H, t, J=7.6 Hz), 1.29 (3H, t, J=7.3 Hz), 1.32-1.55 (4H, m), 1.45 (9H, s), 1.72-1.87 (2H, m), 2.07-2.32 (2H, m), 3.25-3.52 (2H, m), 3.73 (2H, m), 3.84 (2H, t, J=7.3 Hz), 4.23 (2H, q, J=7.3 Hz), 4.55 (2H, br.t), 4.71 (1H, m), 5.25 (2H, s), 5.37 (1H, d, J=17.2 Hz), 5.69 (1H, d, J=17.2 Hz), 5.76 (1H, d, J=7.9 Hz), 7.18 (1H, br.d), 7.19 (1H, s), 7.40 (1H, s), 7.61-7.72 (2H, m)

ESI (LC-MS positive mode) m/z 810 (M+H).

Process 6-C (9S)-9-{2-[(R-2-Amino-2-ethoxycarbonyl)ethanesulfonyl]ethoxycarbonyloxy}-9-ethyl-1-pentyl-1H, 12H-pyrano[3",4":6',7']indolizino[1',2':6,5]pyrido[4, 3,2-de]quinazoline-10,13(9H,15H)-dione hydrochloride

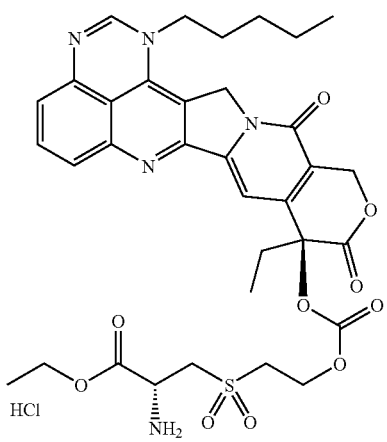

140 mg (0.17 mmol) of (9S)-9-{2-[(R-2-tert-butoxycarbonylamino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H, 15H)-dione prepared in Process 6-B was dissolved in 1N hydrochloric acid-acetic acid solution (5 mL), and then stirred at room temperature for one hour.

Ethyl acetate was added to the reaction solution, and stirred at room temperature for 30 minutes. The resulting solid was collected by filtration to yield 127 mg (94%) of (9S)-9-{2-[(R-2-amino-2-ethoxycarbonyl)ethanesulfonyl]ethoxycarbonyloxy}-9-ethyl-1-pentyl-1H,12H-pyrano[3",4":6',7']indolizino[1',2':6,5]pyrido[4,3,2-de]quinazoline-10,13(9H, 15H)-dione hydrochloride (compound 6A) as a yellow solid.

¹H-NMR (400 MHz, CD₃OD) δ(ppm): 0.99 (3H, t, J=7.6 Hz), 1.04 (3H, t, J=7.2 Hz), 1.36 (3H, t, J=7.2 Hz), 1.40-1.60 (4H, m), 1.92-2.00 (2H, m), 2.10-2.25 (2H, m), 3.70-3.86 (3H, m), 4.10 (1H, dd, J=15.2, 4.0 Hz), 4.25 (2H, t, J=8.0 Hz), 4.36 (2H, q, J=7.6 Hz), 4.60 (2H, t, J=5.2 Hz), 4.77 (1H, m), 5.52 (1H, d, J=16.8 Hz), 5.54 (2H, s), 5.65 (1H, d, J=16.8 Hz), 7.54 (1H, d, J=7.6 Hz), 7.83 (1H, s), 7.91 (1H, d, J=8.0 Hz), 8.09 (1H, br.t), 8.38 (1H, s)

ESI (LC-MS positive mode) m/z 710 (M+H).

Preparation Example 7

(9S)-9-[2-(2-Aminoethanesulfonyl)ethoxycarbonyloxy]-9-ethyl-1-pentyl-1H,12H-pyrano[3",4": 6',7']indolizino[1',2':6,5]pyrido[4,3,2-de]quinazoline-10, 13(9H,15H)-dione hydrochloride (Compound 7A)

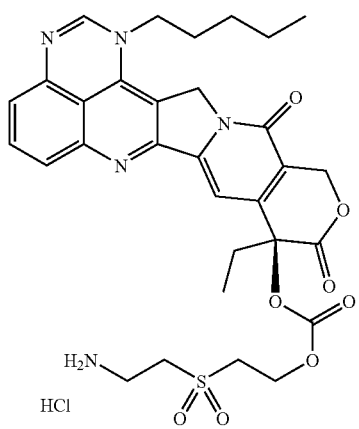

Process 7-A (9S)-9-[2-(2-tert-Butoxycarbonylaminoethanesulfonyl)ethoxycarbonyloxy]-9-ethyl-1-pentyl-1H, 12H-pyrano[3",4":6',7']indolizino[1',2':6,5]pyrido[4, 3,2-de]quinazoline-10,13(9H,15H)-dione

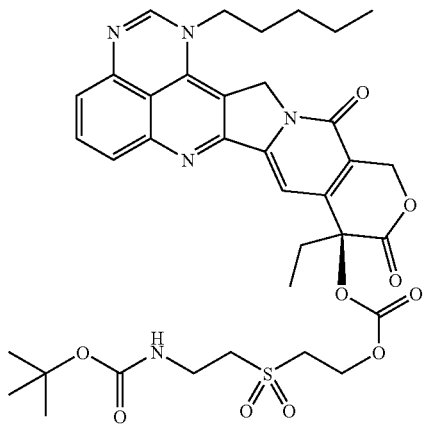

825 mg (1.8 mmol) of (9S)-9-ethyl-9-hydroxy-1-pentyl-1H,12H-pyrano[3",4":6',7']indolizino[1',2':6,5]pyrido[4,3, 2-de]quinazoline-10,13(9H,15H)-dione, 543 mg (2.7 mmol) of p-nitrophenyl chloroformate, 0.47 mL (2.7 mmol) of diisopropyl-ethylamine, and 220 mg (1.8 mmol) of 4-dimethylaminopyridine were dissolved in methylene chloride (16 mL) on ice, and then stirred at room temperature for three hours. Next, 1.6 g (6.3 mmol) of 2-(2-tert-butoxycarbonylaminoethanesulfonyl)ethanol (Tetrahedron, 55 (1999), 6623-6634) was added to this solution, and this was stirred at room temperature for approximately 24 hours.

The reaction solution was washed with 0.3 N aqueous hydrochloric acid, dried over anhydrous sodium sulfate, and then the solvent was distilled off under reduced pressure. By purifying the obtained residue by silica gel column chromatography (methylene chloride methanol=30:1), 550 mg (42%) of (9S)-9-[2-(2-tert-butoxycarbonylaminoethanesulfonyl)ethoxycarbonyloxy]-9-ethyl-1-pentyl-1H,12H-pyrano[3",4":6',7']indolizino[1',2':6,5]pyrido[4,3,2-de]quinazoline-10,13(9H,15H)-dione was obtained as a yellow solid.

$^1$H-NMR (270 MHz, CDCl$_3$) δ(ppm): 0.94 (3H, t, J=7.3 Hz), 1.00 (3H, t, J=7.3 Hz), 1.33-1.55 (4H, m), 1.43 (9H, s), 1.73-1.86 (2H, m), 2.07-2.31 (2H, m), 3.20-3.49 (4H, m), 3.70 (2H, m), 3.84 (2H, t, J=7.3 Hz), 4.57 (2H, br.t), 5.25 (2H, s), 5.37 (1H, d, J=17.2 Hz), 5.45 (1H, m), 5.69 (1H, d, J=17.2 Hz), 7.15-7.20 (2H, m), 7.41 (1H, s), 7.61-7.73 (2H, m)

ESI (LC-MS positive mode) m/z 738 (M+H).

Process 7-B (9S)-9-[2-(2-Aminoethanesulfonyl)ethoxycarbonyloxy]-9-ethyl-1-pentyl-1H,12H-pyrano[3",4":6',7'] indolizino[1',2':6,5]pyrido[4,3,2-de]quinazoline-10, 13(9H,15H)-dione hydrochloride

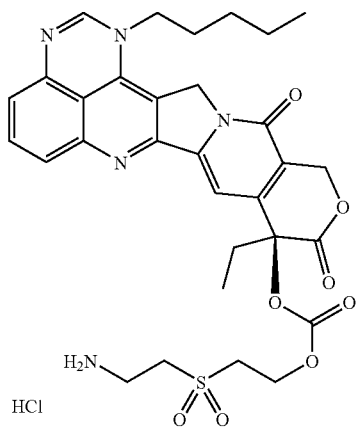

530 mg (0.72 mmol) of (9S)-9-[2-(2-tert-butoxycarbonylaminoethanesulfonyl)ethoxycarbonyloxy]-9-ethyl-1-pentyl-1H,12H-pyrano[3",4":6',7']indolizino[1',2':6,5]pyrido[4,3,2-de]quinazoline-10,13(9H,15H)-dione prepared in Process 7-A was dissolved in 1 N hydrochloric acid-acetic acid solution (10 mL), and then stirred at room temperature for one hour.

Ethyl acetate was added to the reaction solution, which was then stirred at room temperature for 30 minutes, and the resulting solid was collected by filtration to yield 480 mg (94%) of (9S)-9-[2-(2-aminoethanesulfonyl)ethoxycarbonyloxy]-9-ethyl-1-pentyl-1H,12H-pyrano[3",4":6',7']indolizino[1',2':6,5]pyrido[4,3,2-de]quinazoline-10,13(9H, 15H)-dione hydrochloride (compound 7A) as a yellow solid.

$^1$H-NMR (270 MHz, CD$_3$OD) δ(ppm): 0.94-1.05 (6H, m), 1.40-161 (4H, m), 1.90-2.04 (2H, m), 2.07-2.28 (2H, m), 3.48-3.81 (6H, m), 4.25 (2H, br.t), 4.55 (2H, m), 5.51 (1H, d, J=17.2 Hz), 5.53 (2H, s), 5.65 (1H, d, J=17.2 Hz), 7.52 (1H, d, J=7.6 Hz), 7.90 (1H, s), 7.93 (1H, d, J=8.6 Hz), 8.08 (1H, br.t), 8.35 (1H, s)

ESI (LC-MS positive mode) m/z 638 (M+H).

Example 1

Effect of Combining Compound 10A (Active Form of Compound 2A Prepared in Preparation Example 2) with Other Cytotoxic Substances in the Human Lung Cancer Cell Line Calu-6 Human Stomach Cancer Cell Lines MKN-28 and MKN-45 and Human Ovarian Cancer Cell Line OVCAR-3

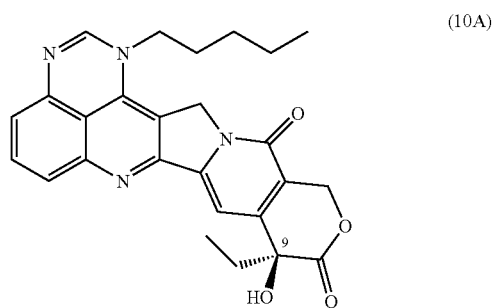

(10A)

Cell Cultures

The human lung cancer cell line Calu-6 and human ovarian cancer cell line OVCAR-3 were purchased from American Type Culture Collection (ATCC), and the human stomach cancer cell lines MKN-28 and MKN-45 were purchased from Immuno-Biological Laboratories (IBL). The human lung cancer cell line Calu-6 was monolayer cultured in E-MEM medium supplemented with 0.1 mM nonessential amino acids, 1 mM sodium pyruvate, and 10% (v/v) fetal bovine serum; the human ovarian cancer cell line OVCAR-3 was monolayer cultured in RPMI1640 medium containing 20% (v/v) fetal bovine serum; and the human stomach cancer cell lines MKN-28 and MKN-45 were separately monolayer cultured in RPMI1640 medium containing 10% (v/v) fetal bovine serum.

The following were prepared as test reagents.

Test Reagents

Compound A: Compound 10A ((9S)-9-ethyl-9-hydroxy-1-pentyl-1H,12H-pyrano [3",4":6',7']indolizino[1',2':6,5]pyrido[4,3,2-de] quinazoline-10,13(9H,15H)-dione) was synthesized according to known methods (Example 2.15 of WO 2003/045952).

Compound B: CDDP (cisplatin) (compound 1B), 5-FU (active form of capecitabine (compound 6B)) (compound 2B), gemcitabine (compound 3B), paclitaxel (compound 4B), and vinorelbine (compound 5B).

Concentration of Pharmaceuticals Used for the Human Lung Cancer Cell Line Calu-6:

Compound 10A: 20 nmol/L to 0.3125 nmol/L,
CDDP: 4 μmol/L to 0.0156 μmol/L,
5-FU: 200 μmol/L to 0.7813 μmol/L,
gemcitabine: 80 nmol/L to 0.3125 nmol/L,
paclitaxel: 30 nmol/L to 0.1172 nmol/L, and vinorelbine: 40 nmol/L to 0.1563 nmol/L.

Concentration of Pharmaceuticals Used for the Human Ovarian Cancer Cell Line OVCAR-3 and the Human Stomach Cancer Cell Line MKN-28:

Compound 10A: 400 nmol/L to 6.25 nmol/L, and

CDDP: 42 µmol/L to 0.1641 µmol/L.
Concentration of Pharmaceuticals Used for the Human Stomach Cancer Cell Line MKN-45:
Compound 10A: 4 nmol/L to 0.0625 nmol/L, and
CDDP: 4 µmol/L to 0.0156 µmol/L.
Each of the pharmaceuticals was dissolved in DMSO and then diluted with the medium.

Method for Evaluating Antiproliferative Activity

Anti-cell proliferative activity of the pharmaceuticals was tested as follows. On the first day, 190 µL of a single cell suspension (3000 cells per well) was plated in 96-well plates, and the cells were cultured at 37° C. in a humidified incubator containing 5% $CO_2$. On the following day, 10 mL solutions containing single pharmaceuticals or a mixture of compound 10A and compounds 1B to 5B at various mixing ratios were added to the 96-well plates cultured overnight. This was cultured at 37° C. for three more days in a humidified incubator containing 5% $CO_2$. On the last day of culturing, 10 µL of Cell Counting Kit-8 was added to each well, and then the cells were incubated for another few hours at 37° C. in a humidified incubator containing 5% $CO_2$. After incubation, the absorbance at 450 nm and 630 nm was measured in each well using a Microplate Reader (BIO-RAD Model 3550). The anti-cell proliferative activity of each pharmaceutical was calculated by the equation $(1-T/C)\times 100(\%)$ (T and C represent the average difference between the absorbances at 450 nm and 630 nm in pharmaceutical-treated cells and untreated control cells, respectively).

Results

Figures 1, 2:
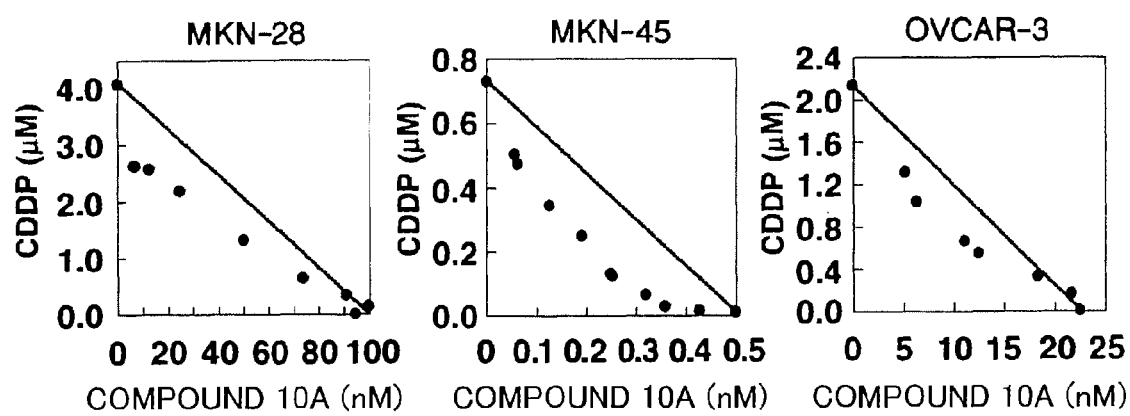
Figures 1, 2:
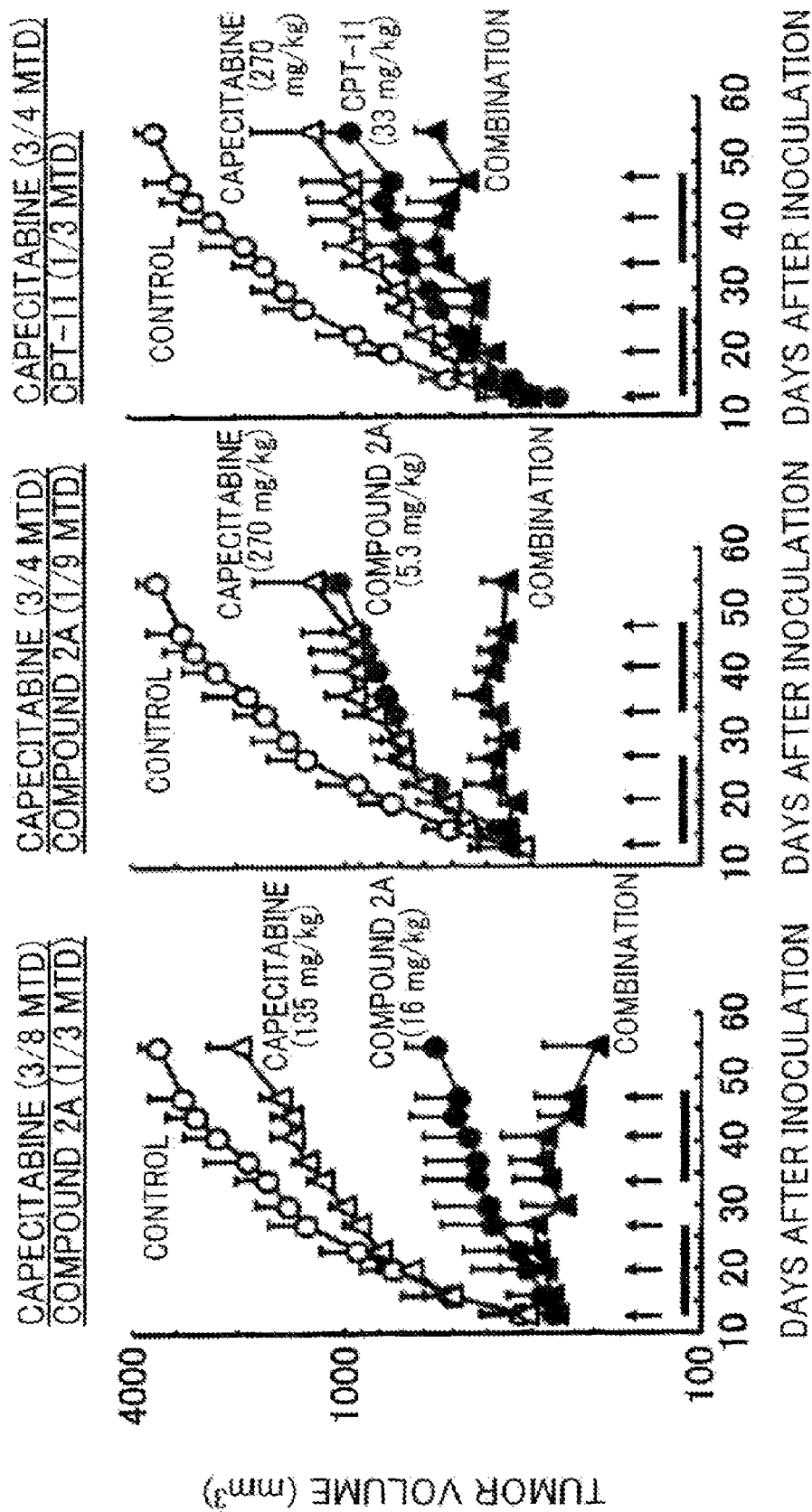
Figure 2:
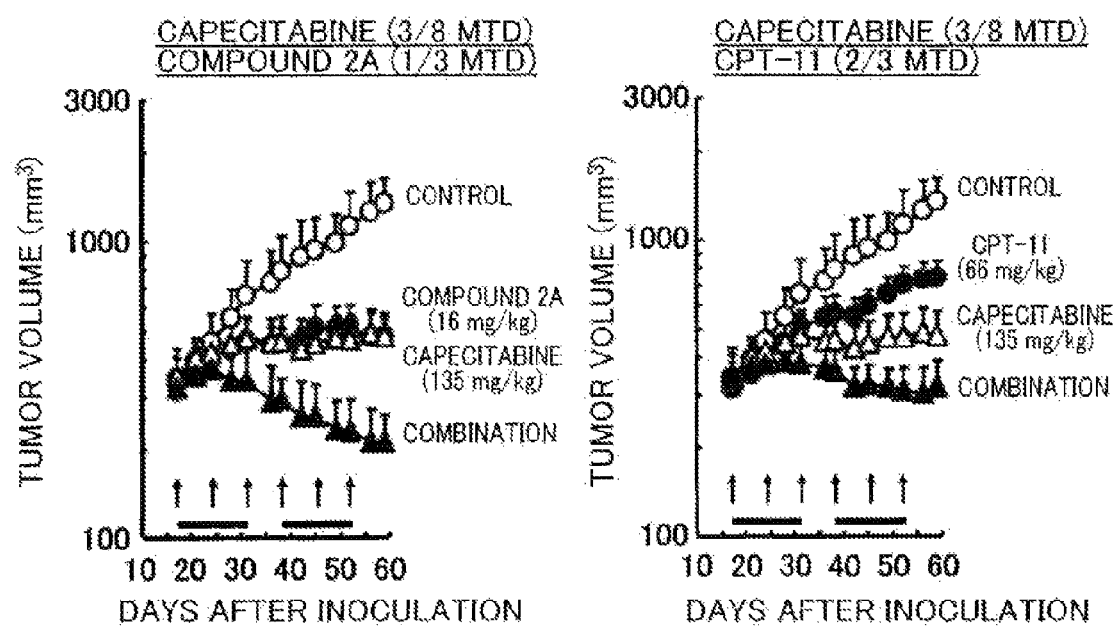

As a result, as indicated in FIGS. 1-1 and 1-2, the combination of compound 10A and compound 1B showed a marked synergistic effect according to results of isobologram analyses. Significant effects were also observed with the combinations of compound 10A and compounds 2B to 5B.

Example 2

Antitumor Effect of the Combination of a Water-Soluble Prodrug (Compound 2A) and Capecitabine (Compound 6B) in Human Colorectal Cancer and Stomach Cancer Xenograft Models (Dosage Regimen: Administration of Compound 2A Once a Week; and Daily Administration of Capecitabine for Two Consecutive Weeks then No Administration for One Week)

Cell Cultures

As for the cells, the human colorectal cancer cell line HCT116 and the human stomach cancer cell line NCI-N87 were purchased from ATCC. HCT116 cells were monolayer cultured in McCoy's 5a medium containing 2 mM L-glutamine and 10% (v/v) fetal bovine serum, and NCI-N87 cells were monolayer cultured in RPMI1640 medium containing 10% (v/v) fetal bovine serum.

Generation of Xenograft Models

Five-week old male athymic nude mice (BALB/c nu/nu) purchased from Charles River Japan were used for the experiments. The mice were reared for at least one week prior to the experiment at the animal facility of the research institute.

Single cell suspensions of HCT116 ($7.5\times 10^6$ cells per mouse) and NCI-N87 ($5.9\times 10^6$ cells per mouse) cultured as described above were inoculated subcutaneously into the right side of the abdomen of each mouse. The tumor size of each mouse was measured once or twice a week and the tumor volume was estimated using the formula $ab^2/2$ (a and b refer to the length and width of the tumor, respectively). Randomization and administration of pharmaceuticals were begun the day the tumor volume exceeded 100 $mm^3$.

Test Reagents

Compound 2A synthesized according to Preparation Example 2 and capecitabine (compound 6B) synthesized according to known methods (Japanese Patent No. 2501297) were used as test reagents, and CPT-11 (irinotecan (a camptothecin); Daiichi Pharmaceuticals) was used as a control for compound A. The dosage is as shown below. In the present description, "MTD" refers to (maximum tolerated dose).

HCT116 model: compound 2A: 6.7 mg/kg/injection (5.3 mg/kg/injection as free base) (⅙ MTD) and 20 mg/kg/injection (16 mg/kg/injection as free base) (⅓ MTD); CPT-11: 33 mg/kg/injection (⅓ MTD); capecitabine (compound 6B): 135 mg/kg/injection (⅜ MTD) and 270 mg/kg/injection (¾ MTD).

NCI-N87 model: compound 2A: 20 mg/kg/injection (16 mg/kg/injection as free base) (⅓ MTD); CPT-11: 66 mg/kg/injection (⅔ MTD); capecitabine (compound 6B): 135 mg/kg/injection (⅜ MTD).

Method for Administering a Single Agent

Compound 2A and CPT-11 were each dissolved and diluted in a saline solution. Capecitabine (compound 6B) was dissolved and diluted in 40 mM citric acid buffer (pH6) containing 5% gum arabic. Compound 2A and CPT-11 were intravenously administered once a week for six consecutive weeks. Capecitabine was orally administered once a day for two consecutive weeks, and then medication was discontinued for one week (i.e. once a day for 14 days during the three-week period).

Method for Administering a Mixture

The antitumor effect of the combination of compound 2A and capecitabine (compound 6B) and the antitumor effect of the combination of CPT-11 and capecitabine (compound 6B) were compared using HCT116 and NCI-N87 human cancer xenograft models. In one therapeutic cycle, compound 2A or CPT-11 was administered once a week for three consecutive weeks; and capecitabine (compound 6B) was administered once a day for two consecutive weeks, then medication was discontinued for one week (i.e. once a day for 14 days during the three-week period). The mice were subjected to two therapeutic cycles.

Results

Results for each xenograft model are shown in FIG. 2-1 (HCT116 model) and FIG. 2-2 (NCI-N87 model).

In both models, the antitumor effect of the combination of compound 2A and capecitabine (compound 6B) was stronger than the effects observed with single agents at the same dosage. Furthermore, in the xenograft models HCT116 (FIG. 2-1) and NCI-N87 (FIG. 2-2), the combination of compound 2A and capecitabine (compound 6B) showed an additive antitumor effect without enhancing toxicity as determined from the weight reduction.

Furthermore, in all the xenograft models tested, the antitumor effect of the combination of compound 2A and capecitabine (compound 6B) is superior to the antitumor effect of the combination of CPT-11 and capecitabine (compound 6B). Thus, the antitumor effect of the combination of compound 2A and capecitabine (compound 6B) is significant, and it is expected to become an effective combination therapy in clinical practice.

Example 3

Antitumor Effect of the Combination of a
Water-Soluble Prodrug (Compound 2A) and
Capecitabine (Compound 6B) in the Human
Colorectal Cancer HCT116 Xenograft Model
(Dosing Regimen: One Administration of Compound
2A During a Three-Week Period; and Daily
Administration of Capecitabine for Two Consecutive
Weeks, then No Administration for One Week)

Cell Growth

The human colorectal cancer cell line HCT116 was purchased from ATCC. Cells were monolayer cultured in McCoy's 5a medium containing 2 mM L-glutamine and 10% (v/v) fetal bovine serum.

Generation of Xenograft Models

Five-week old male athymic nude mice (BALB/c nu/nu) were purchased from Charles River Japan. The mice were reared for at least one week prior to the experiment at the animal facility of the research institute.

A single cell suspension of HCT116 ($8 \times 10^6$ cells per mouse) was inoculated subcutaneously into the right side of the abdomen of each mouse. The tumor size of each mouse was measured twice a week and the tumor volume was estimated using the $ab^2/2$ formula (a and b refer to the length and width of the tumor, respectively). Randomization and administration pharmaceuticals were begun the day the tumor volume exceeded 100 mm$^3$ Test Reagents Compound 2A and capecitabine (compound 6B) prepared in the same manner as in Example 2 were used. The dosage is as follows.

Dosage:

compound 2A: 20 mg/kg/injection (16 mg/kg/injection as free base) (⅓ MTD), 40 mg/kg/injection (32 mg/kg/injection as free base) (⅔ MTD), and 60 mg/kg/injection (47 mg/kg/injection as free base) (MTD);

capecitabine: 180 mg/kg/injection (½ MTD) and 360 mg/kg/injection (MTD).

Method of Administration

Compound 2A was dissolved and diluted in a saline solution. Capecitabine was dissolved and diluted in 40 mM citric acid buffer (pH6) containing 5% gum arabic. Compound 2A was intravenously administered once during a three-week period. Capecitabine was orally administered once a day for two consecutive weeks, then medication was discontinued for one week (i.e. once a day for 14 days during the three-week period).

Results

The antitumor effect of the combination of compound 2A and capecitabine was examined using the human colorectal cancer HCT116 xenograft model. In one therapeutic cycle, compound 2A was administered on the first day of the three-week period, and capecitabine was administered once a day for two consecutive weeks, then not administered for one week (i.e. administered once a day for 14 days during the three-week period). The mice were subjected to two therapeutic cycles.

Figure 3:
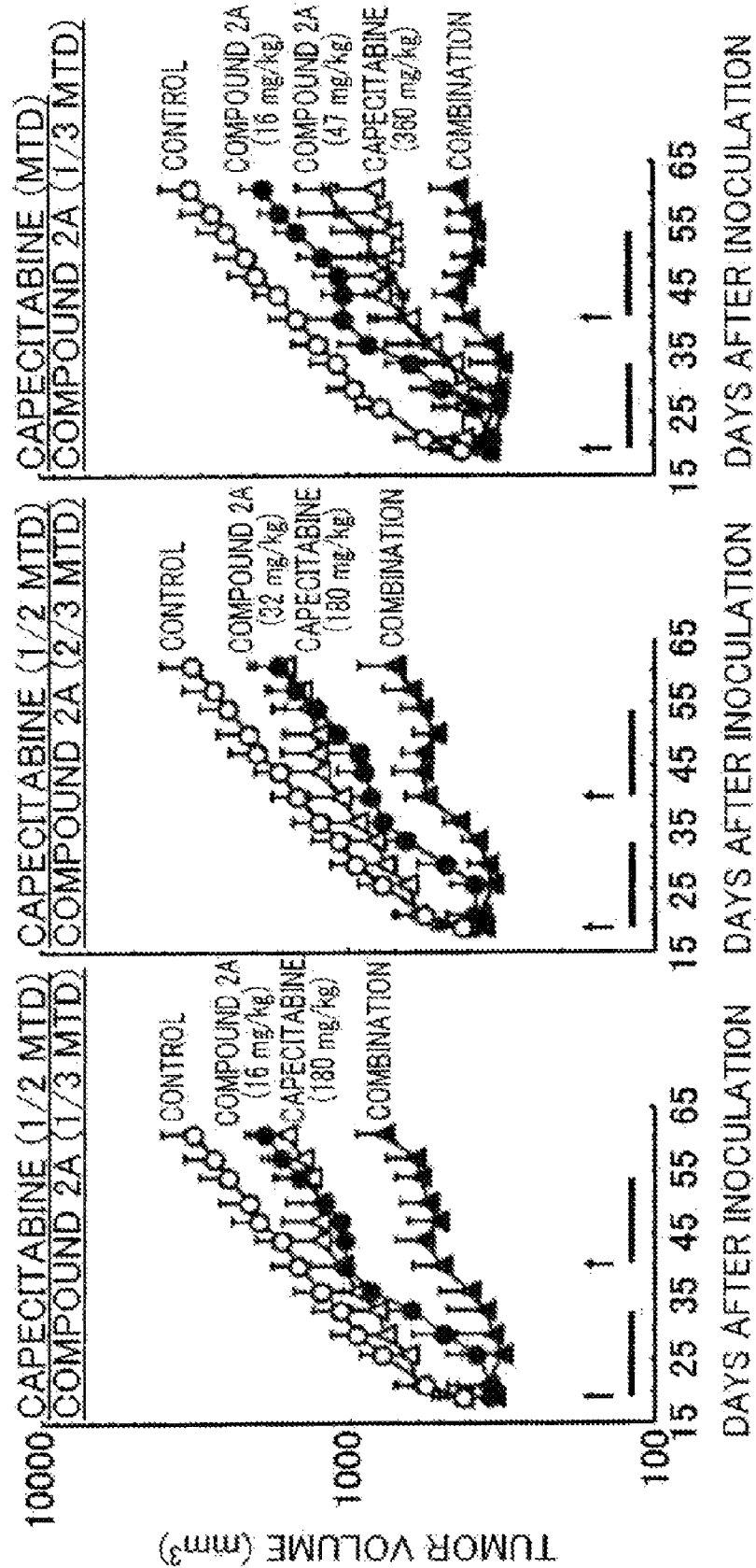
FIG. 3 shows the antitumor activity when the MTD was varied in single or combination therapy using compound 2A and capecitabine (compound 6B) in the human colorectal cancer HCT116 xenograft model. The arrows indicate the days that compound 2A was administered, and the horizontal bars on the X axis indicate the days that capecitabine was administered. The vertical bars at each point indicate standard deviation. Symbols in the graph are the following: capecitabine: open triangles; compound 2A: filled circles; combination: filled triangles; and vehicle: open circles. Each group consisted of six mice, and the tumor volume is their average.

As shown in FIG. 3, the antitumor effect of the combination of compound 2A and capecitabine (compound 6B) was stronger than the effects observed with single agents at the same dosage. Furthermore, in the HCT116 xenograft model, the combination of compound 2A and capecitabine (compound 6B) showed an additive antitumor effect without enhancing toxicity as determined from the weight reduction. Furthermore, the antitumor effect of the combination of compound 2A at ⅓ MTD and capecitabine at MTD was superior to the effect of compound 2A at MTD (FIG. 3). Thus, combined use of compound 2A with capecitabine has a significant effect and was more effective than the use of a single agent at MTD. Therefore, it is expected to become an effective combination therapy in clinical practice.

Example 4

Antitumor Effect of the Combination of a
Water-Soluble Prodrug (Compound 2A) with CDDP
or Carboplatin in the Human Lung Cancer Calu-6
Xenograft Model Cell Growth The human lung cancer cell line Calu-6 was purchased from ATCC. Cells were monolayer cultured in E-MEM supplemented with 0.1 mM nonessential amino acids, 1 mM sodium pyruvate, and 10% (v/v) fetal bovine serum.

Generation of Xenograft Models

Five-week old male athymic nude mice (BALB/c nu/nu) were purchased from Charles River Japan. The mice were reared for at least one week prior to the experiment at the animal facility of the research institute.

A single cell suspension of Calu-6 ($5 \times 10^6$ cells per mouse) was inoculated subcutaneously into the right side of the abdomen of each mouse. The tumor size of each mouse was measured twice a week and the tumor volume was estimated using the $ab^2/2$ formula (a and b refer to the length and width of the tumor, respectively). Randomization and administration of pharmaceuticals were begun the day the tumor volume exceeded 100 mm$^3$ Test Reagents Compound 2A was prepared in the same manner as in Example 2. CPT-11, CDDP, and carboplatin were purchased from Daiichi Pharmaceuticals, Nippon Kayaku, and Bristol-Meyers Squibb, respectively.

Dosage:

compound 2A: 15 mg/kg/injection (12 mg/kg/injection as free base) (¼ MTD) and 30 mg/kg/injection (24 mg/kg/injection as free base) (½ MTD); CPT-11: 50 mg/kg/injection (½ MTD); CDDP: 5 mg/kg/injection (½ MTD); and carboplatin: 50 mg/kg/injection (MTD).

Method of Administration

Compound 2A, CPT-11, CDDP, and carboplatin were dissolved and diluted in a saline solution. Compound 2A and CPT-11 were intravenously administered once a week for six consecutive weeks. CDDP and carboplatin were intravenously administered once in a three-week period.

Results

The antitumor effect of the combination of compound 2A with CDDP or carboplatin was examined using the human lung cancer Calu-6, and compared to the effects of the combination of CPT-11 and CDDP and the combination of CPT-11 and carboplatin. In one therapeutic cycle, compound 2A and CPT-11 were administered once a week for three consecutive weeks, and CDDP and carboplatin were administered once in the three-week period. The mice were subjected to two therapeutic cycles.

Figures 1, 4:
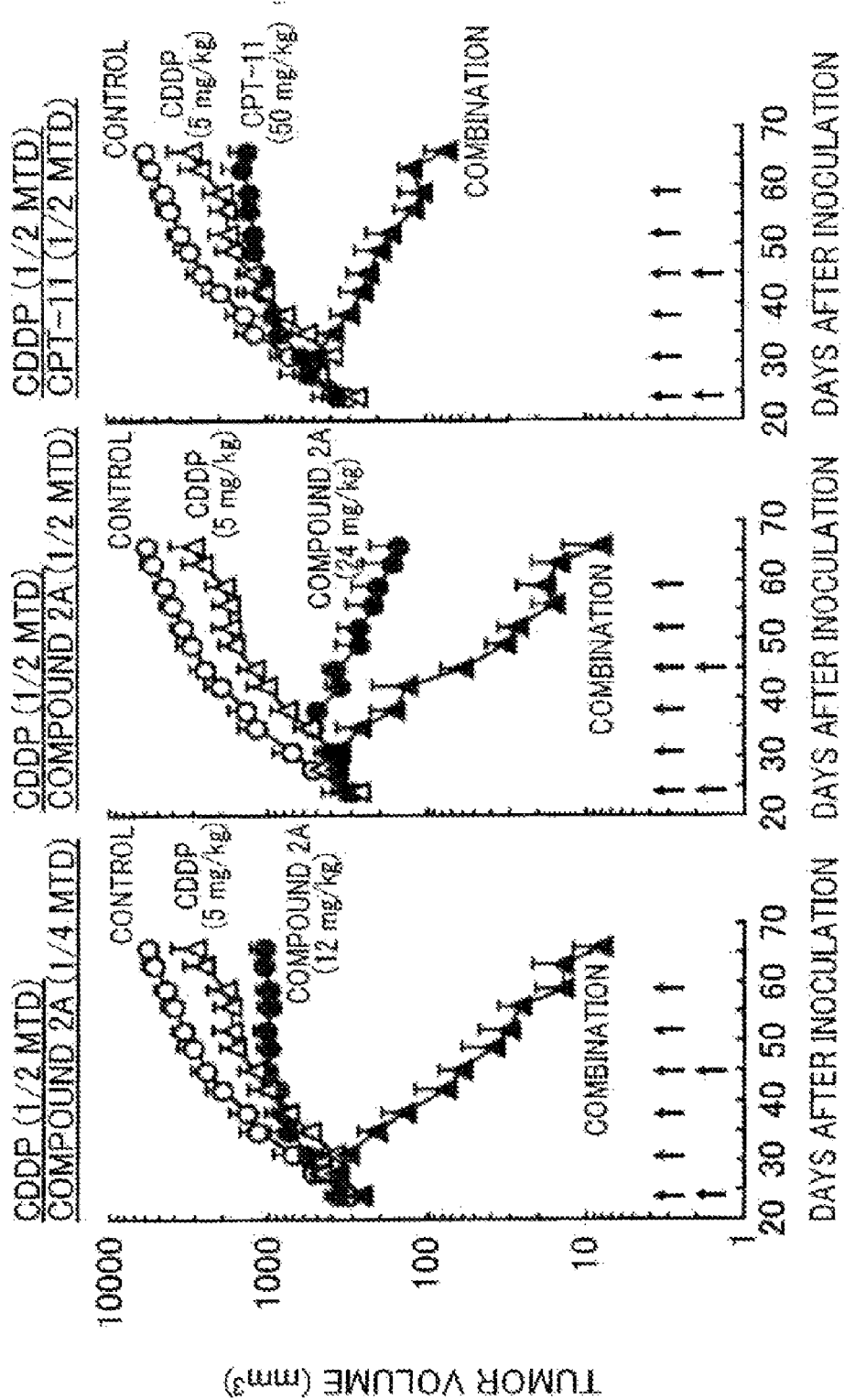
Figures 2, 4:
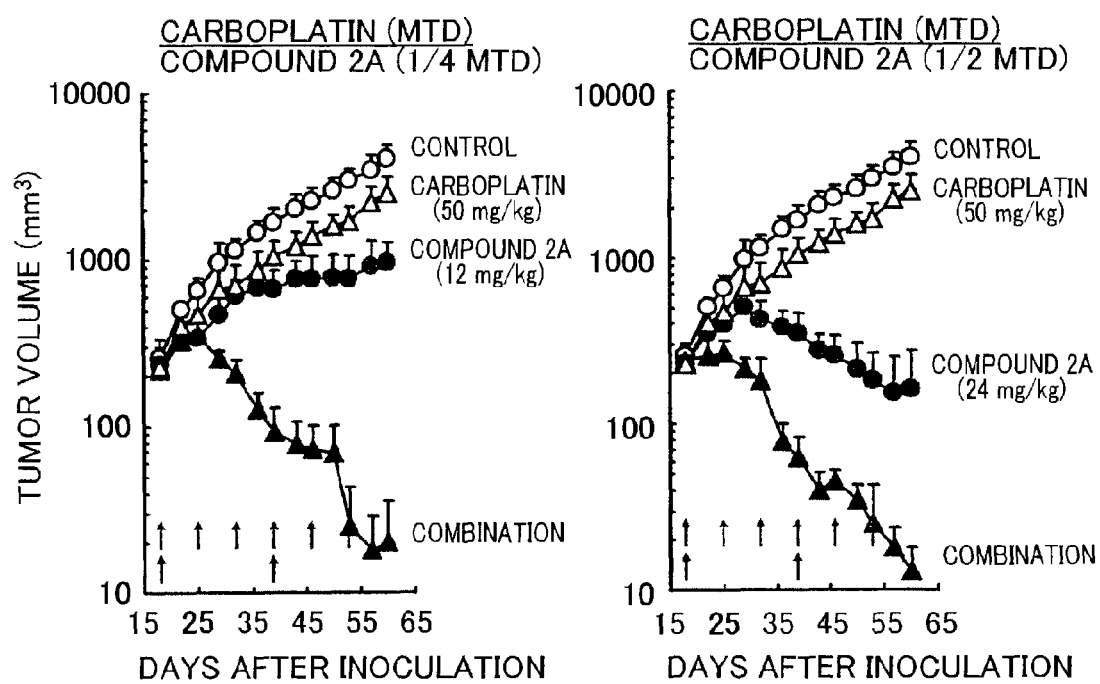

As shown in FIG. 4-1, the antitumor effect of the combination of compound 2A and CDDP was stronger than the effects observed with single agents at the same dosage. The combination of compound 2A and CDDP showed a synergistic antitumor effect without enhancing toxicity as determined from the weight reduction. Furthermore, in this model, the antitumor effect of the combination of compound 2A and CDDP was superior to the effect of the combination of CPT-11 and CDDP.

As shown in FIG. 4-2, a significant synergistic effect of the antitumor effect was also produced in the human lung cancer Calu-6 xenograft model with the combination of compound 2A and carboplatin.

Therefore, the combination of compound 2A and CDDP or carboplatin is expected to become an effective combination therapy in clinical practice.

Example 5

Antitumor Effect of the Combination of a Water-Soluble Prodrug (Compound 2A) and Oxaliplatin in the Human Rectal Cancer COL-16-JCK Xenograft Model Human Tumor Human rectal cancer COL-16-JCK was purchased from Central Institute for Experimental Animals. Tumor sections were inoculated subcutaneously and maintained as xenografts.

Generation of Xenograft Models

Five-week old male athymic nude mice (BALB/c nu/nu) were purchased from Charles River Japan. The mice were reared for at least one week prior to the experiment at the animal facility of the research institute.

A tumor section of COL-16-JCK (approximately 3 mm in diameter) was inoculated subcutaneously into the right side of the abdomen of each mouse. The tumor size of each mouse was measured once or twice a week and the tumor volume was estimated using the $ab^2/2$ formula (a and b refer to the length and width of the tumor, respectively). Randomization and administration of pharmaceuticals were begun the day the tumor volume exceeded 100 mm³

Test Reagents

Compound 2A was prepared in the same manner as in Example 2. Oxaliplatin was purchased from Sanofi-Synthelabo Inc.

Dosage:

compound 2A: 15 mg/kg/injection (12 mg/kg/injection as free base) (¼ MTD) and 30 mg/kg/injection (24 mg/kg/injection as free base) (½ MTD) when administered once a week, or 20 mg/kg/injection (16 mg/kg/injection as free base) (⅓ MTD) and 40 mg/kg/injection (32 mg/kg/injection as free base) (⅔ MTD) when administered once in two weeks; oxaliplatin: 5 mg/kg/injection (½ MTD).

Method of Administration

Compound 2A was dissolved and diluted in a saline solution. Oxaliplatin was dissolved and diluted in 5% glucose. Compound 2A was intravenously administered once a week or once in two weeks for six consecutive weeks. Oxaliplatin was intravenously administered once in two weeks.

Results

The antitumor effect of the combination of compound 2A and oxaliplatin was examined using the human rectal cancer COL-16-JCK xenograft model. Compound 2A was administered once a week or once in two weeks for six consecutive weeks. Oxaliplatin was administered once in two weeks.

Figures 1, 5:
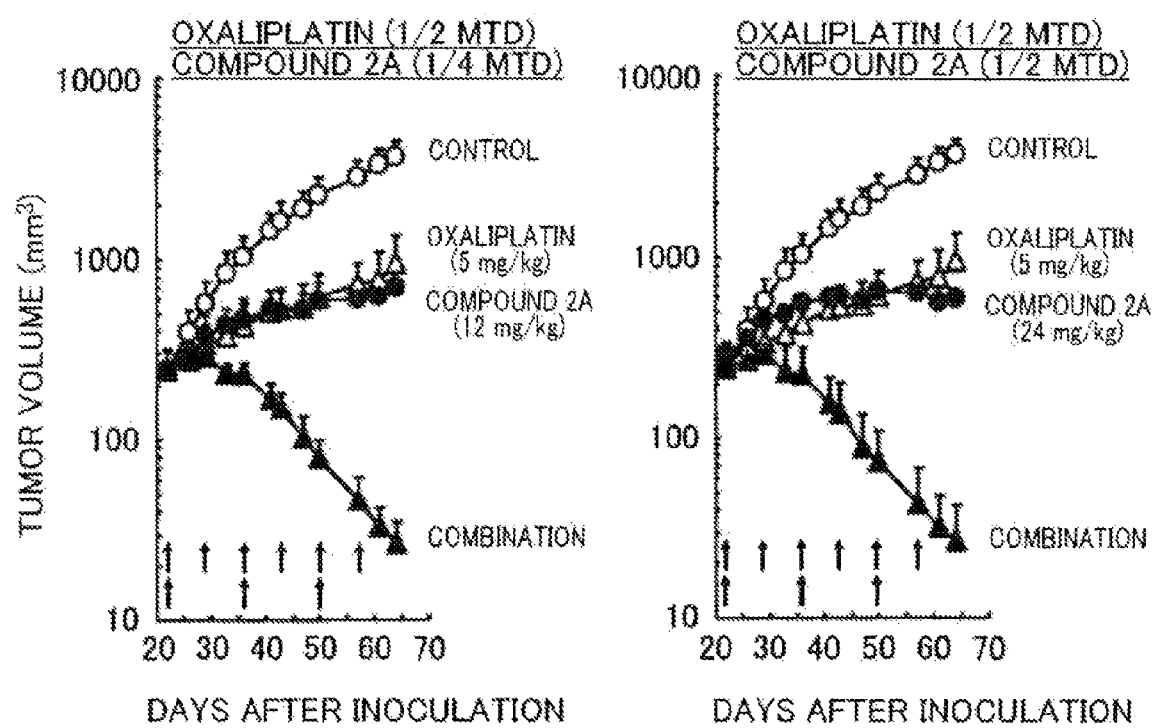
Figures 2, 5:
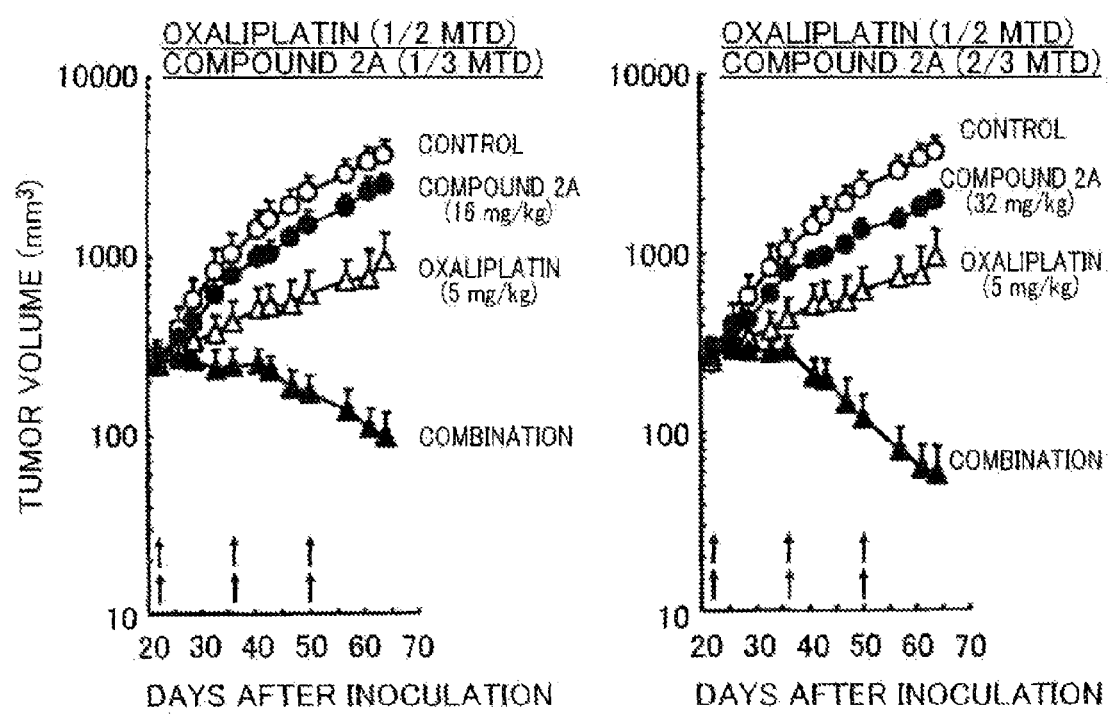

The antitumor effect of the combination of compound 2A and oxaliplatin was stronger than the effects observed with single agents at the same dosage in both methods of administration: compound 2A administered once a week (FIG. 5-1) and compound 2A administered once in two weeks (FIG. 5-2). Furthermore, the combination of compound 2A and oxaliplatin showed a synergistic antitumor effect without enhancing toxicity as determined from the weight reduction.

Therefore, the combination of compound 2A and oxaliplatin is expected to become an effective combination therapy in clinical practice.

Example 6

Antitumor Effect of the Combination of a Water-Soluble Prodrug (Compound 2A) with Gemcitabine (Compound 3B) in the Human Pancreatic Cancer Capan-1 Xenograft Model Cell Growth Human pancreatic cancer Capan-1 was purchased from ATCC. Cells were monolayer cultured in RPMI1640 supplemented with 10% (v/v) fetal bovine serum.

Generation of Xenograft Models

Five-week old male athymic nude mice (BALB/c nu/nu) were purchased from Charles River Japan. The mice were reared for at least one week prior to the experiment at the animal facility of the research institute.

A single cell suspension of Capan-1 ($8.4 \times 10^6$ cells per mouse) was inoculated subcutaneously into the right side of the abdomen of each mouse. The tumor size of each mouse was measured twice a week and the tumor volume was estimated using the $ab^2/2$ formula (a and b refer to the length and width of the tumor, respectively). Randomization and administration of pharmaceuticals were begun the day the tumor volume exceeded 100 mm³

Test Reagents

Compound 2A was prepared in the same manner as in Example 2. Gemcitabine was purchased from Eli Lilly.

Dosage:

compound 2A: 34 mg/kg/injection (24 mg/kg/injection as free base) (½ MTD); gemcitabine: 200 mg/kg/injection (½ MTD) and 400 mg/kg/injection (MTD).

Method of Administration

Compound 2A was dissolved and diluted in 1 mM citric acid/physiological saline solution (pH3.1-3.2), and intravenously administered once a week for four consecutive weeks. Gemcitabine was dissolved and diluted in physiological saline, and intravenously administered once a week for four consecutive weeks.

Results

The antitumor effect of the combination of compound 2A and gemcitabine was examined using the human pancreatic cancer Capan-1 xenograft model. Compound 2A was administered once a week for four consecutive weeks. Gemcitabine was administered once a week for four consecutive weeks.

Figure 6:
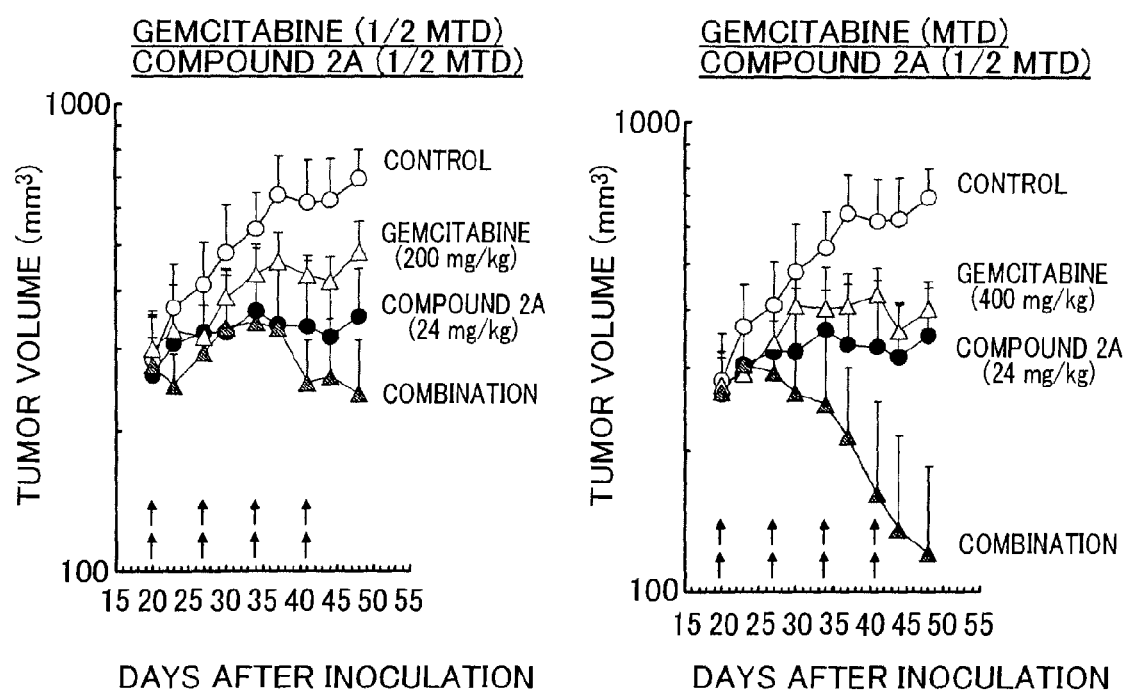
FIG. 6 shows the antitumor effects as a result of combination therapy using compound 2A and gemcitabine in the human pancreatic cancer Capan-1 xenograft model, in which both compound 2A and gemcitabine were administered once a week. The arrows in the upper row indicate the days that compound 2A was administered, and the arrows in the lower row indicate the days that gemcitabine was administered. The vertical bars at each point indicate standard deviation. Symbols in the graph are the following: gemcitabine: open triangles; compound 2A: filled circles; combination: filled triangles; and vehicle: open circles. Each group consisted of five mice, and the tumor volume is their average.

The antitumor effect of the combination of compound 2A and gemcitabine was stronger than the effects observed with single agents at the same dosage. The combination of compound 2A and gemcitabine led to tumor regression and showed at least an additive antitumor effect without enhancing toxicity as determined from the weight reduction (FIG. 6).

Therefore, the combination of compound 2A and gemcitabine is expected to become an effective combination therapy in clinical practice.

Example 7

Antitumor Effect of the Combination of a Water-Soluble Prodrug (Compound 2A) and Capecitabine (Compound 6B) in the Human Breast Cancer MX-1 Xenograft Model Proliferation of Cells Human breast cancer MX-1 was a gift from the Japanese Foundation for Cancer Research. Tumor sections were subcutaneously inoculated and maintained as xenografts.

Generation of Xenograft Models

Five-week old female athymic nude mice (BALB/c nu/nu) were purchased from Charles River Japan. The mice were reared for at least one week prior to the experiment at the animal facility of the research institute.

Tumor sections of MX-1 (approximately 3 mm in diameter) were inoculated subcutaneously into the right side of the abdomen of each mouse. The tumor size of each mouse was measured twice a week and the tumor volume was estimated using the $ab^2/2$ formula (a and b refer to the length and width of the tumor, respectively). Randomization and administration of pharmaceuticals were begun the day the tumor volume exceeded 100 mm$^3$ Test Reagents Compound 2A and capecitabine (compound 6B) prepared in the same manner as in Example 2 were used. The dosage is as shown below.

Dosage:

compound 2A: 8.4 mg/kg/injection (6 mg/kg/injection as free base) (¼ MTD) and 17 mg/kg/injection (12 mg/kg/injection as free base) (½ MTD); and capecitabine: 250 mg/kg/injection (½ MTD).

Method of Administration

Compound 2A was dissolved and diluted in 1 mM citric acid/physiological saline solution (pH3.1-3.2), and intravenously administered once a week for three consecutive weeks. Capecitabine was dissolved in 40 mM citric acid buffer (pH6) containing 5% gum arabic, and orally administered once a day for five consecutive days followed by no administration for two days. The cycle was repeated three times (total: 15 administrations).

Results

The antitumor effect of the combination of compound 2A and capecitabine was examined in the human breast cancer MX-1 xenograft model. In one therapeutic cycle, compound 2A was intravenously administered once a week for three consecutive weeks; and capecitabine was orally administered once a day for five consecutive days, then medication was discontinued for two days, and this cycle was repeated three times (total: 15 administrations).

Figure 7:
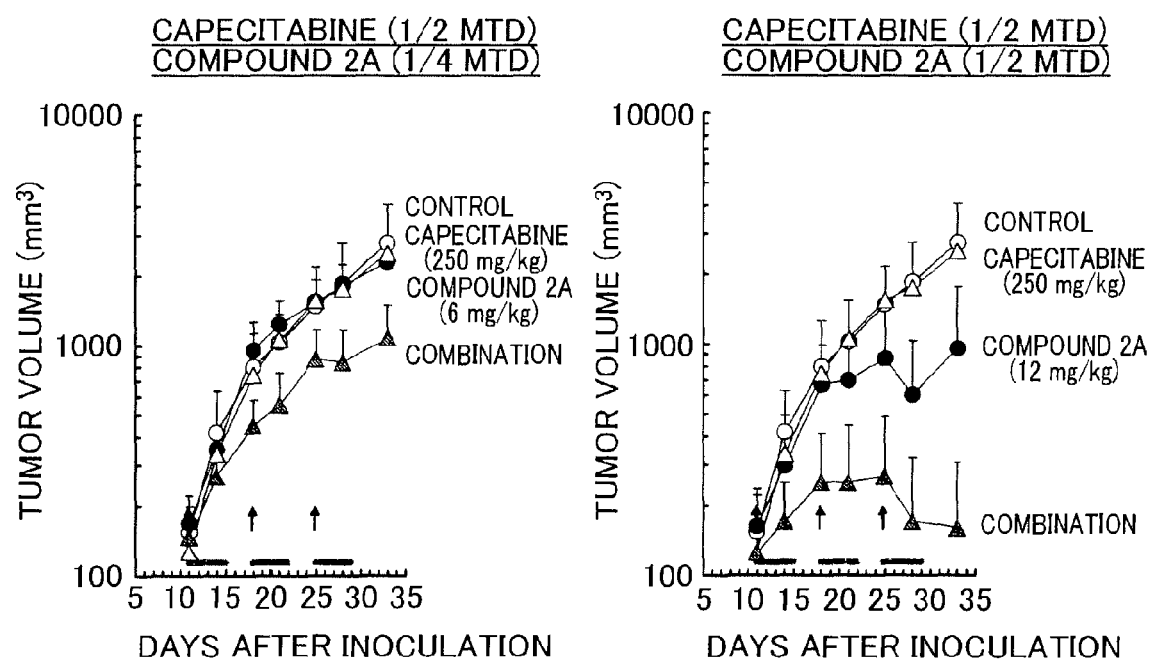
FIG. 7 shows the antitumor effects as a result of single or combination therapy using compound 2A and capecitabine (compound 6B) in the human breast cancer MX-1 xenograft model. Compound 2A was administered intravenously once a week for a total of three times, and capecitabine was orally administered in three repeated cycles of: administration for five consecutive days, followed by discontinuation of medication for two days. The arrows indicate the days that compound 2A was administered, and the horizontal bars on the X axis indicate the days that capecitabine was administered. The vertical bars at each point indicate standard deviation. Symbols in the graph are the following: capecitabine: open triangles; compound 2A: filled circles; combination: filled triangles; and vehicle: open circles. Each group consisted of five mice, and the tumor volume is their average.

As shown in FIG. 7, the antitumor effect of the combination of compound 2A and capecitabine (compound 6B) was stronger than the effects observed with single agents at the same dosage. Furthermore, in the MX-1 xenograft model, the combination of compound 2A and capecitabine (compound 6B) showed an additive antitumor effect without enhancing toxicity as determined from the weight reduction. Thus, the combined use of compound 2A and capecitabine has a significant effect and the combination is expected to become an effective combination therapy in clinical practice.

Although compound 2A is a hydrochloride salt, by changing the reaction lot, reaction scale, reaction solvent, reaction time, reaction temperature, type and equivalence of reagents, methods of treating the reaction solutions, normality (N) of the aqueous hydrochloric acid solution used when washing the reaction solution in process 2-A, and/or normality of hydrochloric acid used in process 2-B, differences may arise in the amount (molar ratio with respect to the free base) of hydrochloric acid added as salt to the free camptothecin derivative (free base). Therefore, the dosage of compound 2A used in Examples 2 to 7 was expressed both in terms of the dosage based on the actually measured weight, and the dosage based on the weight obtained by converting the actually measured weight to the weight of the free base. The dosage based on the weight obtained by converting the actually measured weight to the weight of the free base was used for the dosage of compound 2A shown in the figures.

The invention claimed is:

1. A cancer therapeutic agent comprising a combination of compound A described below, or a pharmaceutically acceptable salt thereof, and compound B described below, or a pharmaceutically acceptable salt thereof:

Compound A: a water-soluble prodrug represented by the following formula:

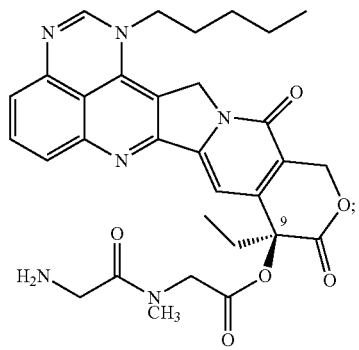

Compound B: at least one type of compound selected from the group consisting of a platinum-type anticancer compound, selected from the group consisting of cisplatin carboplatin, oxaliplatin, and nedaplatin; a gemcitabine-type compound, selected from the group consisting of gemcitabine and Ara-C; a 5-FU-type compound, selected from the group consisting of 5-FU, doxifluridine, UFT, carmofur, S-1, and capecitabine; a taxane-type compound, selected from the group consisting of Taxotere, IDN 5109, BMS 188797, BMS184476, paclitaxel, and docetaxel; a vinca alkaloid-type compound, selected from the group consisting of vinorelbine, vincristine, vinblastine, and videsine; an anticancer tyrosine kinase inhibitor compound, and an anticancer monoclonal antibody.

2. The cancer therapeutic agent of claim 1, wherein the cancer is a solid tumor.

3. The cancer therapeutic agent of claim 1, wherein the cancer is colorectal cancer, lung cancer, breast cancer, stomach cancer, cervical cancer, bladder cancer, rectal cancer, pancreatic cancer, and/or ovarian cancer.

4. A method for treating cancer comprising the step of administering to a patient in need thereof a therapeutically effective dose of the cancer therapeutic agent of claim 1.

* * * * *